United States Patent
Rao et al.

(10) Patent No.: US 10,370,538 B2
(45) Date of Patent: Aug. 6, 2019

(54) PROBES FOR RAPID AND SPECIFIC DETECTION OF MYCOBACTERIA

(71) Applicant: The Board of Trustees of the Leland Stanford Junior University, Palo Alto, CA (US)

(72) Inventors: Jianghong Rao, Sunnyvale, CA (US); Yunfeng Cheng, Stanford, CA (US); Jinghang Xie, Fremont, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 633 days.

(21) Appl. No.: 15/001,591

(22) Filed: Jan. 20, 2016

(65) Prior Publication Data

US 2017/0044593 A1  Feb. 16, 2017

Related U.S. Application Data

(60) Provisional application No. 62/203,635, filed on Aug. 11, 2015.

(51) Int. Cl.
| | |
|---|---|
| *C07D 501/52* | (2006.01) |
| *C09B 11/24* | (2006.01) |
| *C12Q 1/689* | (2018.01) |
| *C07D 501/32* | (2006.01) |
| *C07D 501/36* | (2006.01) |

(52) U.S. Cl.
CPC ............ *C09B 11/24* (2013.01); *C07D 501/32* (2013.01); *C07D 501/36* (2013.01); *C12Q 1/689* (2013.01)

(58) Field of Classification Search
CPC ...................................................... C09B 11/24
USPC ........................................................ 540/217
See application file for complete search history.

(56) References Cited

U.S. PATENT DOCUMENTS

| | | | |
|---|---|---|---|
| 6,229,055 B1 | 5/2001 | Klaubert et al. | |
| 9,834,681 B2 * | 12/2017 | Rao | ......................... C09B 57/02 |
| 2009/0047692 A1 | 2/2009 | Corry et al. | |

OTHER PUBLICATIONS

Dye C, et al. (2008) Measuring tuberculosis burden, trends, and the impact of control programs. Lancet Infect. Dis. 8(4):233-243.
Zumla A, Raviglione M, Hafner R, & von Reyn CF (2013) Tuberculosis. N. Engl. J. Med. 368(8):745-755.
Anonymous (2013) Global Tuberculosis Report 2013, World Health Organization.

(Continued)

*Primary Examiner* — Jezia Riley
(74) *Attorney, Agent, or Firm* — Thomas|Horstemeyer, LLP

(57) ABSTRACT

The compositions of the present disclosure provide novel fluorogenic probes for use in the specific imaging and detection of mycobacteria species, and in particular β-lactam-antibiotic resistant. Specificity for mycobacteria is conferred on these probes by incorporating a moiety that specifically targets the unique trapping mechanism of the DprE1 found in in mycobacteria. Accordingly, only Mycobacteria species that express both a β-lactamase and DprE1 enable both the activation of the caged fluorescent probe, and the affixing of the released fluorescent probes to the bacteria cells through the functioning reduction-covalent binding mechanism. Advantageously, such a probe is able, at its most sensitive, to allow single *mycobacterium* detection.

6 Claims, 31 Drawing Sheets

(56) References Cited

OTHER PUBLICATIONS

Urdea M, et al. (2006) Requirements for high impact diagnostics in the developing world. Nature 444 Suppl 1:73-79.

Keeler E, et al. (2006) Reducing the global burden of tuberculosis: the contribution of improved diagnostics. Nature (444):49-57.

McNerney R & Daley P (2011) Towards a point-of-care test for active tuberculosis: obstacles and opportunities. Nat. Rev. Microbiol. 9(3):204-213.

Dheda K, Ruhwald M, Theron G, Peter J, & Yam WC (2013) Point-of-care diagnosis of tuberculosis: past, present and future. Respirology 18(2):217-232.

Bush K & Jacoby GA (2010) Updated Functional Classification of beta-Lactamases. Antimicrob. Agents Chemother. 54(3):969-976.

Zlokarnik G, et al. (1998) Quantitation of transcription and clonal selection of single living cells with beta-lactamase as reporter. Science 279(5347):84-88.

Gao WZ, Xing BG, Tsien RY, & Rao JH (2003) Novel fluorogenic substrates for imaging δ-lactamase gene expression. J. Am. Chem. Soc. 125(37):11146-11147.

Xing B, Khanamiryan A, & Rao JH (2005) Cell-permeable near-infrared fluorogenic substrates for imaging beta-lactamase activity. J. Am. Chem. Soc. 127(12):4158-4159.

Yao H, So MK, & Rao J (2007) A bioluminogenic substrate for in vivo imaging of beta-lactamase activity. Angew. Chem.-Int Edit 46(37):7031-7034.

Kong Y, et al. (2010) Imaging tuberculosis with endogenous beta-lactamase reporter enzyme fluorescence in live mice. Proc. Natl. Acad. Sci. U. S. A. 107(27):12239-12244.

Rukavishnikov A, Gee KR, Johnson I, & Corry S (2011) Fluorogenic cephalosporin substrates for beta-lactamase TEM-1. Anal. Biochem. 419(1):9-16.

Zhang JX, Shen Y, May SL, Nelson DC, & Li SW (2012) Ratiometric fluorescence detection of pathogenic bacteria resistant to broad-spectrum ss-lactam antibiotics. Angew. Chem.-Int Edit. 51(8):1865-1868.

Shi HB, et al. (2014) Engineering the Stereochemistry of Cephalosporin for Specific Detection of Pathogenic Carbapenemase-Expressing Bacteria. Angew. Chem.-Int. Edit. 53(31):8113-8116.

Cheng YF, et al. (2014) Fluorogenic Probes with Substitutions at the 2 and 7 Positions of Cephalosporin are Highly BlaC-Specific for Rapid Mycobacterium tuberculosis Detection. Angew. Chem.-Int. Edit. 53(35):9360-9364.

Xie HX, et al. (2012) Rapid point-of-care detection of the tuberculosis pathogen using a BlaC-specific fluorogenic probe. Nat. Chem. 4(10):802-809.

Makarov V, et al. (2009) Benzothiazinones Kill Mycobacterium tuberculosis by Blocking Arabinan Synthesis. Science 324(5928):801-804.

Ribeiro A, et al. (2011) Analogous Mechanisms of Resistance to Benzothiazinones and Dinitrobenzamides in Mycobacterium smegamatis. PLoS One 6(11):7.

Trefzer C, et al. (2010) Benzothiazinones: Prodrugs That Covalently Modify the Decaprenylphosphoryl-beta-D-ribose 2-epimerase DprE1 of Mycobacterium tuberculosis. J. Am. Chem. Soc. 132(39)13663-13665.

van der Poll T & Opal SM (2009) Pathogenesis, treatment, and prevention of pneumococcal pneumonia. Lancet 374 (9700):1543-1556.

Cole AM, et al. (2001) Determinants of *Staphylococcus aureus* nasal carriage. Clin. Diagn. Lab. Immunol. 8(6):1064-1069.

Watkins DA, Chahine A, Creger RJ, Jacobs MR, & Lazarus HM (1993) Corynebacterium-Striatum-A Diphtheroid With Pathogenic Potential Clin. Infect. Dis. 17(1):21-25.

Paik S, et al. (2005) Identification of virulence determinants for endocarditis in Streptococcus sanguinis by signature-tagged mutagenesis. Infect. Immun. 73(9):6064-6074.

Batt et al. 'Structural basis of inhibition of Mycobacteriumtuberculosis DprE1 by benzothiazinone inhibitors', PNAS, 2012, vol. 109, pp. 11354-11359.

Kobayashi et al. 'Highly Activatable and Rapidly Releasable Caged Fluorescein Derivatives', Journal of American Chemical Society, 2007, vol. 129, pp. 6696-6697.

Lavis et al. 'Bright Building Blocks for Chemical Biology', ACS Chemical Biology, Feb. 18, 2014, vol. 9, pp. 855-866.

\* cited by examiner

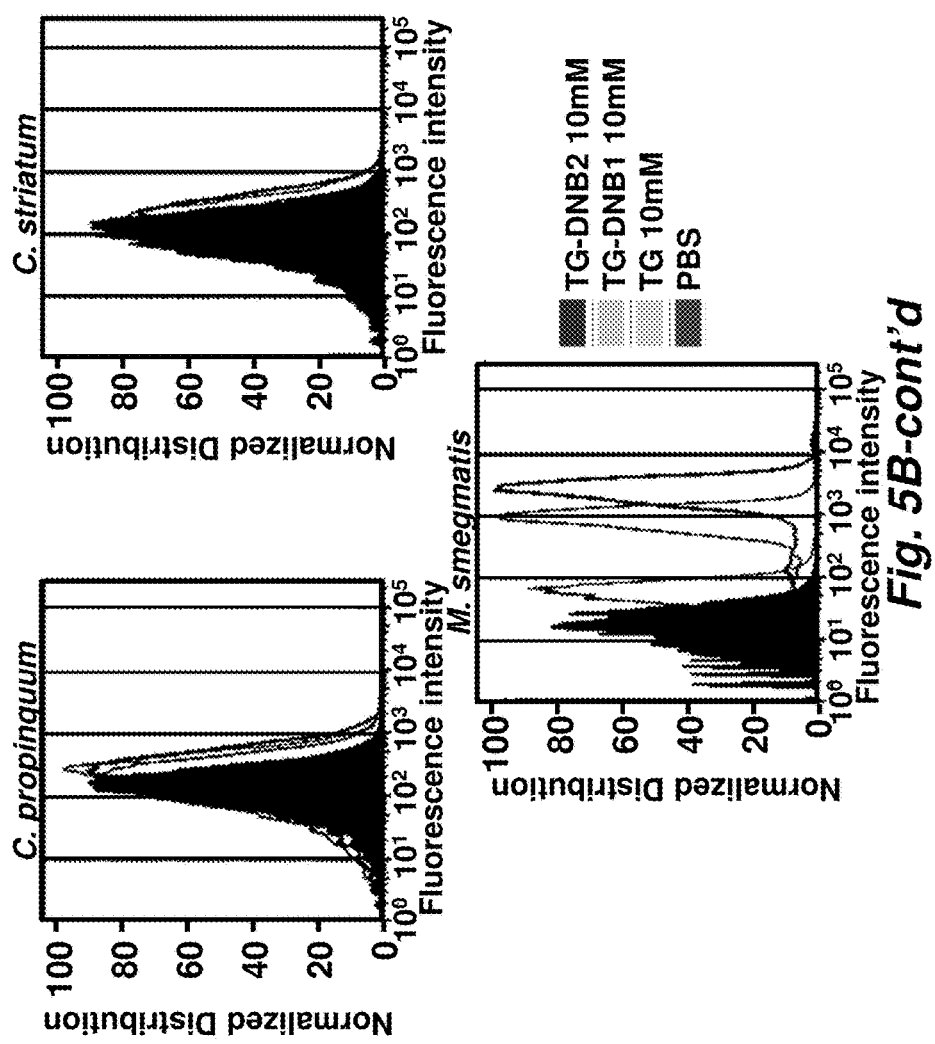
Fig. 5B-cont'd

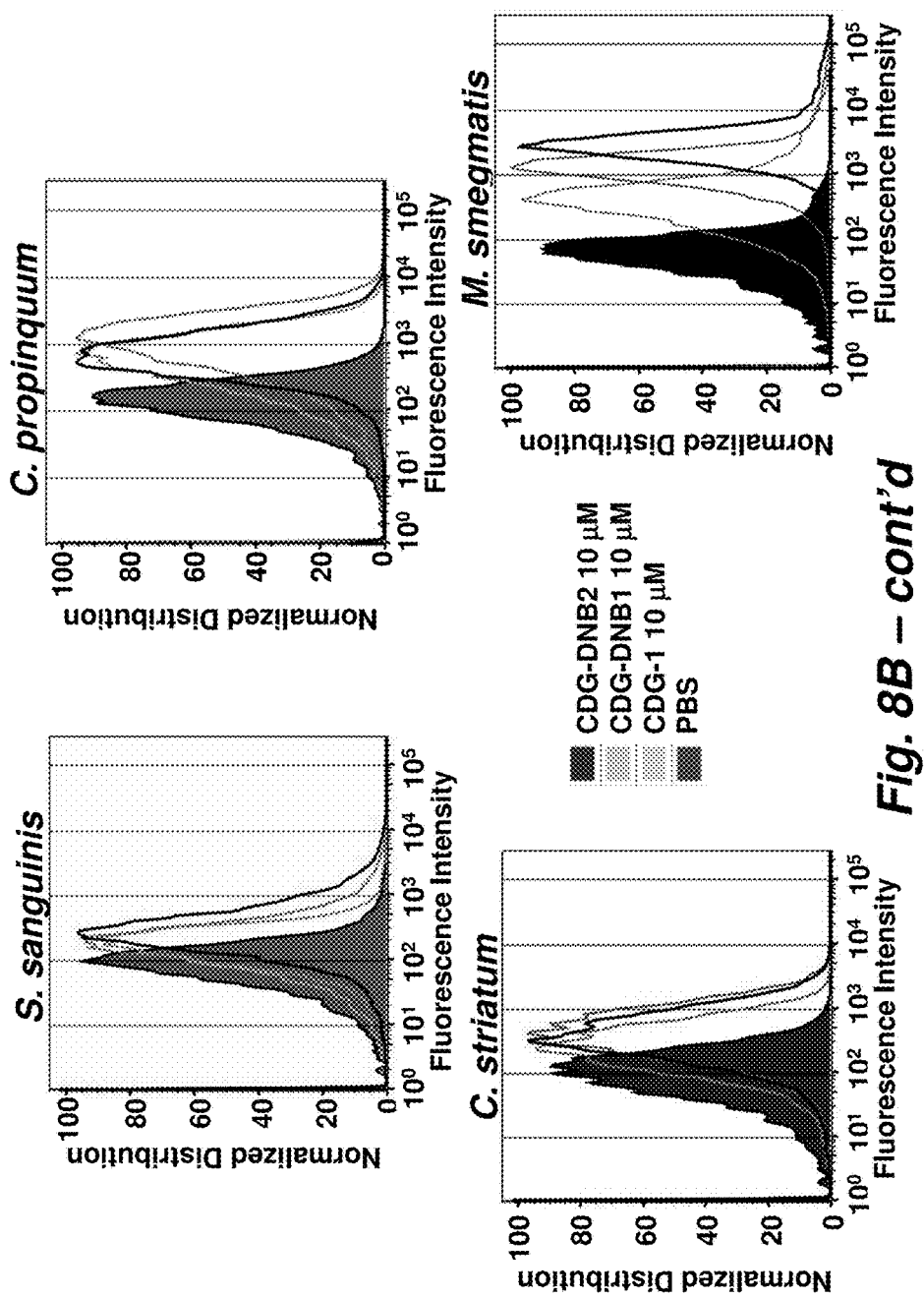
Fig. 8B – cont'd

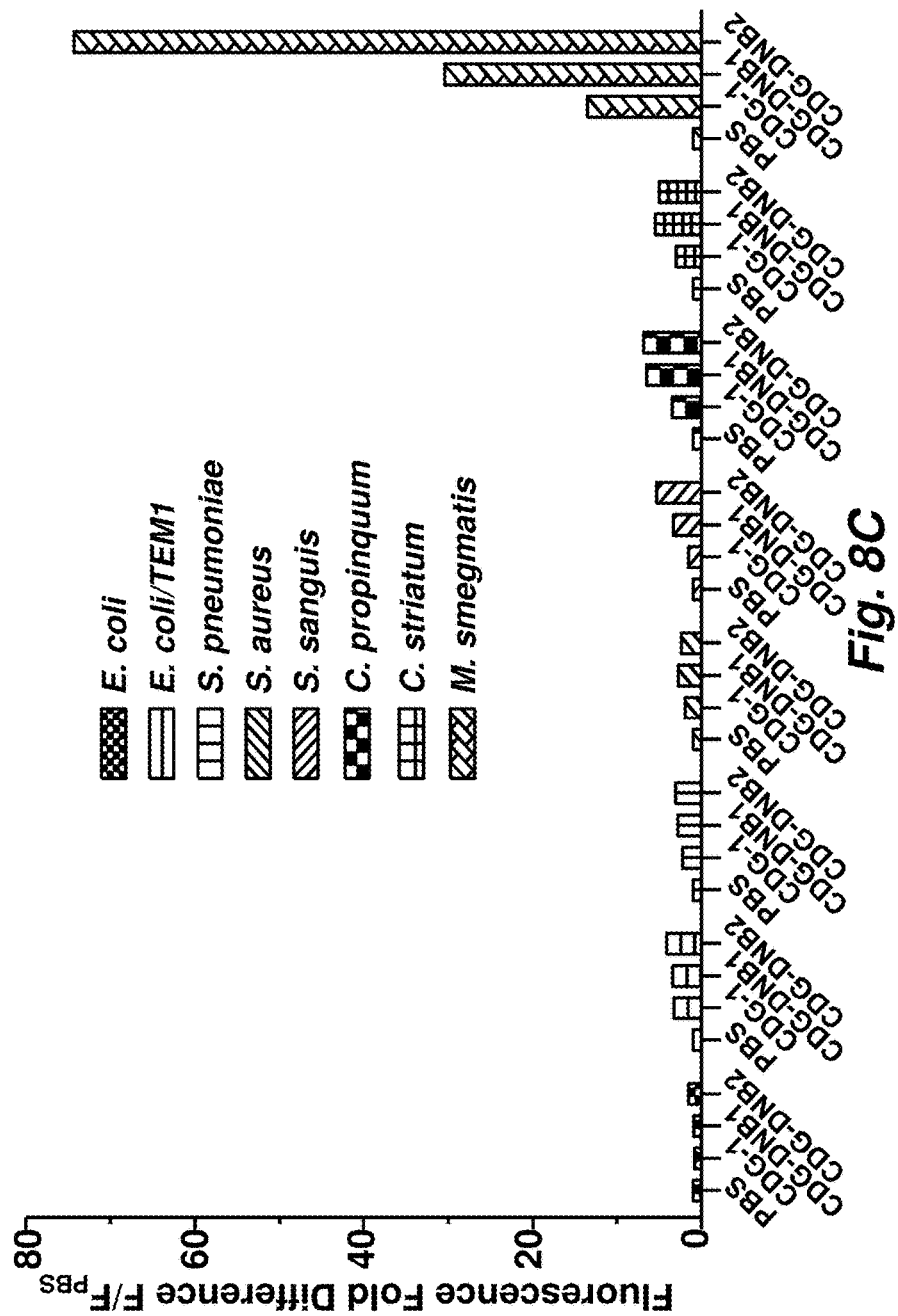

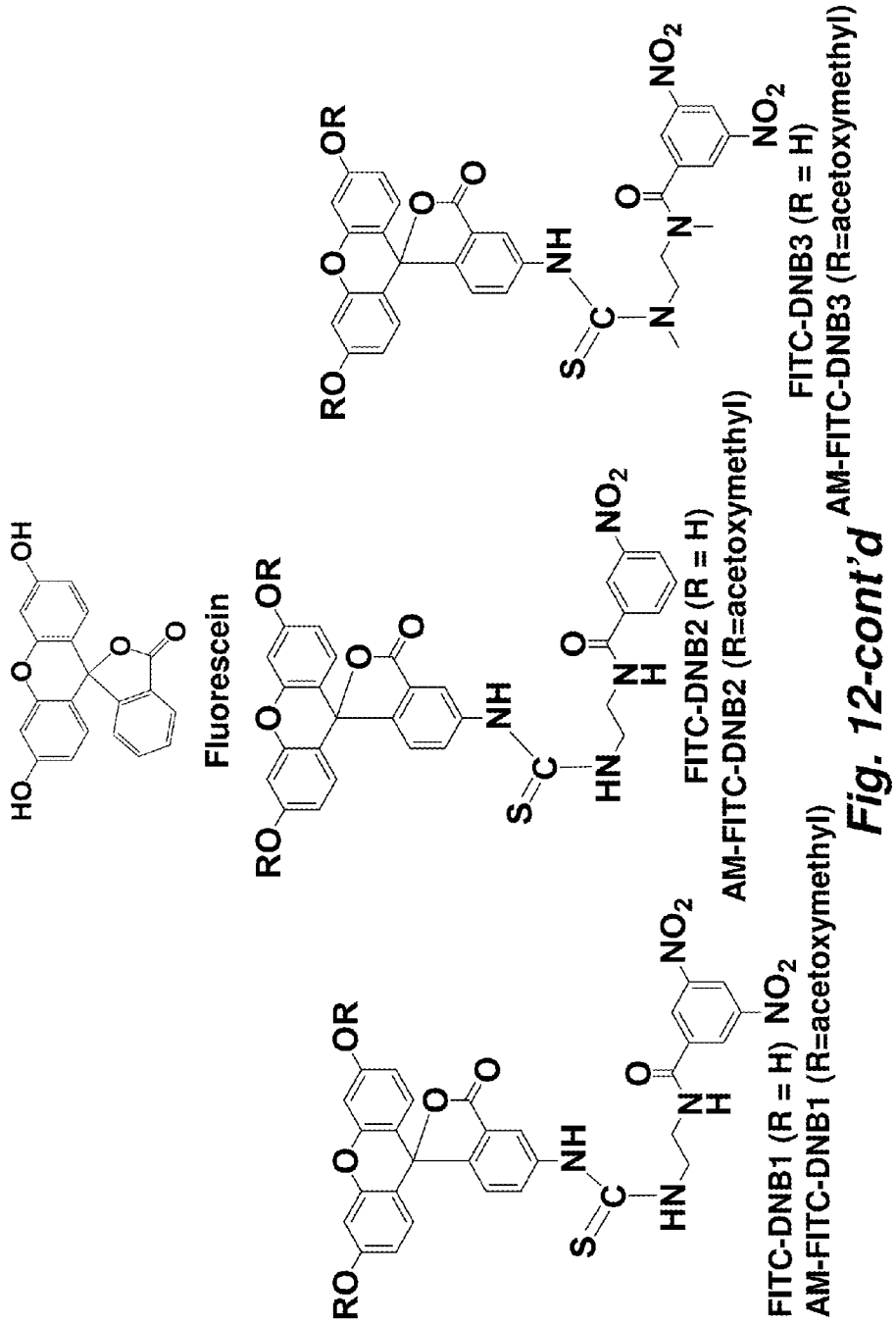
Fig. 12-cont'd

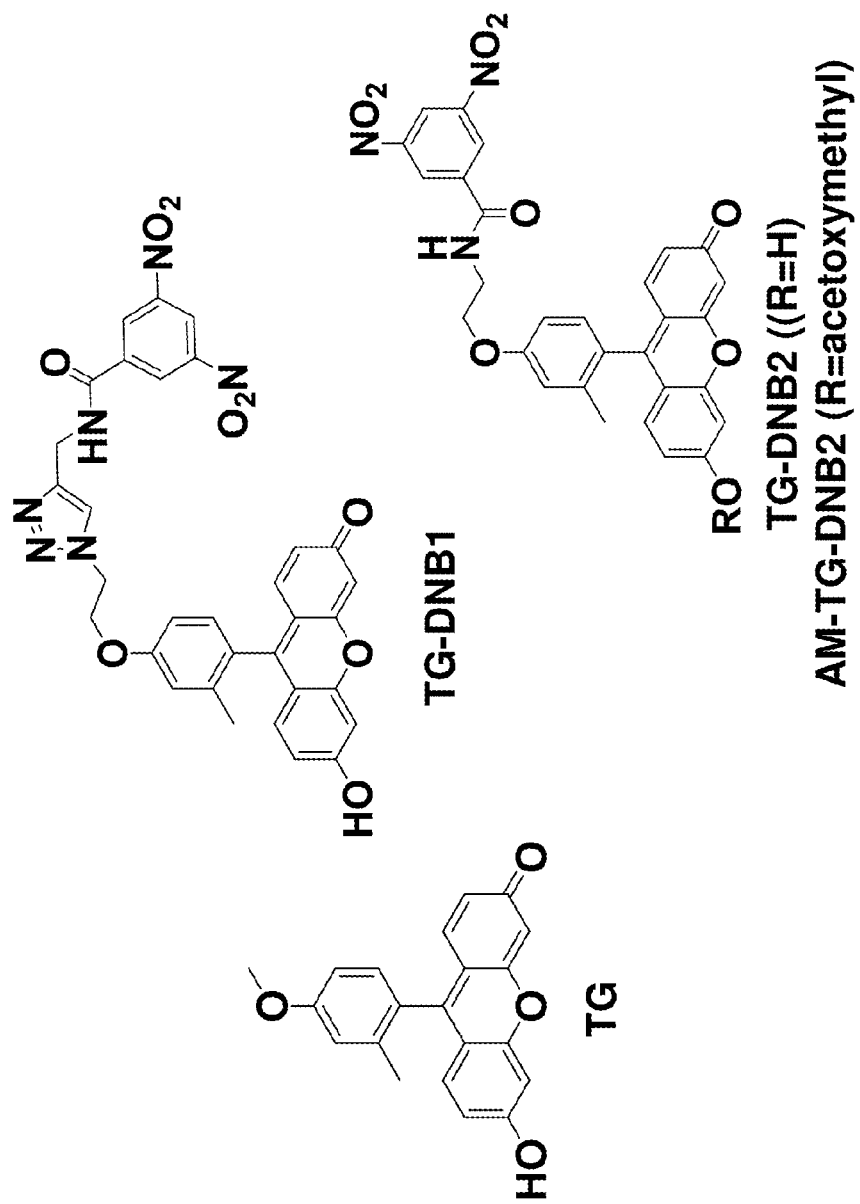
Fig. 12-cont'd n = 0 or 1;

$R_4$ is a hydrogen, an alkyl, a substituted alkyl, an aromatic group, a substituted aromatic group; a thiophene, or substituted thiophene;

$R_5$ is H, OMe, Me, -CH$_2$CH$_3$, -CF$_3$, -CH$_2$CF$_3$, -CF$_2$CH$_3$, -CHF$_2$, -CH$_2$F, -OCH$_2$F, or –OCHF$_2$;

$R_6$ and $R_7$ are each H or ◁

$R_8$ is O or S.

PROBES FOR RAPID AND SPECIFIC DETECTION OF MYCOBACTERIA

CROSS REFERENCE TO RELATED APPLICATIONS

This application claims priority benefit of U.S. Provisional Patent Application Ser. No. 62/203,635 filed on Aug. 11, 2015 and titled "PROBES FOR RAPID AND SPECIFIC DETECTION OF MYCOBACTERIA" the entire disclosure of which is herein incorporated by reference in its entirety.

TECHNICAL FIELD OF THE DISCLOSURE

The present disclosure relates to probes specific for β-lactam-resistant mycobacteria. The disclosure further relates to methods of detecting mycobacterial strains that are β-lactam-resistant and Decaprenylphosphoryl-β-D-ribose 2'-Epimerase (DprE1)-positive.

BACKGROUND

The bacterial genus *Mycobacterium*, which consists of over 120 known species, is a major burden of infectious disease in humans. As the most pathogenic species, *Mycobacterium Tuberculosis* Complex (MTBC), including *Mycobacterium tuberculosis*, *Mycobacterium africanum*, *Mycobacterium microti* and *Mycobacterium bovis*, infects around one-third of the world's population and claims over 1.5 million lives each year (Dye et al., (2008) *Lancet Infect. Dis.* 8: 233-243; Zumla et al., (2013) *N. Engl. J. Med.* 368: 745-755; Anonymous (2013) Global Tuberculosis Report 2013, World Health Organization).

Tuberculosis is a highly infectious airborne disease. A rapid and accurate detection of MTBC is considered to be the most critical step in containing the spread and decreasing the mortality rate of this disease (Urdea et al., (2006) *Nature* 444 (Suppl. 1): 73-79; Keeler et al., (2006) *Nature:* 49-57; McNerney & Daley (2011) *Nat. Rev. Microbiol.* 9: 204-213; Dheda et al., (2013) *Respirology* 18: 217-232). Other than MTBC, Non-Tuberculosis Mycobacteria (NTM), such as slow-growing *Mycobacterium avium* and *Mycobacterium intracellulare*, can also cause skin disease, Johne's disease, inflammatory bowel disease, and Crohn's disease with relatively high morbidity and mortality.

The slow growth rate of *Mycobacterium tuberculosis* presents a large hurdle that needs to be overcome for the effective detection of these virulent pathogens. So far, no diagnostic assay is cost-effective and can also provide results within a single patient-health-care visit (within a couple of hours) (Keeler et al., (2006) *Nature:* 49-57; McNerney & Daley (2011) *Nat. Rev. Microbiol.* 9: 204-213; Dheda et al., (2013) *Respirology* 18: 217-232). Current diagnosis such as the gold standard culture-based technique, smear microscopy, and nucleic acid-based diagnostic methods are time-consuming, expensive, or technically demanding.

The intrinsic resistance of mycobacteria to β-lactam antibiotics worsens the global crisis and treatment options. Among all the resistance mechanisms, β-lactamase is believed to be the key contributor. Since the discovery of the first β-lactamase in 1940, a large number of β-lactamases have been identified that can hydrolyze a variety of β-lactam antibiotics, from penicillin to cephalosporins and carbapenems (Bush & Jacoby (2010) *Antimicrob. Agents Chemother.* 54: 969-976).

To assay the activity of β-lactamases, a series of non-specific fluorogenic and luminogenic probes has been developed that take advantage of the high sensitivity of fluorescence and luminescence detecting mechanism (Zlokarnik et al., (1998) *Science* 279: 84-88; Gao et al., (2003) *J. Am. Chem. Soc.* 125: 11146-11147; Xing et al., (2005) *J. Am. Chem. Soc.* 127: 4158-4159; Yao et al., (2007) *Angew. Chem. Int. Edit.* 46: 7031-7034; Kong et al., (2010) *Proc. Natl. Acad. Sci. U.S.A.* 107: 12239-12244; Rukavishnikov et al., (2011) *Anal. Biochem.* 419: 9-16; Zhang et al., (2012) *Angew. Chem. Int. Edit.* 51: 1865-1868).

Fluorogenic probes for the specific pathogen detection have been developed. For example, by engineering the stereochemistry of cephalosporin a series of fluorogenic probes was developed that showed specificity for Carbapenem-Resistant Enterobacteriaceae (CRE) (Shi et al., (2014) *Angew. Chem. Int. Edit.* 53: 8113-8116). By targeting BlaC, an ambler class A β-lactamase that is highly conserved in MTBC clinical isolates and plays a key role for the pervasive β-lactam-antibiotic resistance, a series of fluorogenic probes for rapid point-of-care detection of MTBC was developed (Cheng et al., (2014) *Angew. Chem. Int. Edit.* 53: 9360-9364; Xie et al., (2012) *Nat. Chem.* 4: 802-809). However, although these probes exhibit advantages as low-cost triage tests for use in the resource-limited areas, they are deficient in the sensitivity and specificity required for use in both microscopy centers and as probes for use with point-of-care methods.

SUMMARY

The present disclosure encompasses embodiments of probes useful for the selective detection of mycobacteria, and in particular tuberculosis-related mycobacteria that have β-lactamase BlaC and the enzyme Decaprenylphosphoryl-β-D-ribose 2'-epimerase (DprE1), thereby distinguishing those species from other mycobacteria.

One aspect of the disclosure encompasses embodiments of a probe specific for a *mycobacterium*, said probe consisting of a detectable label conjugated to a β-lactamase substrate group, and wherein the detectable label can have a *mycobacterium*-specific DprE1-trapping moiety conjugated thereto.

Accordingly, the disclosure encompasses embodiments of a probe specific for a *mycobacterium*, wherein said probe can consist of a detectable label covalently attached to a *mycobacterium*-specific decaprenylphosphoryl-β-D-ribose 2'-epimerase (DprE1)-trapping moiety, or an ester or salt thereof.

In some embodiments of this aspect of the disclosure, the probe can further comprise a β-lactamase substrate group covalently attached to the detectable label, wherein said probe specifically detects a *mycobacterium* having a β-lactamase activity.

In embodiments of this aspect of the disclosure, the probe can be admixed with a carrier or vehicle.

Another aspect of the disclosure encompasses embodiments of a method of selectively detecting a *mycobacterium*, said method comprising the steps of: contacting a sample suspected of having a *mycobacterium* with a composition comprising a probe, said probe consisting of a detectable label covalently attached to a *mycobacterium*-specific decaprenylphosphoryl-β-D-ribose 2'-epimerase (DprE1)-trapping moiety; and detecting a signal emitted by the probe covalently attached to a DprE1 protein of a *mycobacterium*.

In some embodiments of this aspect of the disclosure, the probe can further comprise a β-lactamase substrate group covalently attached to the detectable label, wherein said probe specifically detects a *mycobacterium* having a β-lactamase activity.

In some embodiments of this aspect of the disclosure, the method can further comprise the steps of: allowing an effective period for a mycobacterial β-lactamase BlaC activity to cleave the β-lactamase substrate group, thereby releasing the detectable label and the *mycobacterium*-specific DprE1-trapping moiety conjugated thereto from the β-lactamase substrate group; and specifically detecting β-lactamase substrate group covalently attached to the detectable label.

In some embodiments of this aspect of the disclosure, the method can further comprise, before detecting the detectable label, washing the sample to remove probe not in contact with mycobacteria therein.

BRIEF DESCRIPTION OF THE DRAWINGS

Aspects of the present disclosure will be more readily appreciated upon review of the accompanying drawings. The drawings are described in greater detail in the description and examples below.

FIG. 5A is a series of digital overlay images of bright field and green fluorescence.

FIG. 5B illustrates a series of histograms of fluorescence-activated flow cytometry.

FIG. 5C is a graphical plot of the mean fluorescence intensity from flow cytometry for indicated strains and probes. The fold increasing (F/F$_{PBS}$) was calculated by normalizing against the fluorescence intensity of PBS-treated cells. Experiments were performed twice with similar results.

FIG. 8C is graph illustrating the mean values of fluorescence intensity collected by flow cytometry were plotted with GraphPad PRISM 5. The fluorescence intensity of PBS treated cells of each strain was arbitrarily set as 1 to show the fold increasing (F/F$_{PBS}$).

DETAILED DESCRIPTION

Figure 1:
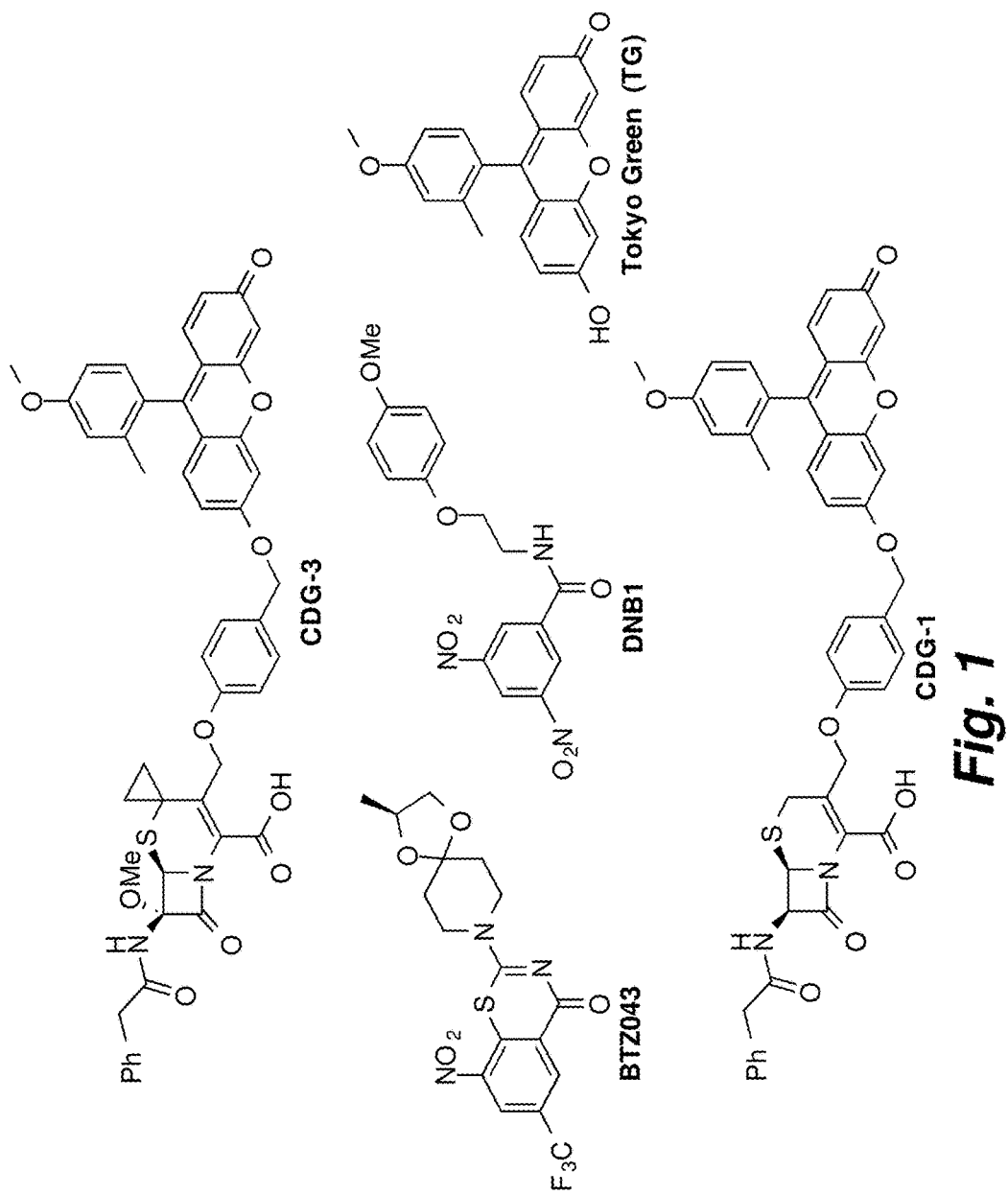
FIG. 1 illustrates structures of CDG-3, BTZ043, DNB1, TG, and CDG-1.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

MTBC, *Mycobacterium Tuberculosis* Complex; FITC, Fluorescein Isothiocyanate; FITC-AM, Fluorescein Isothiocyanate-Acetoxymethyl ester; Rd, Rhodol (3'-Amino-6'-hydroxy-fluoran); Rd-DNB, Rhodol-Dinitrobenzamide (and derivatives); DprE1, Decaprenylphosphoryl-β-D-ribose 2'-Epimerase; DprE1$_{sm}$, Decaprenylphosphoryl-β-D-ribose 2'-Epimerase of *M. smegmatis*; DPR, Decaprenylphosphoryl-β-D-ribofuranose; TFAA, Trifluoroacetic anhydride; PBS, Phosphate-buffered saline; CPBA, chloroperoxybenzoic acid; DCM, dichloromethane; TFA, trifluoroacetic acid; r.t, room temperature; AM, acetoxymethyl ester.

Definitions

In describing and claiming the disclosed subject matter, the following terminology will be used in accordance with the definitions set forth below.

The term "dinitrobenzamide (DNB)" as used herein is intended to encompass dinitrobenzamide. The term "dinitrobenzamide (DNB)" is further intended to encompass analogs of DNB (mononitro-DNB) wherein one nitro group of the DNB has been replaced with a group that cannot be reduced to a reactive species capable covalently binding to a cysteine in the active site of a decaprenylphosphoryl-β-D-ribose 2'-epimerase. In such derivatives, one nitro group remains that can be reduced to a reactive species capable of covalently binding to a cysteine in the active site of a decaprenylphosphoryl-β-D-ribose 2'-epimerase.

The term "probe" as used herein refers to a compound comprising a detectable label and at least one moiety specific for a target *mycobacterium*, most advantageously for a DprE1-containing *Mycobacterium* species. In the present disclosure, a probe can comprise a detectable label covalently attached to a DprE1-specific dintrobenzamide derivative and can further comprise β-lactamase substrate group. Alternatively, the probe can comprise a detectable label covalently attached to β-lactamase substrate group.

The term "probe specific for" as used herein refers to a detectable probe according to the disclosure that will selectively detect a desired target. Accordingly, the compositions and methods of the disclosure will preferentially detect a tuberculosis-related mycobacteria species and not a bacterial species of a different genus or a non-tuberculosis-related *mycobacterium*.

The term "β-lactamase substrate group" as used herein refers to a group that can be a substrate for the β-lactamase BlaC found in tuberculosis-related *mycobacterium* strains.

The term "*mycobacterium*-specific DprE1-trapping moiety" as used herein refers to a dinitrobenzamide, or mononitro derivative thereof, a dinitrobenzothiazinone or monobenzothiazinone or derivative thereof, that can covalently bind to the cysteine in the active site of a decaprenylphosphoryl-β-D-ribose 2'-epimerase or be modified to covalently bind to the cysteine in the active site of a decaprenylphosphoryl-β-D-ribose 2'-epimerase. The term "DprE1-trapping moiety" may be used interchangeably with the term "*mycobacterium*-specific decaprenylphosphoryl-β-D-ribose 2'-epimerase (DprE1)-trapping moiety."

The term "cephalosporin" as used herein refers to β-lactam compounds in which the β-lactam ring is fused to a 6-membered dihydrothiazine ring, thus forming the cephem nucleus. Side chain modifications to the cephem nucleus can confer an improved spectrum of antibacterial activity, pharmacokinetic advantages, and additional side effects. Most advantageously, the β-lactamase substrate can be a cephalosporin having the formula:

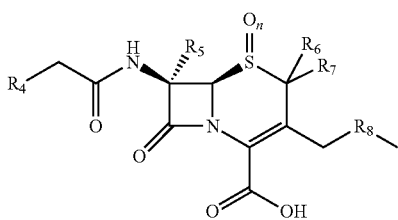

wherein: n=0 or 1; $R_4$ is selected from the group consisting of: a hydrogen, an alkyl, a substituted alkyl, an aromatic group, a substituted aromatic group; a thiophene, or substituted thiophene; $R_5$ is H, OMe, Me, —$CH_2CH_3$, —$CF_3$, —$CH_2CF_3$, —$CF_2CH_3$, —$CHF_2$, —$CH_2F$, —$OCH_2F$, or —$OCHF_2$; $R_6$ and $R_7$ are each H or

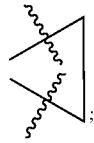

and $R_8$ is O or S.

The term "detectable label" as used herein refers to a dye or any other moiety capable of generating a detectable signal such as a colorimetric, fluorescent, chemiluminescent, or electrochemiluminescent (ECL) signal. Label molecules, known to those skilled in the art as being useful for detection, include chemiluminescent or fluorescent molecules. Suitable light detectable labels include but are not limited to, a fluorescein, an acridine, an alizarene, an azo dye, an anthraquinine dye, a bodipy dye, a coumarin dye, a cyanine dye, a lanthanide complex, an oxazine dye, a phenazathionium dye, a phenazoxonium dye, a porphyorin, a pyrene, a pyrilium, a perylene, a phenoxazine, a phenezine, a rhodol, a rhodamine, or a xanthene dye.

Various fluorescent molecules are known in the art which are suitable for use to label a probe of the present disclosure including, but not limited to, Cascade Blue, Cascade Yellow, 7-amino-4-methylcoumarin, aminocoumarin, hydroxycoumarin, Cy3, Cy5, fluorescein isothiocyanate, Quantum Dye®, Marina Blue, rhodamine red, tetramethylrhodamine, rhodamine 6G, Texas Red, thiazole orange-ethidium heterodimer, TOTAB, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, BODIPY-TR, Cy5,6-FAM, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, TET, 3-Hydroxypyrene 5,8,10-Tri Sulfonic acid, 5-Hydroxy Tryptamine, 5-Hydroxy Tryptamine (5-HT), Acid Fuchsine, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, an aryl-substituted polyolefin, a heteroaryl-substituted polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulfate, Bisbenzamnide, BOBO 1, Biancophor FFG Solution, Blancophor SV, Bodipy Fl, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diainino Naphtyl Sulphonic Acid), Dansyl NH—CH$_3$, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Ethidium Bromide, Euchrysin, Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Maxilon Brilliant Flavin 10 GFF, Maxilon Brilliant Flavin 8 GFF, MPS (Methyl Green Pyronine Stilbene), Mithrarnycin, NBD Amine, Nile Red, Nitrobenzoxadidole, Noradrenaline, Nuclear Fast Red, Nuclear Yellow, Nylosan Brilliant Flavin E8G, Oxazine, Oxazole, Oxadiazole, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, Tokyo Green, TOTO 1, TOTO 3, True Blue, Ultralite, Uranine B, Uvitex SFC, Xylene Orange, XRITC, and YO PRO 1.

The protocol for such incorporation may vary depending upon the fluorescent molecule used. Such protocols are known in the art for the respective fluorescent molecule. Most advantageous for incorporation into the probes of the disclosure is a detectable fluorescent dye.

The term "detectably labeled" as used herein means that a compound such as a probe of the disclosure encompass a moiety that is detectable by light absorbance (a dye) or by emitted florescence (a fluorophore), or that is substituted with some other molecular species that elicits a physical or chemical response that can be observed or detected by the naked eye or by means of instrumentation such as, without limitation, colorimeters, UV spectrophotometers, hand-held florescence or optical light detectors, and the like.

Spectroscopic, photochemical, biochemical, immunochemical, electrical, optical or chemical means can be used to detect such labels. The detection device may be fixed, free-standing, or hand-held, and methods may include, but are not limited to, optical imaging, electronic imaging, imaging with a CCD camera, integrated optical imaging, and mass spectrometry. Further, the amount of labeled or unlabeled probe bound to the target may be quantified. Such quantification may include statistical analysis.

The term "caged" as used herein refers to when a detectable label has been modified by such as the covalent attachment of a moiety that prevents the generation of such as a detectable fluorescent signal or that significantly reduces the intensity of the detectable fluorescent signal.

Figure 17:
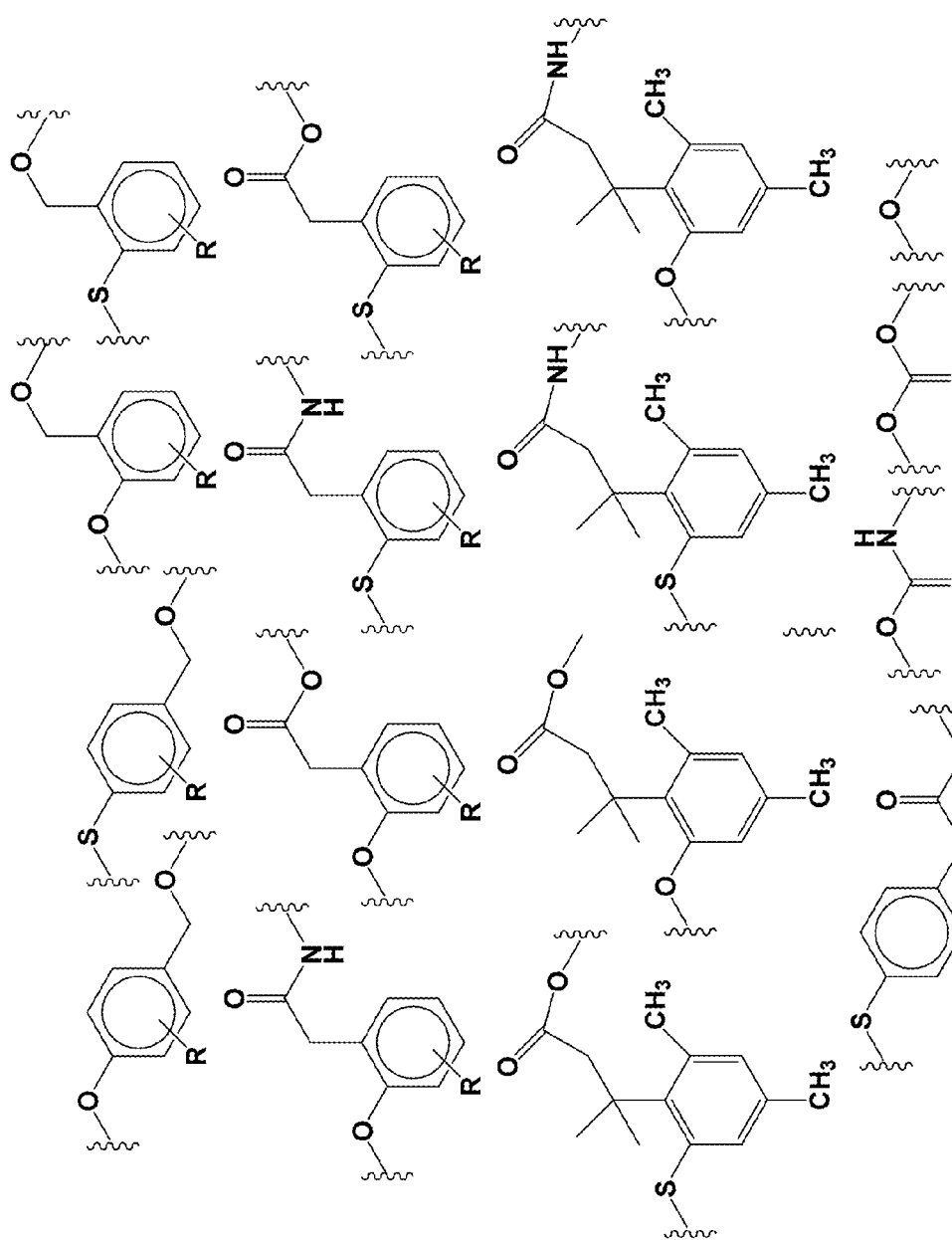
FIG. 17 illustrates embodiments of a linker (the "second linker") useful for covalently connecting a detectable label and a β-lactamase substrate group in probes of the disclosure.

The term "linker" as used herein refers to a chemical moiety comprising a covalent bond or a chain of atoms that covalently attaches at least two other molecular entities so as to form a single compound. In the embodiments of the disclosure a first linker can covalently attach a detectable label to a *mycobacterium*-specific DprE1-trapping moiety. A second linker can covalently attach a detectable label and a β-lactamase substrate group. In various embodiments of the probes of the disclosure the first and second linkers may have the same structures or be different from each other. Examples of the first linker include, but are not intended to be limiting, are ethoxyphenyl, —CH$_2$—CH$_2$—, -1-ethyl 3-methyl 1,2,3-triazole, and —CH$_2$—CH$_2$—NR$_2$—CS—NH$_2$—, wherein R$_2$ is H or —CH$_3$. Examples of the second linker disposed between the detectable label and a β-lactamase substrate group, while not intended to be limiting, are shown in FIG. 17.

The term "selectively detecting" as used herein refers to the ability of a method according to the disclosure to detect a tuberculosis-related *mycobacterium* species or strain but not of other bacterial species and strains that are not tuberculosis-related *mycobacterium* species.

The term "sample" as used herein refers to any liquid, tissue, cell and the like that may be obtained from a human or animal subject. The sample may be isolated from the subject human or animal or remain in vivo. For example, but not intended to be limited, the sample may be a sputum sample, a blood sample, an isolated fragment of a lung tissue, an oral swab, and the like. The sample may be a histological sample where the sample has not been fixed or treated such that, if there is the presence of a tuberculosis-related *mycobacterium*, the activity of the enzyme DprE1 has not been destroyed before contact with a probe of the disclosure. The sample may be a bacterial sample that is cultured to expand the population of bacterial cells subject to the detection methods of the disclosure.

The term "effective period" as used herein refers to an incubation period sufficient for the generation of a detectable signal resulting from the activity of β-lactamase, the reduction of a nitro group of the *mycobacterium*-specific DprE1-trapping moiety to a nitroso group, and the covalent attachment of the fluorophore:DprE1-trapping moiety conjugate to the DprE1 of a tuberculosis-related *mycobacterium*.

The term "tuberculosis-related *mycobacterium*" as used herein refers to *M. tuberculosis*, a genetically diverse species with significant phenotypic differences between clinical isolates, or to such as *M. bovis* that is associated with tuberculosis in, for example, humans, cattle, bison cattle, possums, badgers and kangaroos. Different strains of *M. tuberculosis* are associated with different geographic regions. Microevolutionary variation does affect the relative fitness and transmission dynamics of antibiotic-resistant strains. *M. tuberculosis* is considered to be multidrug-resistant (MDR TB) if it has developed drug resistance to both rifampicin and isoniazid, which are the most important antibiotics used in treatment. Additionally, extensively drug-resistant *M. tuberculosis* (XDR TB) is characterized by resistance to both isoniazid and rifampin, plus any fluoroquinolone and at least one of three injectable second-line drugs (i.e., amikacin, kanamycin, or capreomycin).

The *M. tuberculosis* group has a number of members that include *Mycobacterium africanum*, *Mycobacterium bovis* (Dassie's *bacillus*), *Mycobacterium caprae*, *Mycobacterium microti*, *Mycobacterium mungi*, *Mycobacterium orygis*, and *Mycobacterium pinnipedii*. This group may also include the *Mycobacterium canettii* clade. The *M. canettii* clade includes *Mycobacterium prototuberculosis* and is a group of smooth-colony *Mycobacterium* species. Unlike the established members of the *M. tuberculosis* group, they undergo recombination with other species.

The established members of the *M. tuberculosis* complex are all clonal in their spread. The main human-infecting species have been classified into seven spoligotypes: type 1 contains the East African-Indian (EAI) and some Manu (Indian) strains; type 2 is the Beijing group; type 3 consists of the Central Asian (CAS) strains; type 4 of the Ghana and Haarlem (H/T), Latin America-Mediterranean (LAM) and X strains; types 5 and 6 correspond to *Mycobacterium africanum* and are observed predominantly and at very high frequency in West Africa. A seventh type has been isolated from the Horn of Africa. The other species of this complex belong to a number of spoligotypes and do not normally infect humans. Types 2 and 3 are more closely related to each other than to the other types. Types 5 and 6 are most closely aligned with the species that do not normally infect humans. Type 3 has been divided into two clades: CAS-Kili (found in Tanzania) and CAS-Delhi (found in India and Saudi Arabia).

The term "alkoxy" refers to a linear or branched oxy-containing functional group having an alkyl portion of one to about ten carbon atoms, such as a methoxy functional group, which may be substituted. In aspects of the disclosure an alkoxy functional group can comprise about 1-10, 1-8, 1-6 or 1-3 carbon atoms. In embodiments of the disclosure, an alkoxy functional group can comprise about 1-6 carbon atoms and includes a $C_1$-$C_6$ alkyl-O-group wherein $C_1$-$C_6$ alkyl has the meaning set out herein. Examples of alkoxy functional groups include without limitation methoxy, ethoxy, propoxy, butoxy, isopropoxy and tert-butoxy alkyls. An "alkoxy" functional group may, optionally, be substituted with one or more substituents disclosed herein including alkyl atoms to provide "alkylalkoxy" functional groups; halo atoms, such as fluoro, chloro or bromo, to provide "haloalkoxy" functional groups (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" functional groups (e.g. fluoromethoxymethyl, chloromethoxyethyl, trifluorornethoxymethyl, difluoromethoxyethyl, and trifluorocthoxymethyl.

The term "alkoxycarbonyl" as used herein refers to an alkyl-O—CO— group. Exemplary alkoxycarbonyl groups include methoxycarbonyl, ethoxycarbonyl, butyloxycarbonyl, and t-butyloxycarbonyl.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The terms "alkoxyl" or "alkoxyalkyl" as used herein refer to an alkyl-O— group wherein alkyl is as previously described. The term "alkoxyl" as used herein can refer to $C_{1\text{-}20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkyl", either alone or within other terms such as "thioalkyl" and "arylalkyl", as used herein, means a monovalent, saturated hydrocarbon functional group which may be a straight chain (i.e. linear) or a branched chain. An alkyl functional group for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl functional groups include methyl, ethyl, n-propyl, n-butyl, n-pentyl, n-hexyl, isopropyl, isobutyl, isopentyl, amyl, sec-butyl, tert-butyl, tert-pentyl, n-heptyl, n-actyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl functional group is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl functional group may be optionally substituted with substituents as defined herein at positions that do not significantly interfere with the preparation of compounds of the disclosure and do not significantly reduce the efficacy of the compounds. In certain aspects of the disclosure, an alkyl functional group is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

The term "alkylene" as used herein refers to a linear or branched functional group having from about 1 to 10, 1 to 8, 1 to 6, or 2 to 6 carbon atoms and having attachment points for two or more covalent bonds. Examples of such functional groups are methylene, ethylene, propylene, butylene, pentylene, hexylene, ethylidene, methylethylene, and isopropylidene. When an alkenylene functional group is present as a substituent on another functional group it is typically considered to be a single substituent rather than a functional group formed by two substituents.

The term "aralkoxycarbonyl" as used herein refers to an aralkyl-O—CO— group. An exemplary aralkoxycarbonyl group is benzyloxycarbonyl.

The term "aralkyl" as used herein refers to an aryl or a substituted aryl group bonded directly through an alkyl group, such as benzyl. Aralkyl groups include benzyl, phenylethyl, and naphthylmethyl. Other particular examples of substituted aryl functional groups include chlorobenzyl, and amino benzyl.

The term "aralkyloxyl" as used herein refers to an aralkyl-O— group wherein the aralkyl group is as previously described. An exemplary aralkyloxyl group is benzyloxyl.

The term "aroyl" as used herein refers to aryl functional groups, as defined above, attached to a carbonyl functional group as defined herein, including without limitation benzoyl and toluoyl. An aroyl functional group may be optionally substituted with groups as disclosed herein.

The term "aroylamino" as used herein refers to an aroyl-NH— group wherein aroyl is as previously described.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

The term "carbamoyl" as used herein refers to an $H_2N$—CO— group.

The term "carbonyl" as used herein refers to a carbon functional group having two of the four covalent bonds shared with an oxygen atom.

The term "carboxamide" as used herein refers to the group —CONH—.

The term "carboxyl" as used herein refers to the —COOH group.

The term "esterase-specific group" as used herein refers to a group that forms an ester with a detectable label such as a fluorophore (including but not limited to such as FITC (fluorescein isothiocyante). Certain fluorescent or absorbent dye labels may have low penetration into a target cell due to charged or other side-groups on the label. In the embodiments of the disclosure, esterification of a detectable label can advantageously increase the ability of the probe to penetrate into the cytosol of the targeted *mycobacterium* by modification of a side-group. Cleavage of the ester bond by an esterase releases the esterase-specific group from the fluorophore which is then able to more readily enter the cell. One example of an esterase-specific group that may be covalently attached to FITC and able to be released by an esterase is an acetoxymethyl (AM) group.

The group that is covalently attached to the fluorophore or dye by an esterase-cleavable ester bond may also function as a caging group that when attached to the detectable label reduces a detectable signal. Release of the attached group by esterase cleavage of the ester bond can then allow generation of the detectable signal such as a fluorescence emission.

The term "salt" as used herein refers to compounds that may be formed where acidic protons in the compounds are capable of reacting with inorganic or organic bases. Suitable inorganic salts include those formed with alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Suitable salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

Compounds of the disclosure which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

The compounds of the disclosure which are basic in nature can form a wide variety of different salts with various inorganic and organic acids. In practice is it desirable to first isolate a compound of the disclosure from a reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the disclosure are readily prepared by treating the base compound with a substantially equivalent amount of the chosen mineral or inorganic or organic acid in an aqueous solvent medium or in a suitable organic solvent such as methanol or ethanol. Upon careful evaporation of the solvent, the desired solid salt is obtained.

A composition of the disclosure may be sterilized by, for example, filtration through bacteria retaining filter, addition of sterilizing agents to the composition, irradiation of the composition, or heating the composition. Alternatively, the compounds or compositions of the present disclosure may be provided as sterile solid preparations e.g. lyophilized powder, which are readily dissolved in sterile solvent immediately prior to use.

A compound of the disclosure of the disclosure may be formulated into a pharmaceutical composition for administration to a subject by appropriate methods known in the art. Pharmaceutical compositions of the present disclosure or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, Remington: The Science and Practice of Pharmacy (21.sup.st Edition. 2005, University of the Sciences in Philadelphia (Editor), Mack Publishing Company), and in The United States Pharmacopeia: The National Formulary (USP 24 NF19) published in 1999. By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the chug components may be combined with any oral, non-toxic, pharmaceutically, acceptable inert carrier such as ethanol, glycerol, water, and the like. Suitable binders (e.g., gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

A compound of the disclosure includes derivatives. As used herein the term "derivative" of a compound of the disclosure can refer to a chemically modified compound wherein the chemical modification takes place either at a functional group or ring of the compound. The term "derivative" as used herein can further relate to a substitution of a functional group such as nitro group with another, different, group that is either functional or non-functional with respect to the intended use of the compound, or hydrogen. Non-limiting examples of derivatives of compounds of the disclosure may include N-acetyl, N-methyl, or N-hydroxy groups at any of the available nitrogen atoms in the compound.

A compound of the disclosure can contain one or more asymmetric centers and may give rise to enantiomers, diasteriomers, and other stereoisomeric forms which may be defined in terms of absolute stereochemistry as (R)- or (S)-. Thus, compounds of the disclosure include all possible diasteriomers and enantiomers as well as their racemic and optically pure forms. Optically active (R)- and (S)-isomers may be prepared using chiral synthons or chiral reagents, or resolved using conventional techniques. When a compound of the disclosure contains centers of geometric asymmetry, and unless specified otherwise, it is intended that the compounds include both E and A geometric isomers. All tautomeric forms are also included within the scope of a compound of the disclosure.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores(chromes) for the probes of the disclosure may be selected from, but not intended to be limited to, fluorescein isothiocyanate (FITC, green), cyanine dyes Cy2, Cy3, Cy3.5, Cy5, Cy5.5, Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE® Fluors (AnaSpec), and DYLITE® Fluors (Pierce, Inc).

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

The term "formulation" as used herein refers to a composition that may be a stock solution of the components, or a composition, preferably including a dilutant such as water or other pharmaceutically acceptable carrier or vehicle that may be available for distribution including to a patient or physician.

The term "halo" as used herein refers to a halogen such as fluorine, chlorine, bromine or iodine atoms.

The term "heteroaryl" as used herein refers to fully unsaturated heteroatom-containing ring-shaped aromatic functional groups having at least one heteroatom selected from carbon, nitrogen, sulfur and oxygen. A heteroaryl functional group may contain one, two or three rings and the rings may be attached in a pendant manner or may be fused. In aspects of the disclosure the term refers to fully unsaturated hetoreatom-containing ring-shaped aromatic functional groups having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" functional groups, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, benzimidazolyl, quinolyl, isoquinolyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl; purinyl, benzimidazolyl, quinolinyl, isoquinolinyl, beazotriazolyl, tetrazolopyridazinyl and the like; an unsaturated 3 to 6-membered heteromonocyclic group containing an oxygen atom, in particular, 2-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes functional groups where heterocyclic groups are fused with aryl groups, in particular bicyclic functional groups such as benzofuranyl, benzothiophenyl, phthalazinyl, chromenyl, xanthenyl, and the like. A heteroaryl functional group may be optionally substituted with groups as disclosed herein, for example with an alkyl, amino, halogen, etc., in particular a heteroarylamine. The term may refer to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, pyridinyl, pyrimidinyl, pyrazinyl, pyridazinyl, triazolyl, tetrazolyl and the like. A heteroaryl functional group may be optionally substituted with groups disclosed herein, for example with an alkyl, amino, halogen, etc., in particular a substituted heteroaryl functional group is a heteroarylamine.

The term "heterocyclic" as used herein refers to saturated and partially saturated heteroatom containing ring-shaped groups having at least one heteroatom selected from carbon, nitrogen, sulfur and oxygen. A heterocyclic group may contain one, two or three rings wherein such rings may be attached in a pendant manner or may be fused. In an aspect, the term refers to a saturated and partially saturated heteroatom-containing ring-shaped groups having from about 3 to 15, 3 to 10, 5 to 15, 5 to 10, or 3 to 8 ring members selected from carbon, nitrogen, sulfur and oxygen, wherein at least one ring atom is a heteroatom. Exemplary saturated heterocyclic groups include without limitation a saturated 3 to 6-membered heteromonocylic group containing 1 to 4 nitrogen atoms [e.g. pyrrolidinyl, imidazolidinyl, and piperazinyl]; a saturated 3 to 6-membered heteromonocyclic group containing 1 to 2 oxygen atoms and 1 to 3 nitrogen atoms [e.g. morpholinyl; sydnonyl]; and, a saturated 3 to 6-membered heteromonocyclic group containing 1 to 2 sulfur atoms and 1 to 3 nitrogen atoms [e.g., thiazolidinyl] etc. Examples of partially saturated heterocyclyl groups include without limitation dihydrothiophene, dihydropyranyl, dihydrofuranyl and dihydrothiazolyl. Illustrative heterocyclic groups include without limitation aziridinyl, azetidinyl, 2-pyrrolinyl, 3-pyrrolinyl, pyrrolidinyl, azepinyl, 1,3-dioxolanyl, 211-pyranyl, 4H-pyranyl, piperidinyl, 1,4-dioxanyl, morpholinyl, pyrazolinyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, quinuelidinyl, quinolizinyl, and the like.

The term "hydroxyalkyl" as used herein refers to an alkyl group substituted with an —OH group.

The term "hydroxyl" as used herein refers to the —OH group.

The term "fluorophore" as used herein refers to any reporter group (detectable label) whose presence can be detected by its fluorescent light emitting properties.

The term "lower-alkyl-substituted-amino" as used herein refers to any alkyl unit containing up to and including eight carbon atoms where one of the aliphatic hydrogen atoms is replaced by an amino group. Examples of such include, but are not limited to, ethylamino and the like.

The terms "carrier" and "vehicle" as used interchangeably herein refers to a medium which does not interfere with the effectiveness or activity of an active ingredient. A carrier or vehicle may include diluents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The term "substituted alkenyl" as used herein includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

The term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "substituted aryl" includes aryl groups, as defined herein, in which one or more atoms or functional groups of the aryl group are replaced with another atom or functional group including, for example, alkyl, substituted alkyl, halogen, aryl, substituted aryl, alkoxyl, hydroxyl, nitro, amino, alkylamino, dialkylamino, sulfate, and mercapto.

The term "substituted cycloaliphatic" as used herein refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyland the like.

The term "substituted aliphatic" as used herein refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like.

The term "thio" as used herein refers to a compound described previously herein wherein a carbon or oxygen atom is replaced by a sulfur atom.

The term "thiol" as used herein means —SH. A thiol may be substituted with a substituent disclosed herein, in particular alkyl (thioalkyl), aryl (thioaiyl), alkoxy (thioalkoxy) or carboxyl.

The term "thioalkoxy" as used herein, alone or in combination, refers to a chemical functional group where a sulfur atom (S) is bonded to an alkoxy group with the general chemical formula —$SR_{24}$ where $R_{24}$ is an alkoxy group which may be substituted. A "thioalkoxy group" may have 1-6 carbon atoms i.e. a —S—(O)—$C_1$-$C_6$ alkyl group wherein $C_1$-$C_6$ alkyl have the meaning as defined above. Illustrative examples of a straight or branched thioalkoxy group having from 1 to 6 carbon atoms, also known as a $C_1$-$C_6$ thioalkoxy, include thiomethoxy and thioethoxy.

The term "thioalkyl" as used herein, alone or in combination, refers to a chemical functional group where a sulfur atom (5) is bonded to an alkyl, which may be substituted. Examples of thioalkyl groups are thiomethyl, thioethyl, and thiopropyl. A thioalkyl may be substituted with a substituted or unsubstituted carboxyl, aryl, heterocylic, carbonyl, or heterocyclic.

The term "thioaryl" as used herein, alone or in combination, refers to a chemical functional group where a sulfur atom (S) is bonded to an aryl group with the general chemical formula —$SR_{23}$ where $R_{23}$ is aryl which may be substituted. Illustrative examples of thioaryl groups and substituted thioaryl groups are thiophenyl, chlorothiophenol, para-chlorothiophenol, thiobenzyl, 4-methoxy-thiophenyl, 4-nitro-thiophenyl, and para-nitrothiobenzyl.

A thiol may be substituted with a substituted or unsubstituted heteroaryl or heterocyclic, in particular a substituted or unsubstituted saturated 3 to 6-membered heteromonocylic group containing 1 to 4 nitrogen atoms [e.g. pyrrolidinyl, imidazolidinyl, piperidinyl, and piperazinyl] or a saturated 3 to 6-membered heteromonocyclic group containing 1 to 2 oxygen atoms and 1 to 3 nitrogen atoms [e.g. morpholinyl; sydrionyl], especially a substituted morpholinyl or piperidinyl.

Discussion

It has been reported that nitro-derivatives of benzothiazinones (such as BTZ043) or dinitro derivatives of benzamide (DNB) such as DNB1, as shown in FIG. 1, can act as potent antimycobacterial agents (Makarov et al., (2009) *Science* 324: 801-804; Ribeiro et al., (2011) *PLoS One* 6: 7; Trefzer et al., (2010) *J. Am. Chem. Soc.* 132: 13663-13665). Decaprenylphosphoryl-β-D-ribose 2'-epimerase (DprE1), an enzyme that is highly conserved in mycobacteria and required for the synthesis of the cell wall arabinans, was identified as the molecular target. The detailed mechanism involves the reduction of the nitro group or groups on such as BTZ043 and DNB1 to generate a nitroso derivative that can then specifically react with the cysteine residue found in the active site of DprE1.

The present disclosure provides novel probes, including embodiments of fluorophore- and dye-labeled probes for use in the specific imaging and detection of tuberculosis-associated mycobacteria species, and in particular those species or strains that are β-lactam-antibiotic resistant due to their having β-lactamase activity. The specificity for mycobacteria species is conferred on these probes by incorporating into the probes an activatable moiety that specifically targets the DprE1 found uniquely in in mycobacteria and thereby trapping the probe within the targeted mycobacyeria cell. Thus, those probes that combine a detectable label and a *mycobacterium*-specific DprE1-trapping moiety are advantageous for generally detecting mycobacteria in an isolated biofluid sample, a tissue, or in a whole human or animal body.

The probes of the disclosure may further comprise β-lactamase-substrate group covalently attached to the detectable label. Cleavage of the β-lactam ring of the β-lactamase substrate results in uncaging of the label with entry of the probe into the targeted mycobacteria, fixation of the *mycobacterium*-specific DprE1-trapping moiety of the probe to DprE1 and hence labeling of the mycobacterial cells. Accordingly, only mycobacteria species that express both a β-lactamase and DprE1 enable both the activation of the caged fluorescent probe, and the affixing of the released fluorescent probes to the bacteria cells through the functioning reduction-covalent binding mechanism. Advantageously, such a probe is able, at its most sensitive, to allow single colony-forming unit detection.

Figure 2:
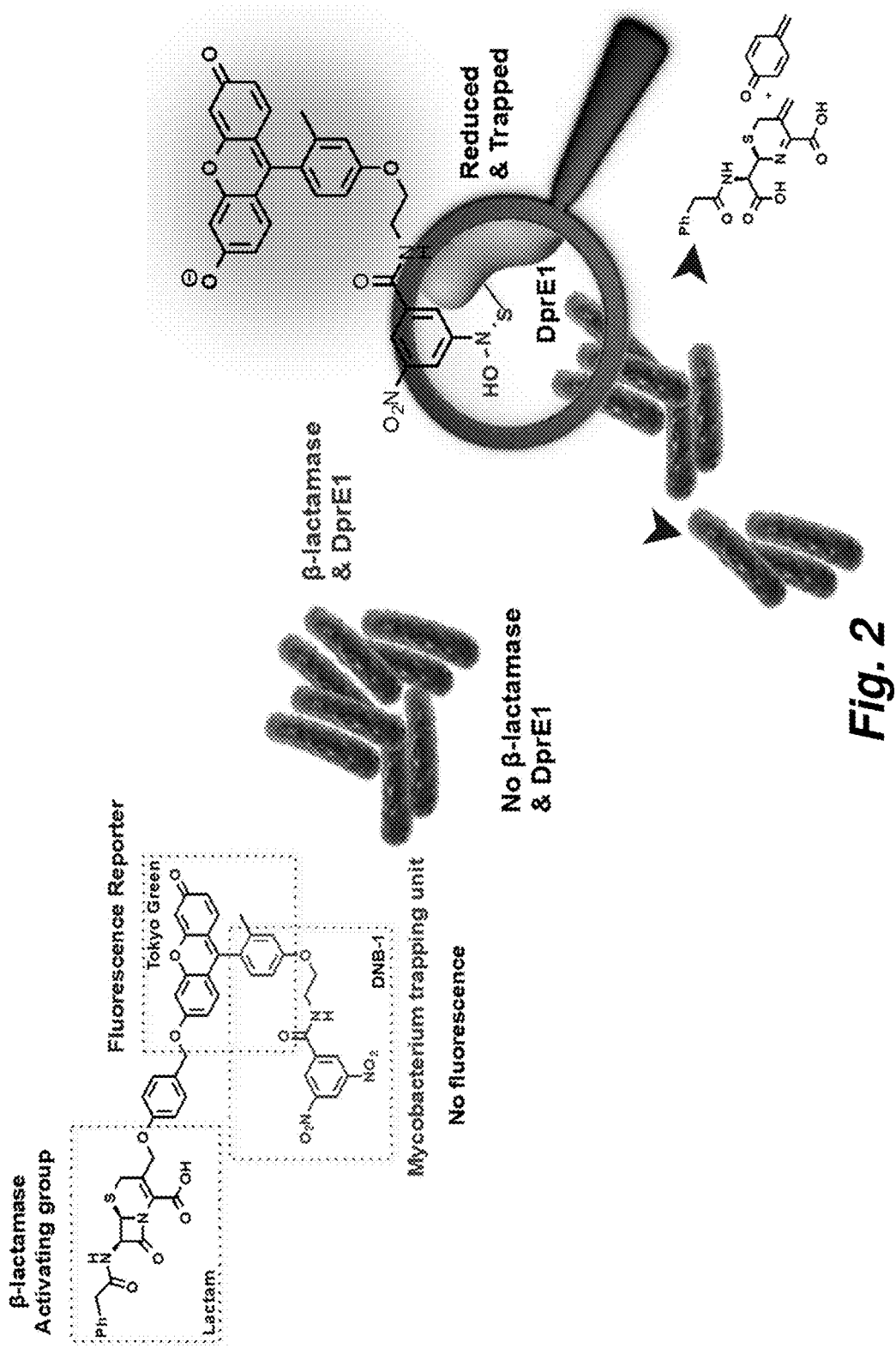
FIG. 2 illustrates the mechanism of the dual-targeting probes of the disclosure.

The probes of the disclosure are useful for the detection in both in vivo and in vitro samples of tuberculosis-associated mycobacteria species and can allow a determination of whether a patient has an infection thereof. The probes of the disclosure can further allow a diagnosis of an active infection or whether the patient, human or animal, has a latent colonization that is asymptomatic. This distinction can be useful, for example, to detect in a wild population of animals those hosts of *M. bovis* that could be transmitted to agricultural animals. Design of the dual-targeting fluorogenic probe: As schematically illustrated in FIG. 2, some embodiments of the probes of the disclosure can comprise a caged detectable label such as a fluorescent reporter or a dye that is conjugated to a β-lactamase substrate group and a DprE1-trapping moiety. The combined action of β-lactamase and the DprE1 enzyme results in the activation of the fluorescence reporter by its cleavage from the lactam followed by trapping of the conjugate detectable label:*mycobacterium*-specific DprE1-trapping moiety to the DprE1 enzyme, resulting in *mycobacterium*-specific labeling. For those bacteria that do not express β-lactamase activity, no label or probe binding will be observable. For those bacterial species or strains that do not express DprE1, the activated signal will not be retained by the bacteria.

Figure 3:
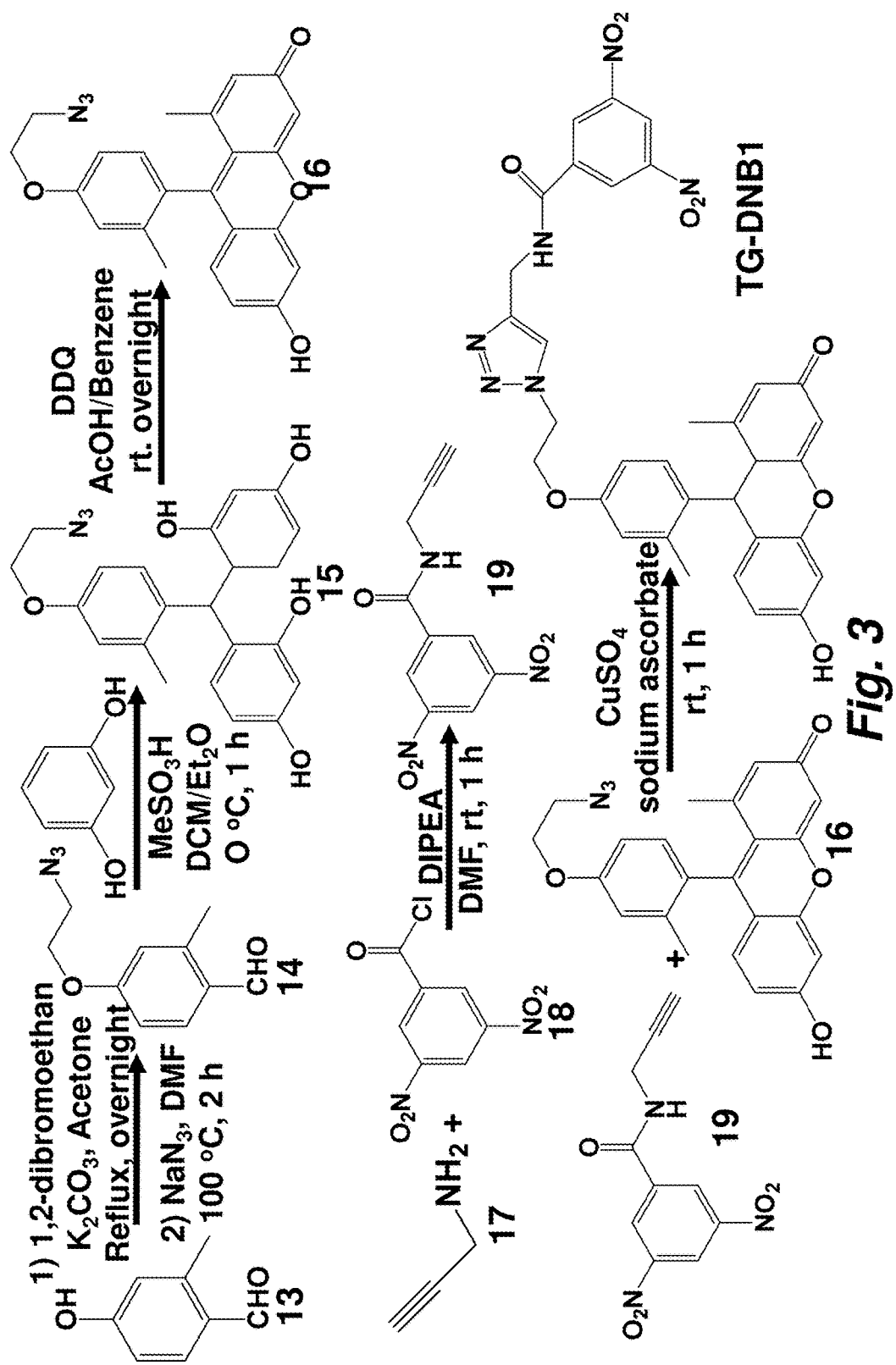
FIG. 3 illustrates a scheme for the synthesis of TG-DNB1.
Figure 4A:
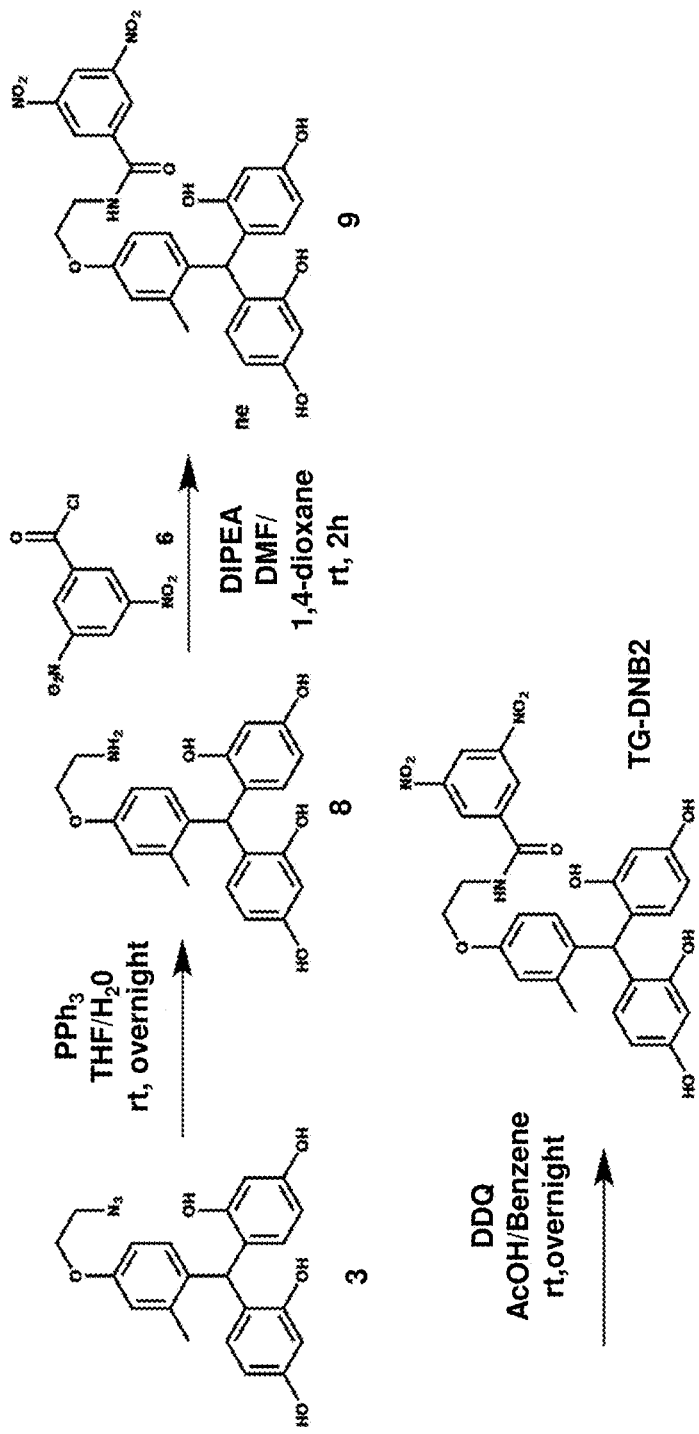
FIG. 4A illustrates a scheme for the synthesis of TG-DNB2. Synthesis of TG-DNB2 started with the reduction of the azide intermediate 3 by PPh$_3$, which afforded the amine analogue 8. Amidation of 8 with the dinitrobenzoyl chloride 6 obtained key intermediate 9, which was then followed by ring-closure reaction in the presence of DDQ to obtain the TG-DNB2.
Figure 4B:
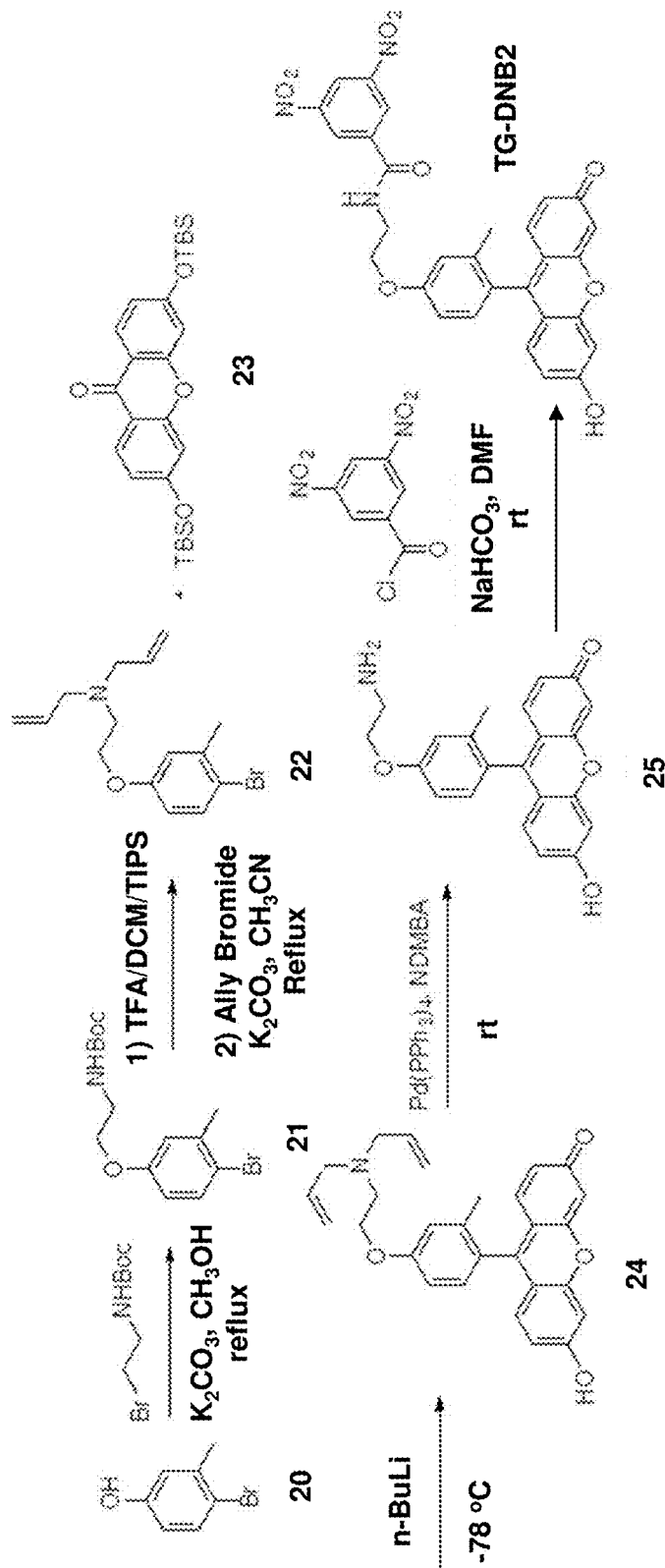
FIG. 4B illustrates an alternative scheme for the synthesis of TG-DNB2.
Figure 12:
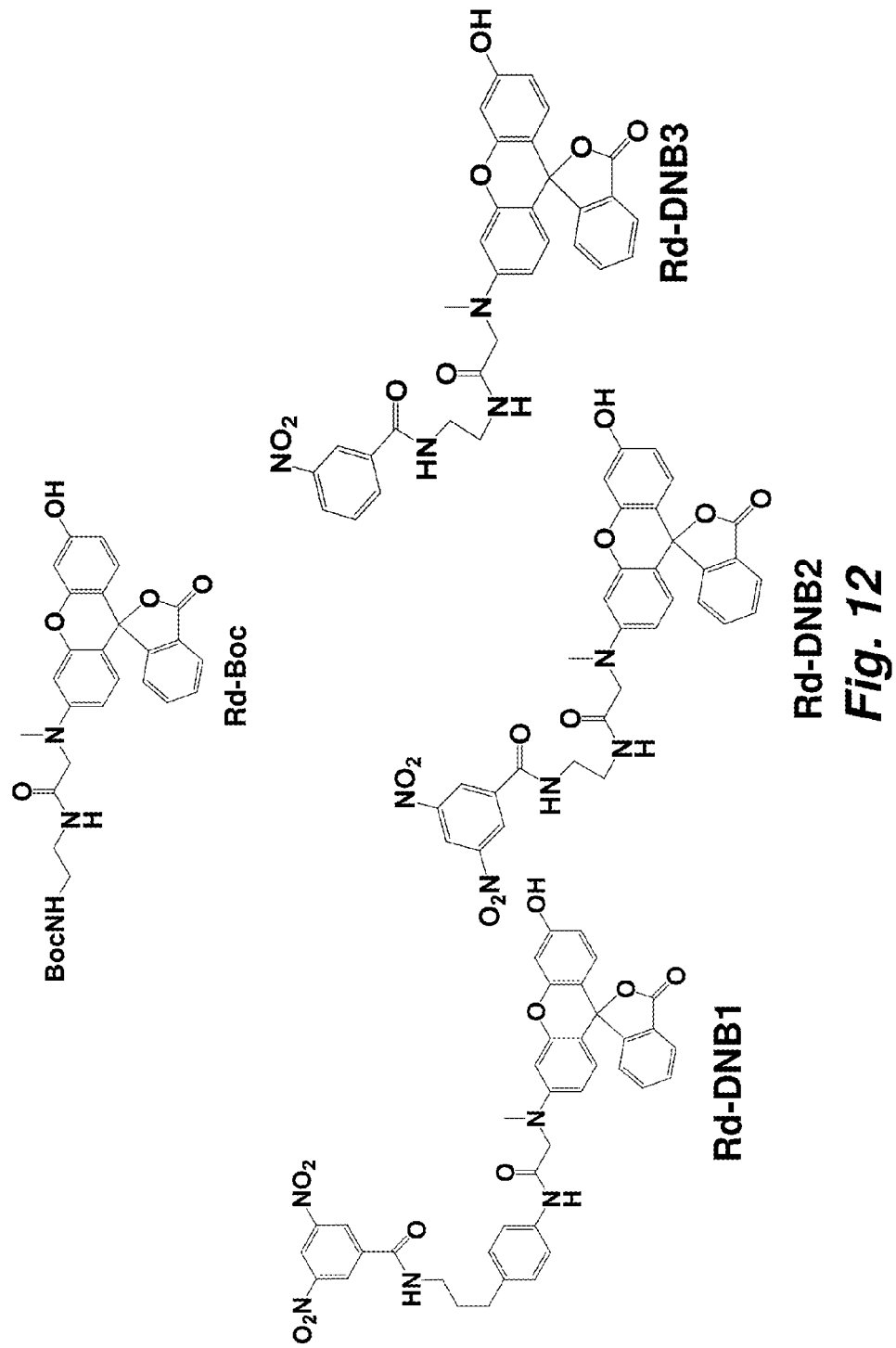
FIG. 12 illustrates the structures of Dye-DNB analogues.

Embodiments of the probes of the present disclosure may be provided as a free compound, or a derivative such as an ester or a salt. Enantiomeric and diastereomeric forms of the probe may also be usefully employed in the compositions and methods of the disclosure. It is further intended that the compositions of the disclosure may include the probe compound as a pure, or substantially pure, preparation thereof, or suspended or dissolved in a carrier or vehicle that is suitable for long-term or short-term stable storage. If in an isolated form not in contact with a carrier, such as a moisture-free amorphous or crystalline solid, it is intended that one of skill in the art will prepare a solution of the probe in a suitable carrier or vehicle before its use to detect a population of mycobacteria cells. Accordingly, the term composition as used herein is intended to include the isolated probe or derivative, or a solution or suspension thereof in a liquid carrier o vehicle. DprE1 as the target for *mycobacterium* labeling: To show that detectable label-DNB conjugate analogues can be reduced and form a covalent bond with DprE1, which is only expressed in mycobacteria, a series of DNB-dye conjugates were designed and synthesized, including three Rhodol-DNB (Rd-DNB) analogues, one Rhodol-Boc-blocked (Rd-Boc) as a control compound, three FITC-DNB analogues and their AM-esterified derivatives, and two TG-DNB analogues, as shown in FIG. 12. DprE1 is the target for *mycobacterium*-specific labeling: The TG-DNB (Tokyo Green-dinitro derivative of benzamide) analogues TG-DNB1 and TG-DNB2, as shown in FIG. 12, were synthesized to examine the mechanism of trapping a probe of the disclosure by DprE1 expressed in mycobacteria. As shown in FIG. 3, the synthesis of TG-DNB1 started with a substitution reaction of 4-hydroxy-2-methylbenzaldehyde 1 to obtain the azido-derivative 2. Condensation with resorcinol afforded 3, followed by ring-closure reaction in the presence of DDQ to obtain key intermediate 4. A copper-catalyzed click reaction of 4 with dinitro-benzoyl alkyne 7, which was obtained from dinitrobenzoyl chloride 6, resulted in the analogue TG-DNB1. Schema for the synthesis of the TG-DNB2 analogue are shown in FIGS. 4A and 4B.

Figure 6A:
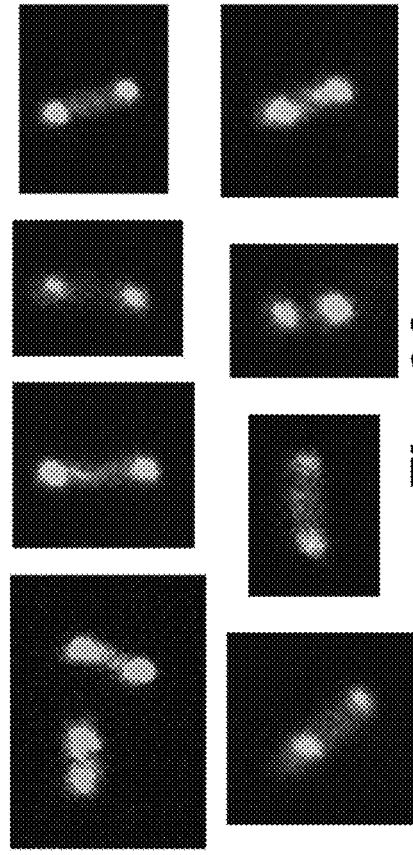
FIG. 6A is a series of confocal images. *M. smegmatis* was incubated with 10 μM of TG-DNB2 at room temperature for 1 h. Cells were washed 3 times with PBS, fixed in 10% formalin solution for 30 min before being visualized with a confocal microscope under 63x/oil, Ex/Em-FITC. Images show a polarized localization of green fluorescence.
Figure 6B:
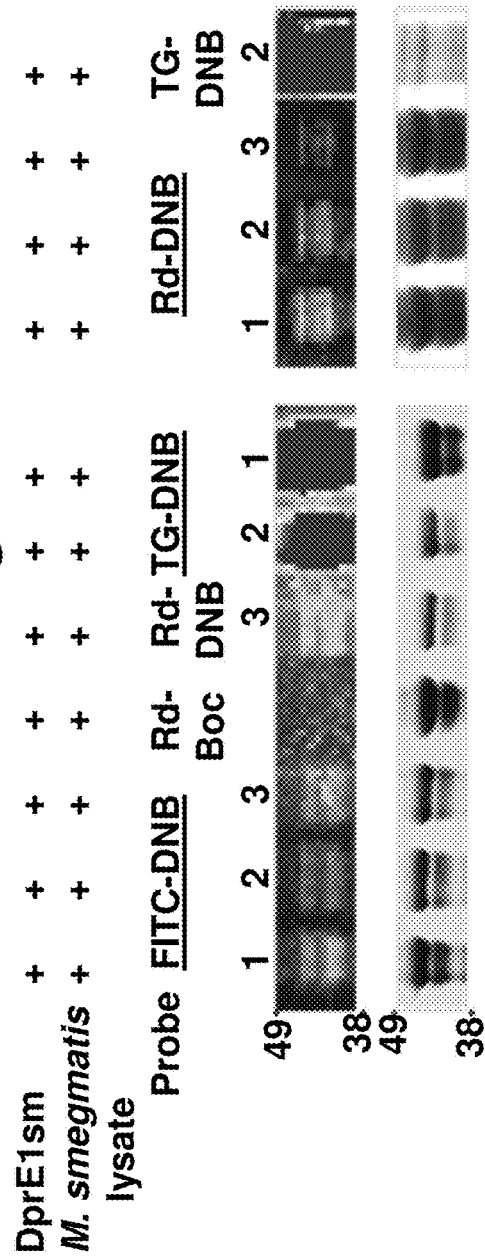
FIG. 6B illustrates fluorescence labeling of DprE1 by FITC-DNB, Rhodol-DNB and TG-DNB analogues (10 μM).
Figure 6C:
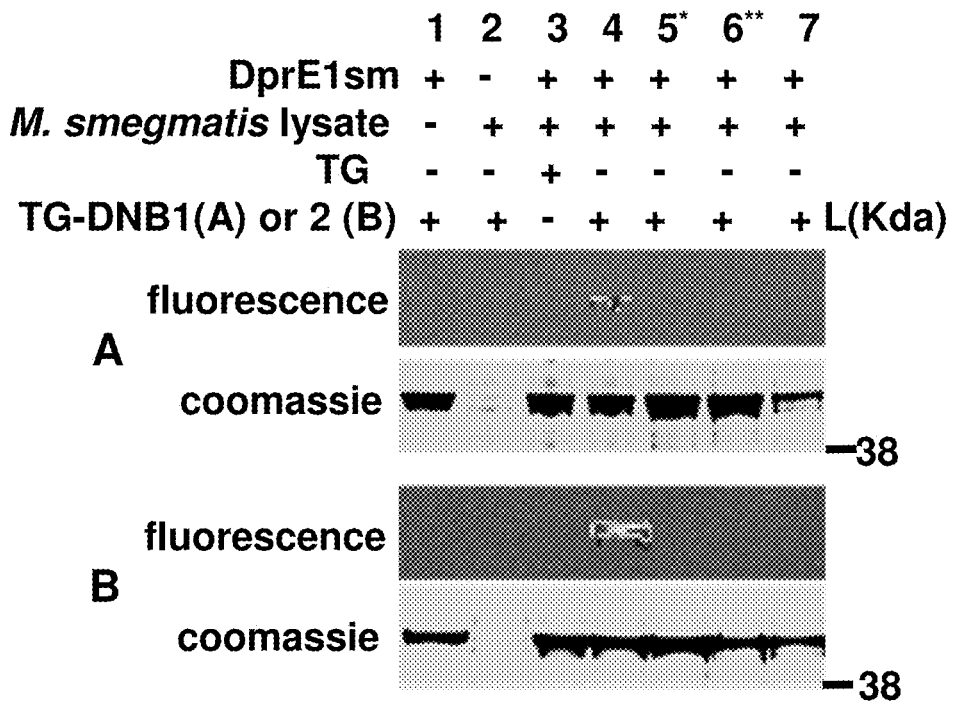
FIG. 6C illustrates fluorescence labeling of DprE1$_{SM}$ by TG-DNB1 and TG-DNB2 (10 μM). Lane 5*: DprE1$_{SM}$ was pre-treated in 1% SDS. Lane 6**: sample buffer was adjusted to 7 M urea and 20 mM DTT after incubation. These samples were further incubated for one hour at 37° C. Lane 7: DprE1$_{SM}$ was incubated with 50 μM DNB1 for one hour prior to addition of TG-DNB1. Experiments were repeated twice to show similar results.

Full-length *M. smegmatis* DprE1 protein was expressed and purified from an *E. coli* expression system. Whole cell lysate of *M. smegmatis* was prepared to provide decaprenylphosphoryl-β-D-ribofuranose (DPR) as substrate required for the reaction. As shown in FIG. 6B, all of the labeled DNB analogues could covalently label DprE1 protein in the presence of lysate. TG-DNB1 and TG-DNB2 exhibited significantly higher labeling capability than did the two mononitro compounds FITC-DNB2 and Rd-DNB3.

The TG-DNB analogues were further tested with a commonly used laboratory *mycobacterium* strain *Mycobacterium smegamatis* (*M. smegmatis*). *E. coli* strain TOP10, *Streptococcus* strains *S. pneumoniae* and *S. sanguinis*, *Staphylococcus aureus*, *Corynebacteria propinquum* and *C. striatum* were used as controls. *S. pneumoniae* and *S. aureus* are frequently found in the human respiratory tract and the skin (van der Poll & Opal (2009) *Lancet* 374:1543-1556; Cole et al., (2001) *Clin. Diagn. Lab. Immunol.* 8:1064-1069). *Corynebacteria* commonly colonize the skin and mucous membranes of human (Watkins et al., (1993) *Clin. Infect. Dis.* 17:21-25). *S. sanguinis* is a normal inhabitant of the human mouth where it is often found in saliva (Paik et al., (2005) *Infect. Immun.* 73(9):6064-6074). Among these control strains, *E. coli* is gram negative, all the other strains are gram positive with a thick cell wall.

Figure 5A:
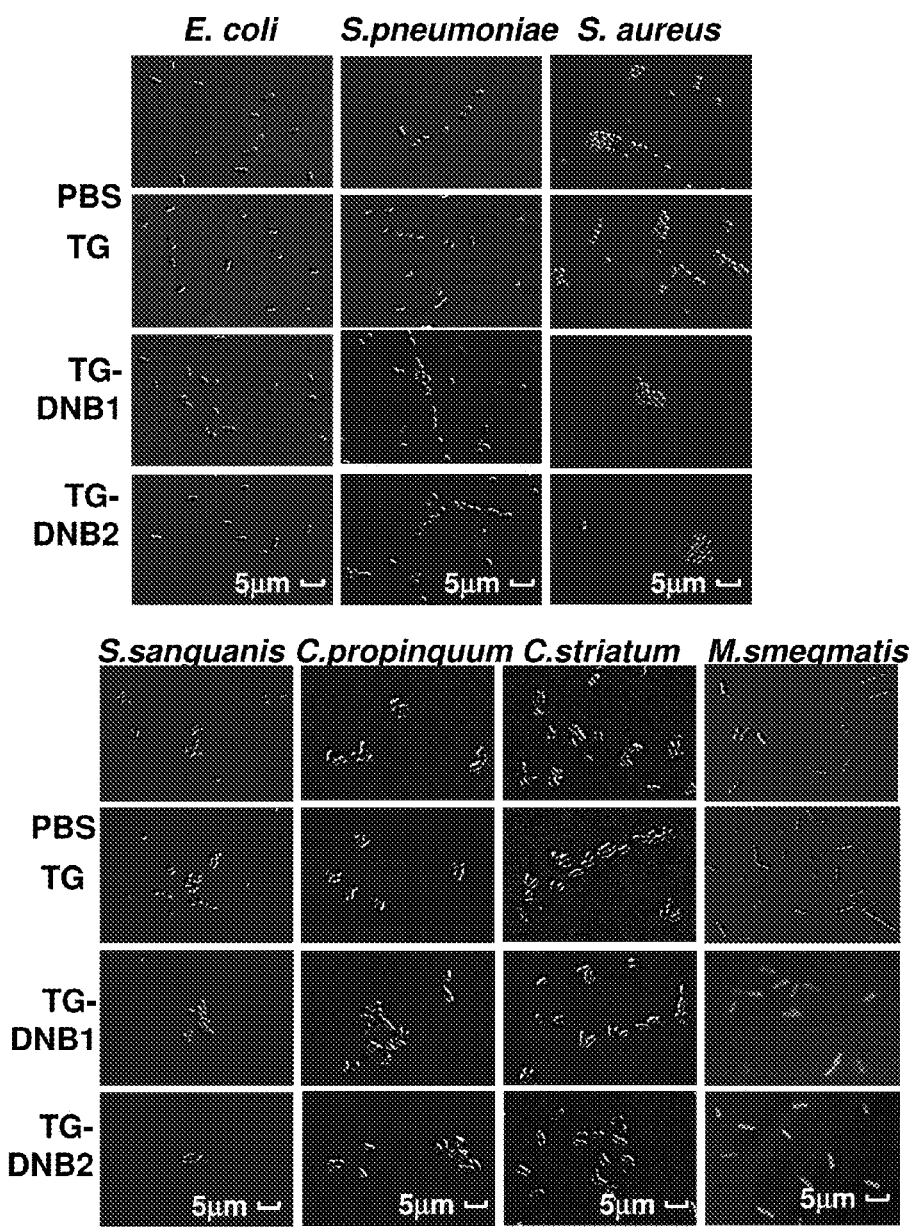
FIGS. 5A-5C illustrate freshly cultured *E. coli* (TOP10), *S. pneumoniae*, *S. aureus*, *S. sanguinis*, *C. propinquum*, *C. striatum* and *M. smegmatis* were incubated with PBS, 10 μM of TG, TG-DNB1 or TG-DNB2 at room temperature for 1 h. Cells were washed stringently with PBS for 3 times then fixed in 10% formalin solution for 30 min before vizualized with a confocal microscope (63x/oil, Ex/Em-FITC).
Figure 5B:
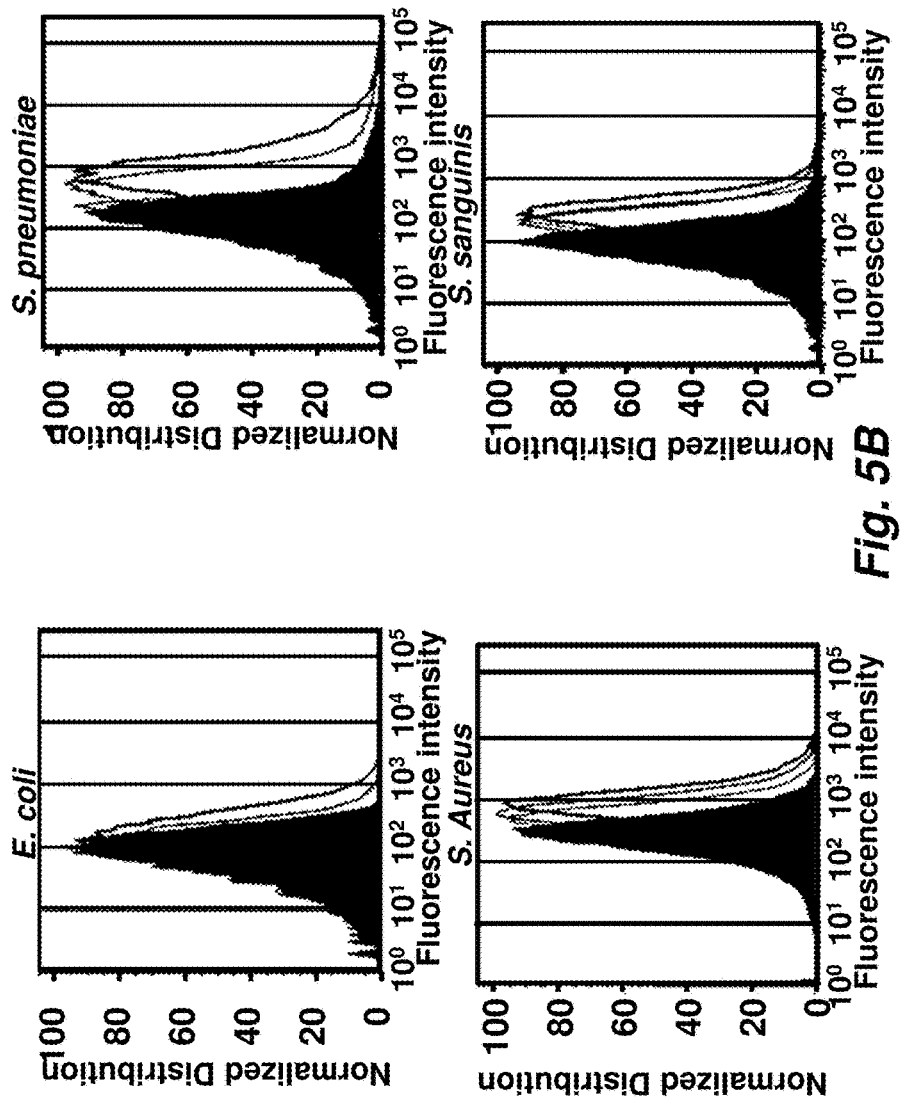

As shown in the confocal images of FIG. 5A, both TG-DNB1 and TG-DNB2, compared to other probes, exhibited much higher fluorescence labeling of *M. smegmatis* than of control strains. Neither the solvent PBS (phosphate-buffered saline) nor the Tokyo Green (TG) fluorophore alone showed any fluorescence staining of *M. smegmatis*.

Figure 5C:
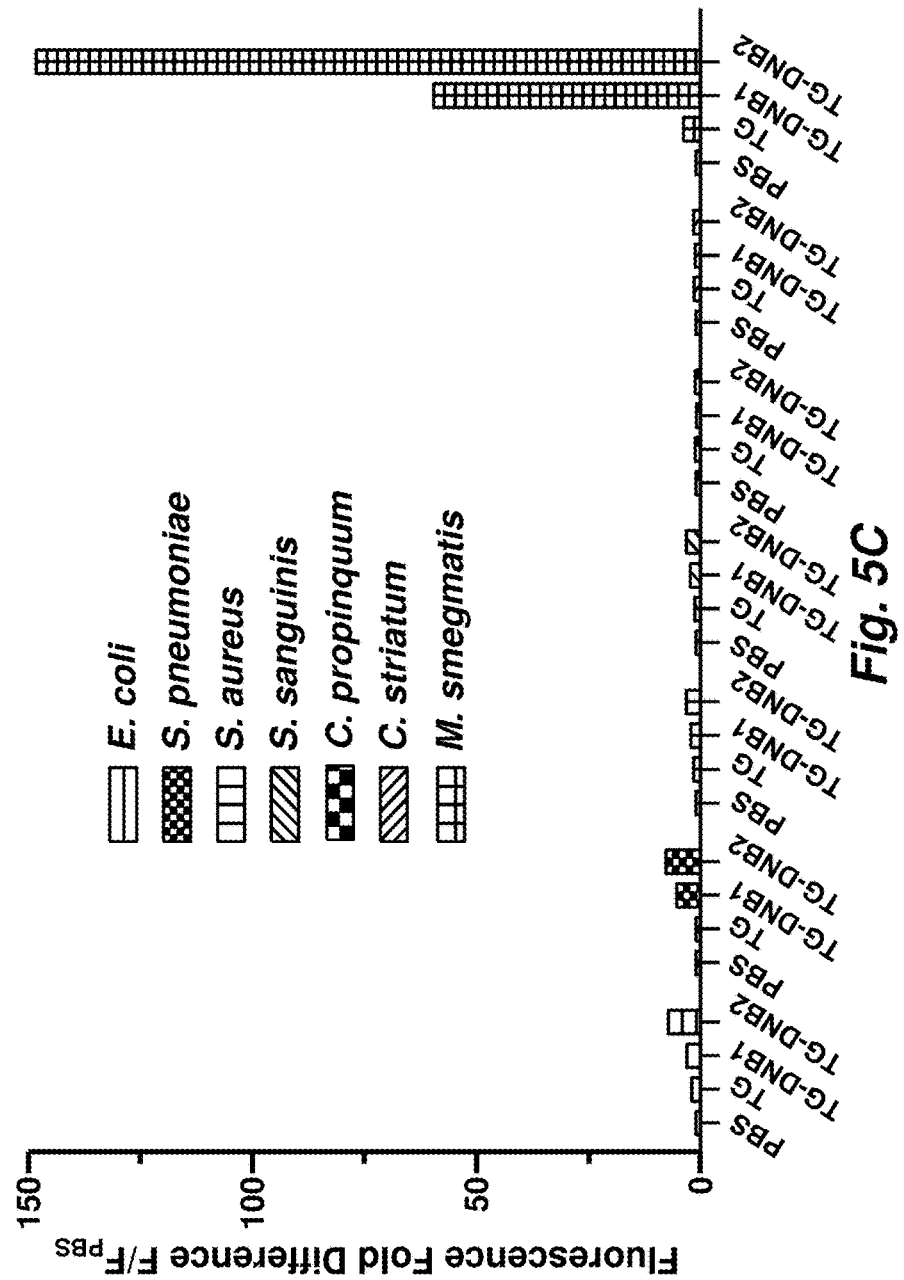

The treated bacteria were further analyzed with flow cytometry, revealing that *M. smegmatis* incubated with TG-DNB2 showed 150-fold higher fluorescence intensity than when incubated with PBS. TG-DNB1 also led to a 50-fold fluorescence increase in *M. smegmatis* in comparison to PBS treatment (FIG. 5C). Negligible signal trapping was observed for the fluorophore alone. The trapped fluorescence signal in *M. smegmatis* was observed mostly at the polar regions, which is consistent with literature reports that DprE1 is expressed and located predominantly within each pole of the bacteria (FIG. 6A).

Figure 6D:
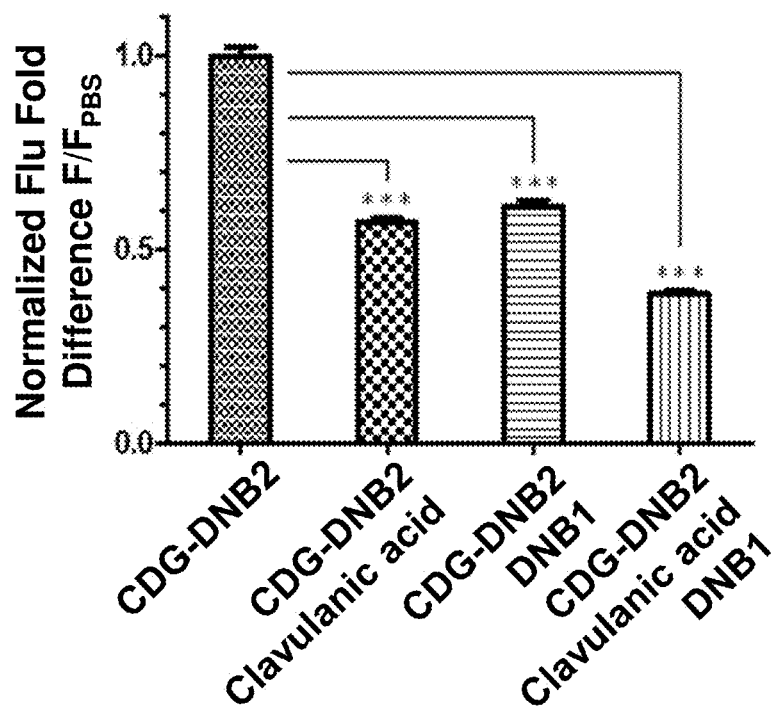
FIG. 6D is a graph illustrating dual-targeting as evidenced by treating *M. smegmatis* with the BlaC inhibitor clavulanic acid, and DNB1. GraphPad Prism 5 software was utilized for statistical analysis. The significant difference was determined by performing one-way ANOVA followed by post hoc Bonferroni's multiple comparison test to determine the statistical significance with 95% confidence intervals with *p<0.05; p<0.01, *p<0.001 and ns, not significant (p>0.05). All error bars in figure represent ±SD, n=3.
Figure 7:
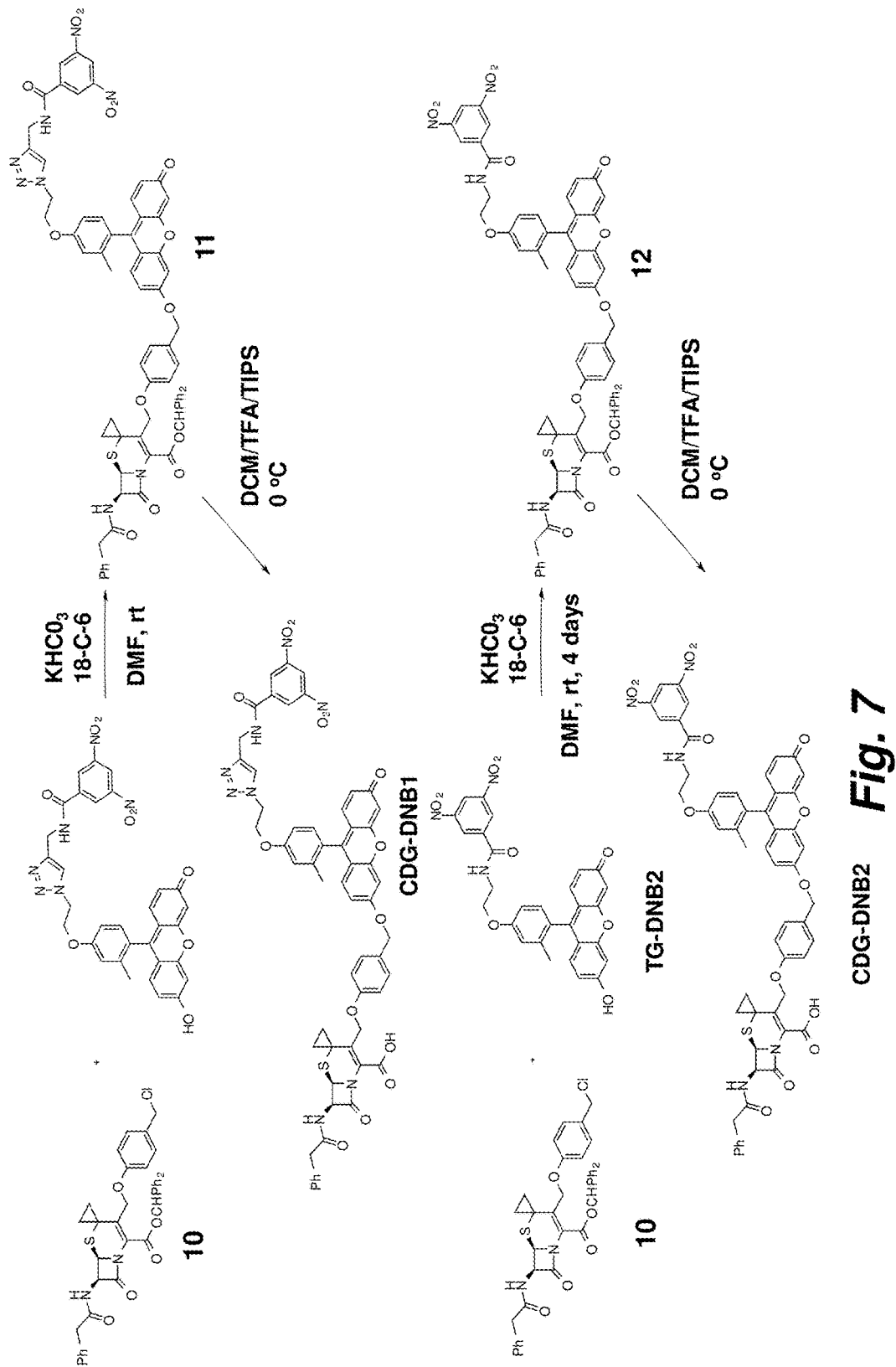
FIG. 7 schematically illustrates the synthesis of CDG-DNB1 and CDG-DNB2.
Figure 16:
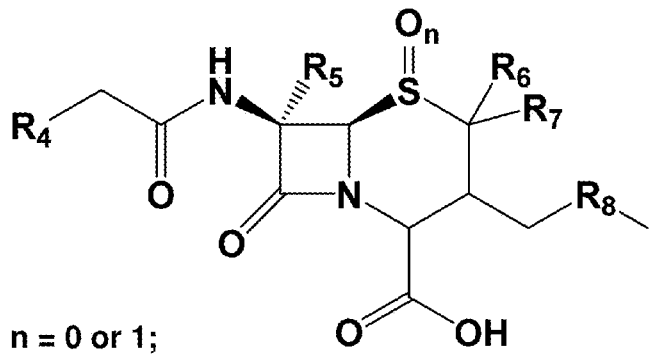
FIG. 16 illustrates β-lactamase substrate group and derivatives thereof suitable for incorporation into embodiments of the probes of the disclosure.
Figure 19:
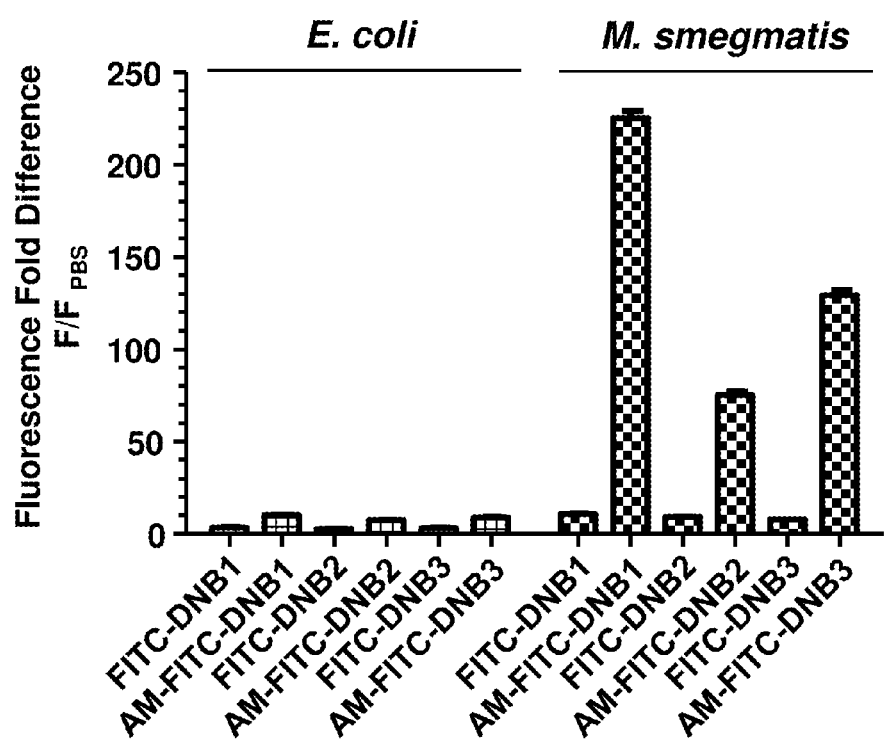
FIG. 19 is a graph illustrating *E. coli* and *M. smegmatis* treatment with FITC-DNB or AM-FITC-DNB analogues and then analyzed by flow cytometry. Data was analyzed by Graph Pad Prism 5.

To further validate the covalent labeling of DprE1 with TG-DNB1 and TG-DNB2, a labeling assay with multiple controls was performed. As shown in FIG. 6B, a fluorescent band was observed when both TG-DNB analogues and the lysate were present in the reaction. The lack of the lysate (and thus of the substrate Decaprenylphosphoryl-β-D-ribofuranose (DPR)) or pre-incubation with DNB1 alone abolished the band, as shown in FIG. 6O, lanes 1 and 7. DTT/8M urea denaturing conditions could reverse the formed adduct (FIG. 6O, lane 6), consistent with previous reports. An inhibitor study with clavulanic acid and DNB1 in *M. smegmatis* further evidenced the mechanism of dual targeting, as shown in FIG. 6D. Targeting DprE1 with FITC Probes: Three FITC-DNB analogues, as shown in FIG. 12, have been prepared for the evaluation of their use of targeting DprE1. They displayed very low activity in both *E. coli* (without the DprE1) and *M. smegmatis* (with the presence of DprE1). However, when the fluorphore FITC was converted to acetyloxymethyl ester (FIG. 14) to afford AM-FITC-DNB1, AM-FITC-DNB2, and AM-FITC-DNB3, *M. smegmatis* showed significantly enhanced fluorescence intensity (over 100-fold relative to the control, as shown in FIG. 19), suggesting that the AM analogs have better cell permeability for mycobacteria due to the elimination of the negative charges of FITC. This series of compounds can advantageously allow the combination of targeting esterase and DprE1 to enhance the *mycobacterium* labeling when the employed fluorphore possesses poor cell permeability due to the presence of charged groups or other polar groups. Dual-targeting of Bla and DprE1 in the *mycobacterium M. smegmatis*: The dual-targeting probes CDG-DNB1 and CDG-DNB2 were synthesized by conjugating TG-DNB with a lactam unit for the specific detection of β-lactam antibiotic-resistant mycobacteria, as shown schematically in FIG. 7.

β-Lactams suitable for use in the probes of the disclosure include cephalosporins as described, for example, in U.S. Patent Application Publication No. US2015/0219653 and PCT application Publication No. WO2015/109056. Embodiments of the probes of the disclosure can further include variations of the β-lactamase-substrate moiety, such as shown in FIG. 16. For example, but not intended to be limiting, it has been found that a methoxy substitution to the lactam ring results in a greater specificity for *Mycobacterium tuberculosis* BlaC.

Figure 11:
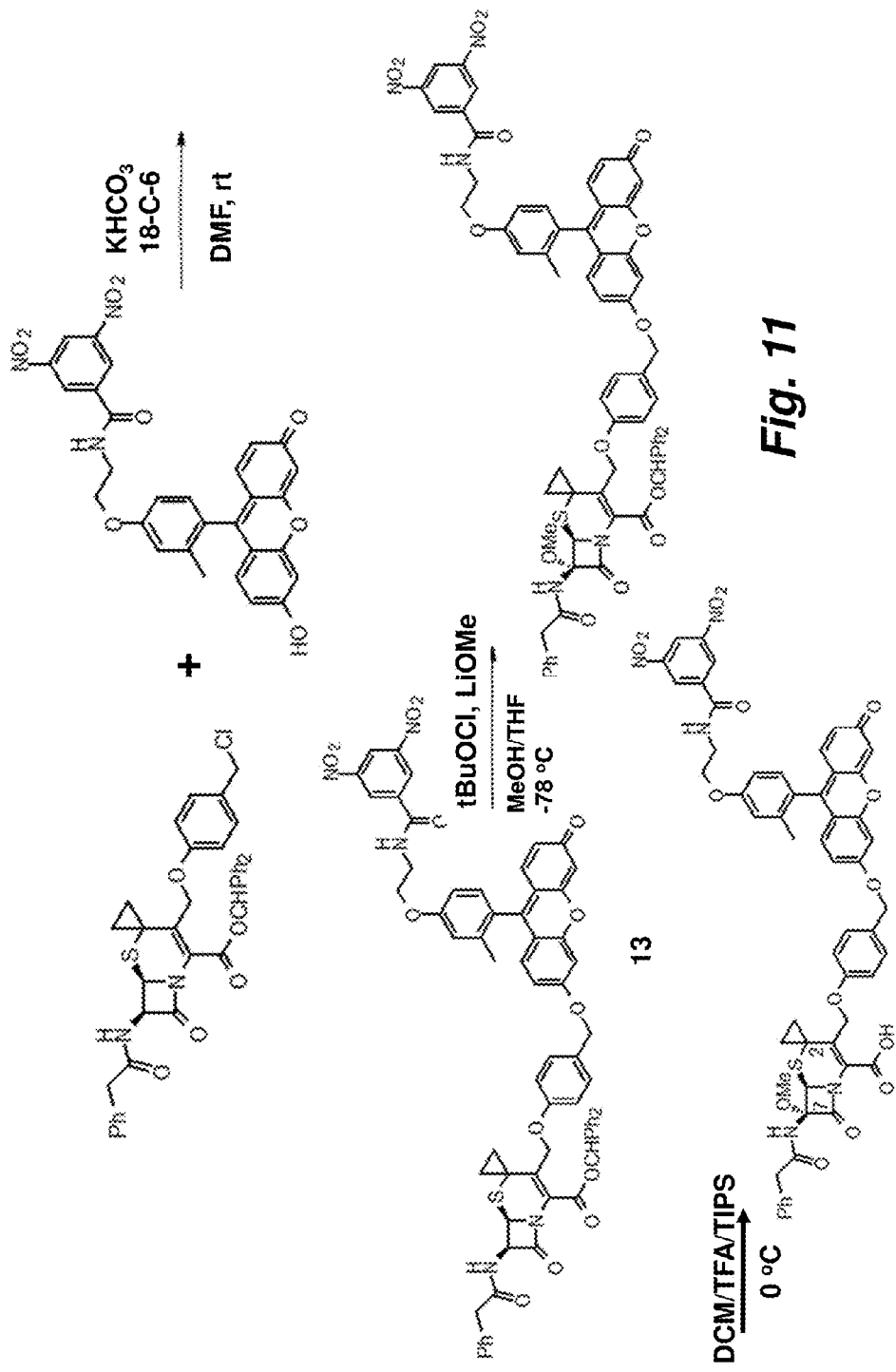
FIG. 11 schematically illustrates the synthesis of CDG-DNB3.

The β-lactamase substrate may be covalently attached directly to the detectable label or by the inclusion of the intervening linker, resulting in, for example, a BlaC-specific dual-targeting probe such as CDG-DNB3, the synthesis of which is shown in FIG. 11, and which can be usefully employed for the specific imaging and detection of MTBC.

The probes of the disclosure may be in free solution, or tethered to a solid support for contact with a test sample. Such methods of tethering the probes to such supports as well as the detection system selected and/or adapted for the detection of the released labelling moiety are well-known in the art.

A substitution reaction with a previously reported lactam intermediate 10, followed by deprotection, had resulted in the dual-targeting probes CDG-DNB1 and CDG-DNB2. Both of these probes, together with CDG-1 (shown in FIG. 1) were tested for imaging *M. smegmatis* and control strains. As shown in the confocal microscope images of FIG. 8A, both CDG-DNB1- and CDG-DNB2-treated *M. smegmatis* yielded intense fluorescence signals compared to control bacterial strains.

Figure 8A:
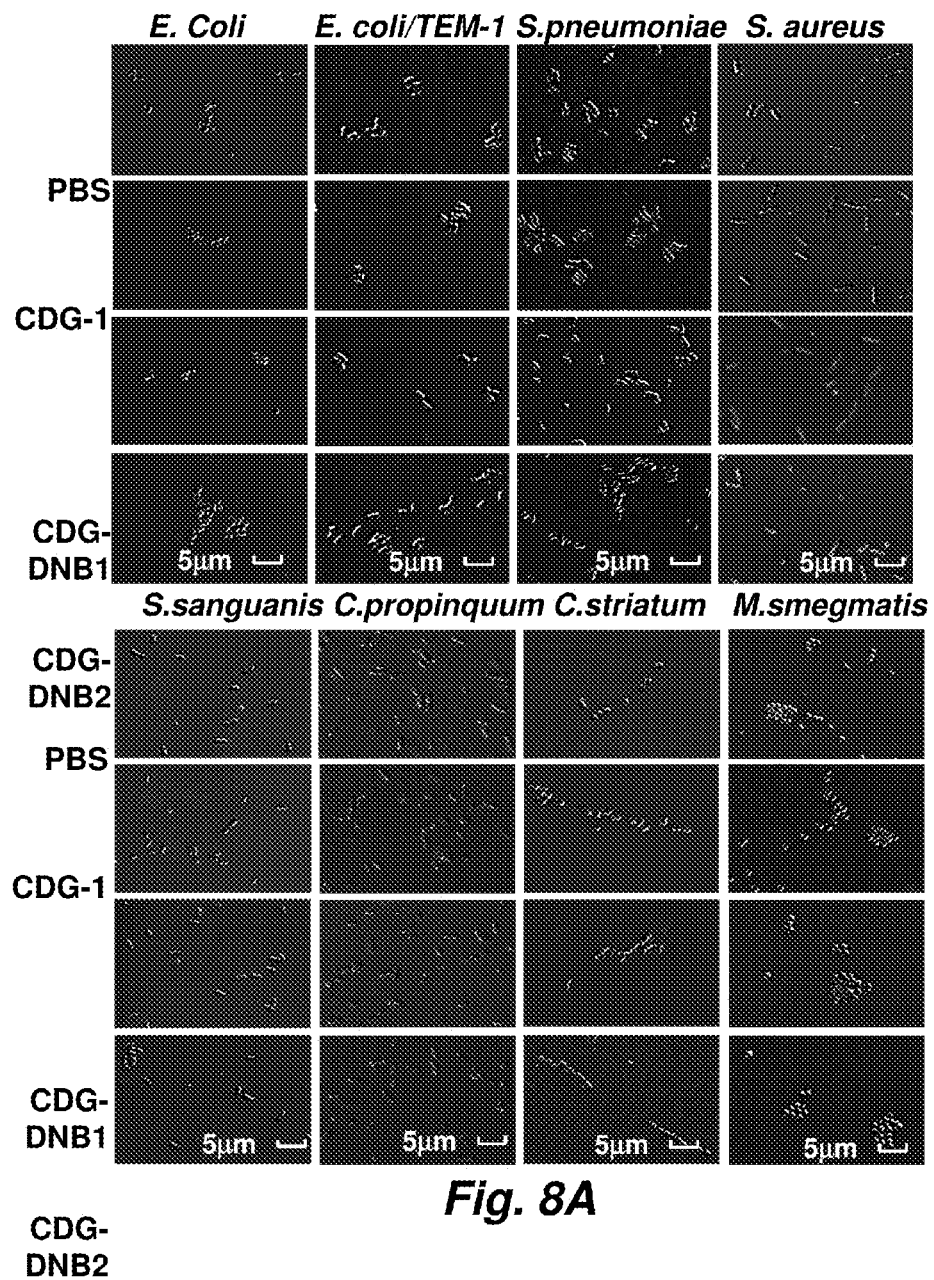
FIG. 8A is a series of digital overlay images. Freshly cultured *E. coli* (TOP10), *E. coli* expressing TEM1-β-lactamase, *S. pneumoniae*, *S. aureus*, *S. sanguinis*, *C. propinquum*, *C. striatum*, and *M. smegmatis* were incubated with PBS, 10 μM CDG1, CDG-DNB1, or CDG-DNB2 at room temperature for 1 h. Cells were washed 3 times PBS and then fixed in 10% formalin solution for 30 min before analyzed with a confocal microscope under 63x/oil, Ex/Em-FITC. Images show an overlap of bright field and green fluorescence.
Figure 8B:
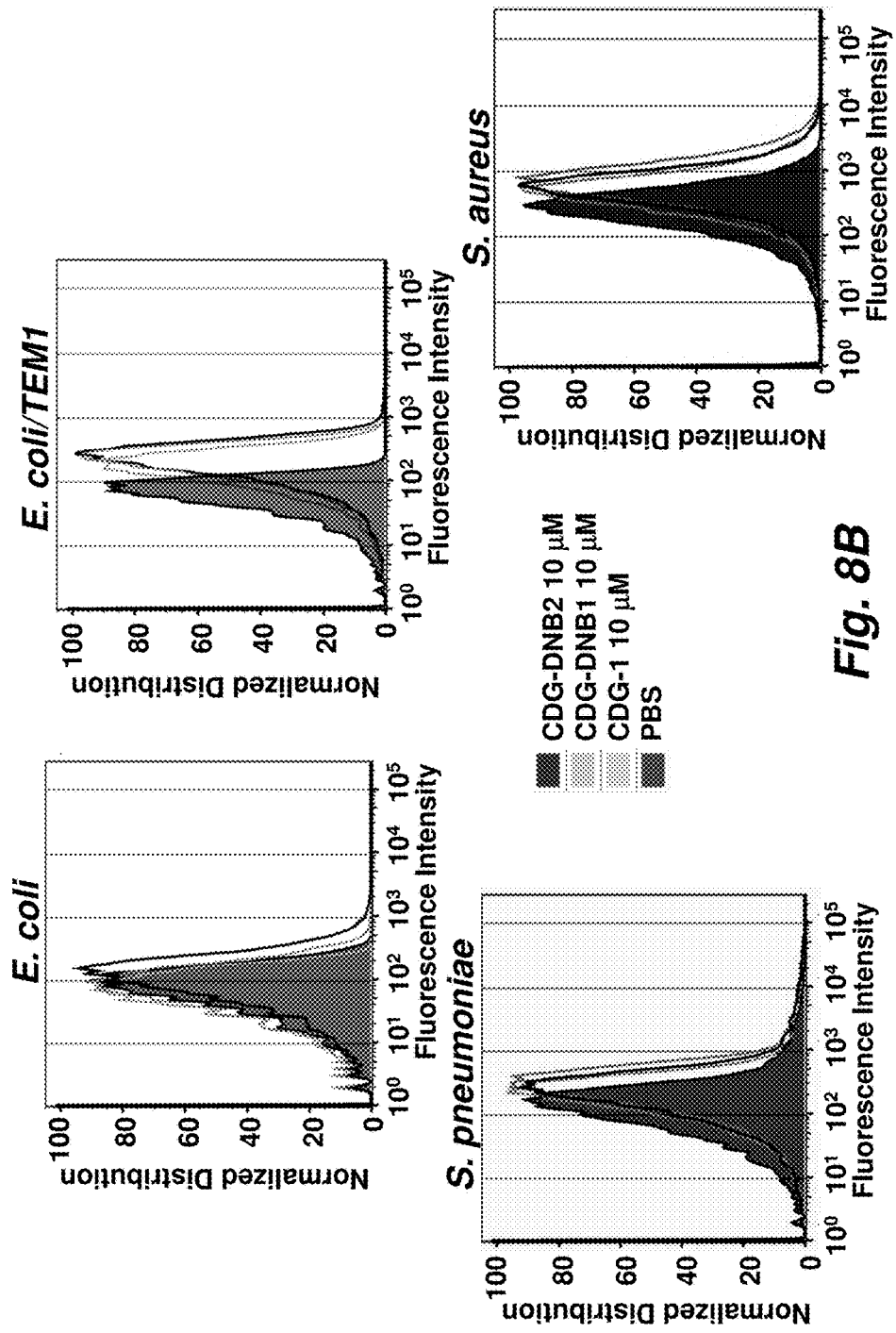
FIG. 8B illustrates a series of histograms of fluorescence-activated flow cytometry.
Figure 8D:
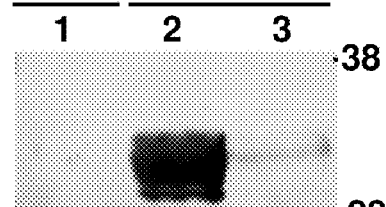
FIG. 8D is a digital image of a Western blot showing the expression of TEM1 β-lactamase induced by 1 mM IPTG in transformed TOP10 lysate (lane 2). Lane 1 shows the wild type TOP10 lysate; Lane 3 shows the transformed TOP10 lysate without IPTG induction. 150 μg lysate was loaded per lane. Experiments were repeated twice and showed similar results.

Without inclusion of the DprE-1-targeting group, CDG-1 can only be hydrolyzed by the β-lactamase BlaS expressed in *M. smegmatis*. However, the resulting released (uncaged) fluorophore cannot be trapped in or on the cells. PBS showed no fluorescence background (FIG. 8A, top row of images). The confocal images were further quantitated with flow cytometry (as shown in FIG. 8B) that revealed that CDG-DNB2 produced an 80-fold increase in the fluorescence intensity compared to PBS treatment. Consistent with the TG-DNB analogues, CDG-DNB1 showed half of the intensity of CDG-DNB2 due to its lower trapping capability, as shown in FIG. 8B. *E. coli* transformed with TEM1 β-lactamase (FIG. 8D) can hydrolyze CDG-DNB2 and generate the uncaged fluorescent signal (FIG. 8C), but cannot retain the fluorescence due to the lack of the DprE1 enzyme in this bacterial species. Dual-targeting of BlaC and DprE1 in BCG and H37Rv: To estimate whether CDG-DNB2 can be utilized for the diagnosis of pathogenic mycobacteria, *Bacillus* Calmette-Guérin (BCG) and *Mycobacterium tuberculosis* (H37Rv), were tested. BCG is a vaccine prepared from the live bovine tuberculosis *bacillus Mycobacterium bovis*. It is widely used as an attenuated tuberculosis model due to its high similarity to human *Mycobacterium tuberculosis*. H37Rv is a typical strain of human *Mycobacterium tuberculosis* and expresses both β-lactamase BlaC and DprE1. The well documented history, world-wide distribution, and extensive use of H37Rv by mycobacteriologists make this strain especially useful as a test strain for studying the properties of the probes of the disclosure.

Figure 9A:
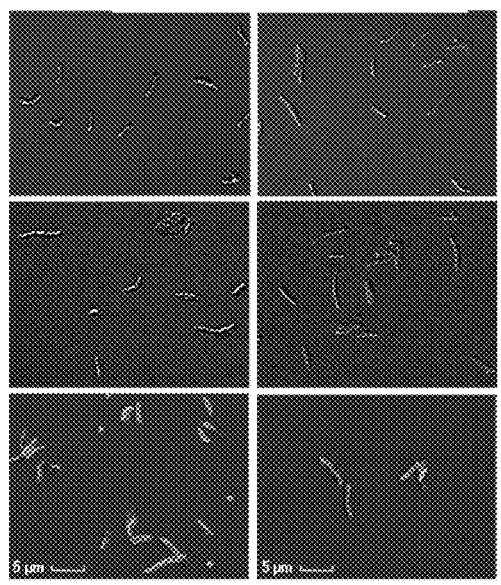
FIG. 9A is a series of images showing an overlap of bright field and green fluorescence. Freshly cultured BCG and *Mycobacterium tuberculosis* H37Rv were incubated with PBS, 10 μM CDG-1, or CDG-DNB2 at room temperature for 1 h. Cells were washed 3 times with PBS and then fixed in 10% formalin solution for 30 min before analyzed with a confocal microscope under 63x/oil, Ex/Em-FITC.
Figure 9B:
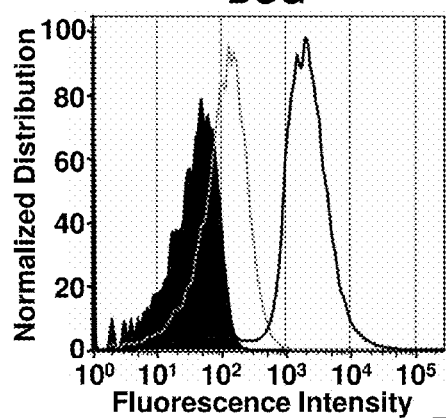
FIG. 9B illustrates a pair of histograms of fluorescence-activated flow cytometry.
Figure 9B:
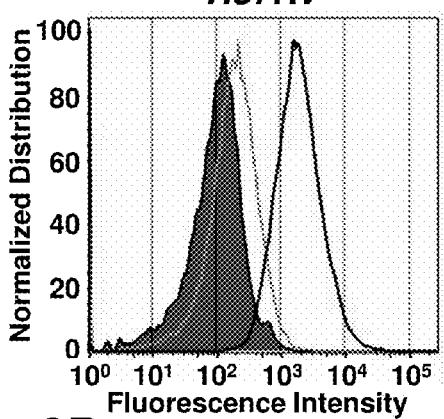
Figure 9C:
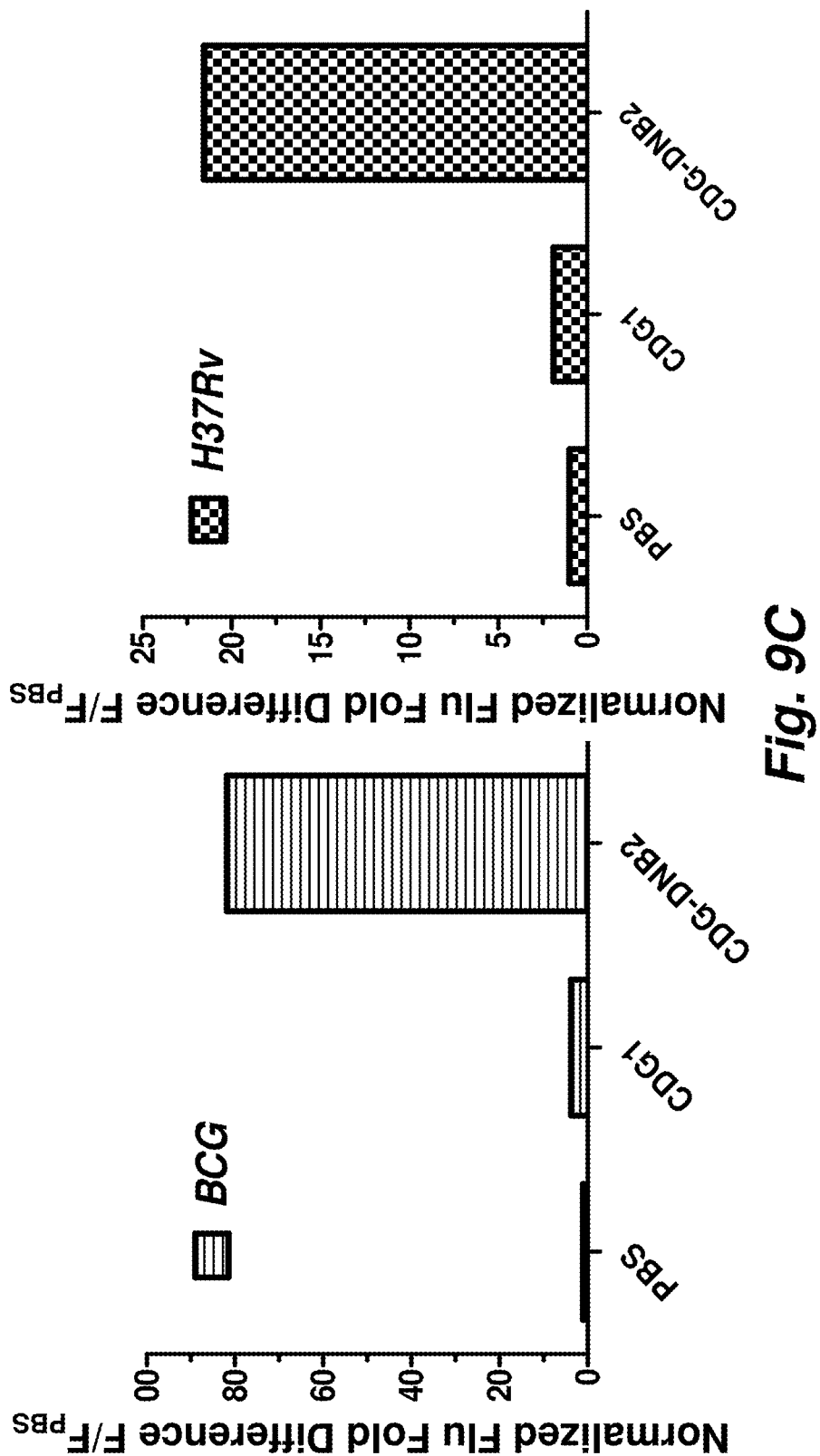
FIG. 9C illustrates a pair of graphs showing the mean values of fluorescence intensity collected by flow cytometry. The fluorescence intensity of PBS-treated cells of each strain was arbitrarily set as 1 to show the fold increasing (F/F$_{PBS}$). Experiments were repeated twice and showed similar results.
Figure 9D:
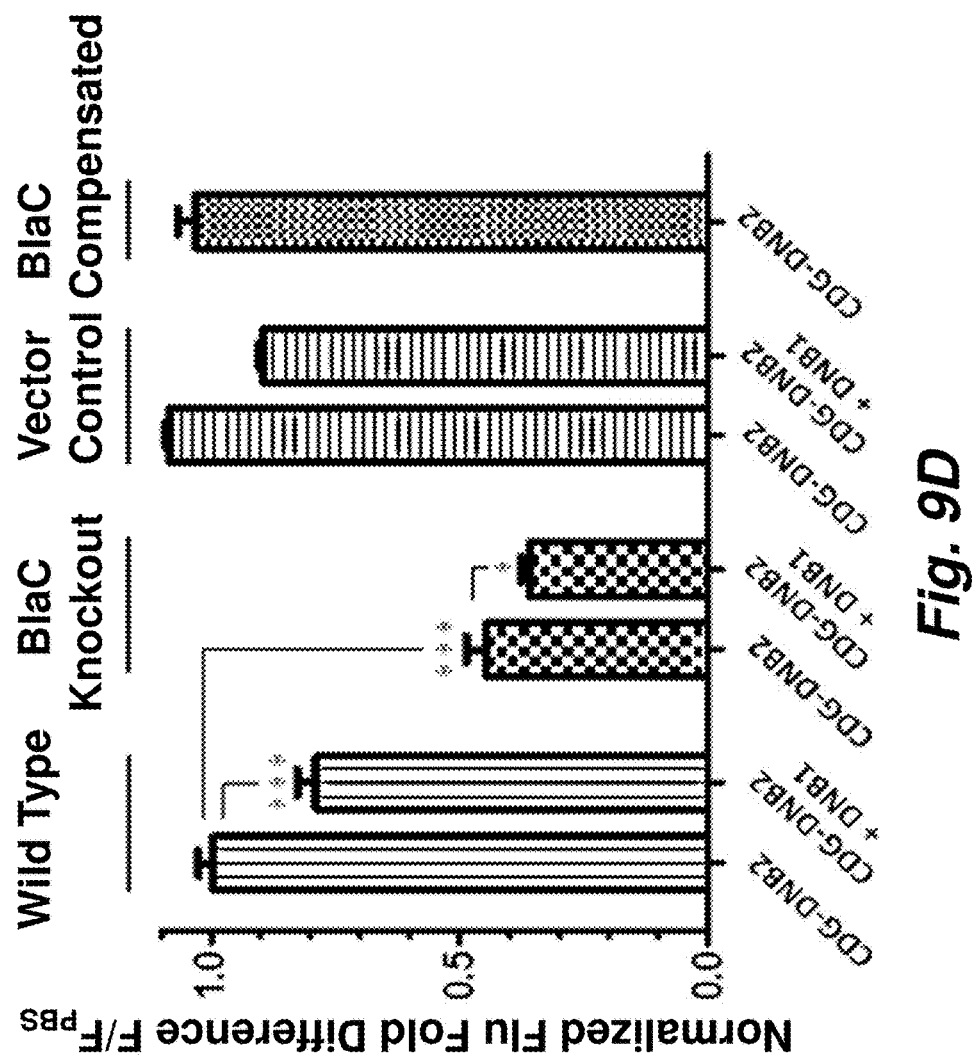
FIG. 9D is a graph illustrating fresh cultured wild type, BlaC knockout, and vector control *M. tuberculosis* H37Rv pretreated with 50 μM DNB1 at 37 degree for 1 h. Cells were then stained with 10 μM CDG-DNB2 at room temperature and washed with PBS for 3 times. PBS treated WT, BlaC KO, BlaC compensated and vector control H37Rv were also stained and analyzed in order to show the fold increase of fluorescence signal by CDG-DNB2. GraphPad Prism 5 software was utilized for statistical analysis. The fold increase of wild-type H37Rv strain by CDG-DNB2 was arbitrarily set as 1 to normalize the other groups. The significant difference was determined by performing one-way ANOVA followed by post hoc Bonferroni's multiple comparison test to determine the statistical significance with 95% confidence intervals with *p<0.05; p<0.01, *p<0.001 and ns, not significant (p>0.05). All error bars in figure represent ±SD, n=3.

As shown in FIG. 9A, both BCG and H37Rv could be stained with CDG-DNB2 and exhibited an intense (green) fluorescent signal. Cells were further quantitated by flow cytometry, as shown in FIG. 9B. Statistical analysis revealed that with CDG-DNB2 the fluorescence intensity with BCG increased by about 80-fold, and that of H37Rv by about 20-fold over control levels, as shown in FIG. 9C. These collective results indicate, therefore, that especially the dual-targeting probe CDG-DNB2 can be advantageously used as a probe for detecting potentially pathogenic strains of *Mycobacterium tuberculosis*.

Figure 10A:
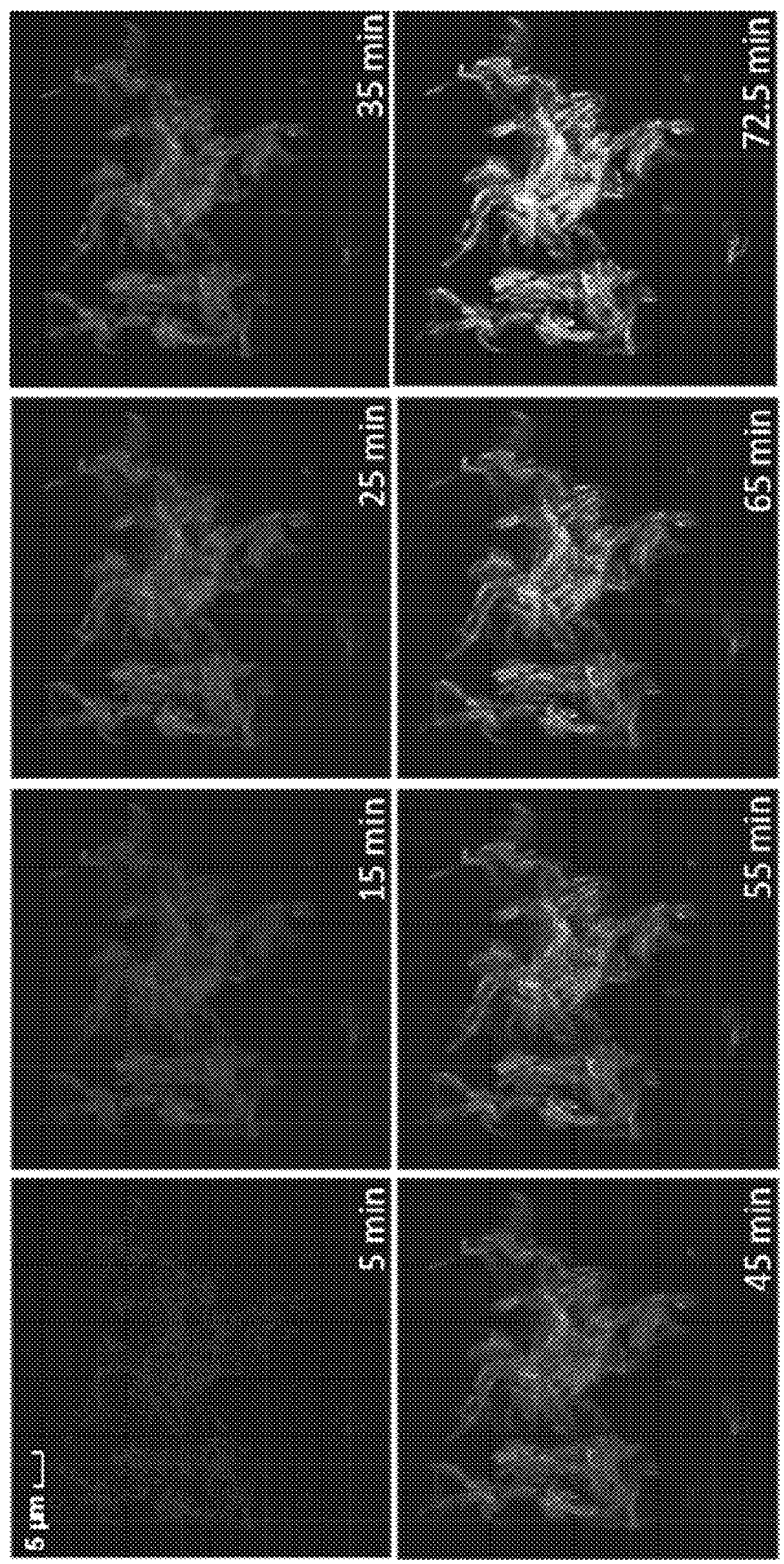
FIG. 10A is a series of digital confocal images. Freshly cultured BCG was suspended with 10 μM CDG-DNB2 at room temperature and then applied on glass slice immediately for confocal imaging. The BCG clot was imaged at λex=495 nm, λem=519 nm from 5 min for every 2.5 min.
Figure 10B:
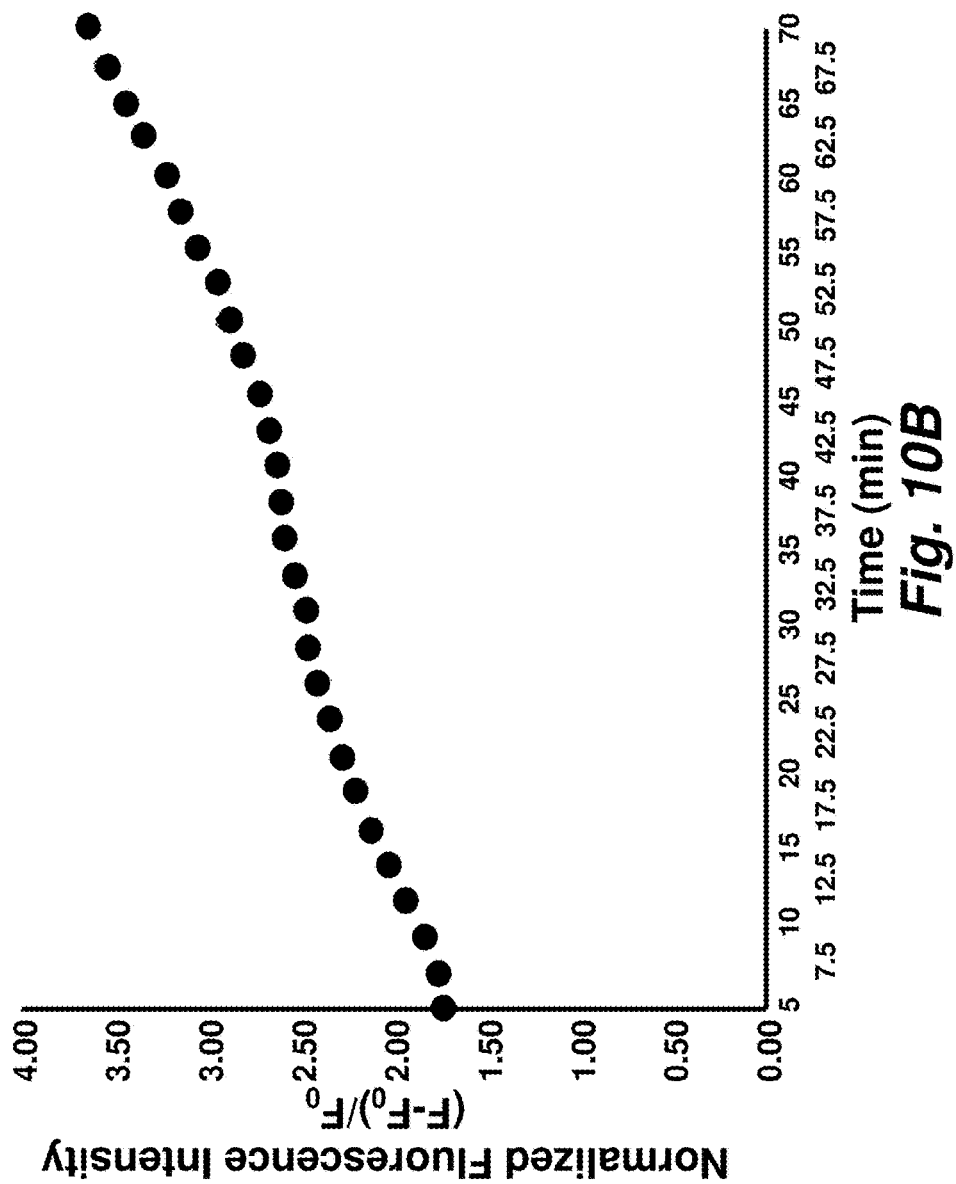
FIG. 10B is a graph illustrating the mean values of fluorescence intensity in images. Change of fluorescence intensity was normalized as $(F-F_0)/F_0$.

Due to the fluorogenic nature of the probes of the disclosure, a non-washing imaging protocol is advantageous for shortening the detection time and simplifying the workflow. Accordingly, BCG staining with CDG-DNB2 directly in medium was performed without any washing steps before subjecting the sample to confocal imaging. A time-dependent enhancement of the fluorescence signal was observed when the BCG clot was imaged continuously at intervals of 2.5 mins starting from 5 min after the incubation. Prominent fluorescence was observed as early as 15 min and a continuous enhancement till 75 min at each time the imaging was stopped, as shown in FIGS. 10A and 10B.

Figure 15:
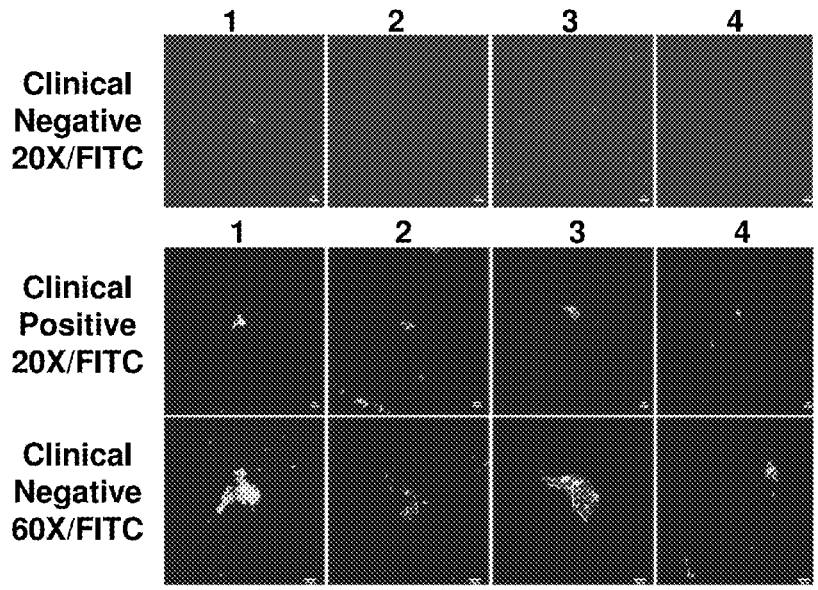
FIG. 15 is a series of digital fluorescence confocal microscope images of CDG-DNB2 stained patients' processed sputum samples. Processed sputum samples were centrifuged and resuspended in 10 μM CDG-DNB2 for 1 h at room temperature. Cells were pelleted and washed stringently 3 times with PBS before fixation with 10% formalin for 30 min. Cells were further visualized using a confocal microscope at 20× or 60×/Ex 490-Em520.

Clinical study with CDG-DNB2: Probe CDG-DNB2 has been evaluated in patients' clinical sputum samples: 4 positive and 4 negative samples. As shown in FIG. 15, 4 positive samples all displayed green fluorescence-stained bacteria while all the negative samples had little background fluorescence.

Another aspect of the disclosure encompasses probes and methods for DprE1-positve mycobacteria. Such a probe can include a flurophore linked to the DprE1-taregting group, for instance, DNB. In the case of the fluorophore with polar or charge groups, the fluorophore may be converted into an ester form, for instance, an AM ester in FIG. 14, to enhance cell permeability to achieve DprE1-1 targeting in mycobacteria. The ester will be cleaved by esterases inside mycobacteria to generate the fluorophore. Such methods of the disclosure can include contacting a biofluid or tissue sample, or administering to a whole animal or human subject a probe comprising a detectable label:DprE1-trapping conjugate or an ester group:detectable label:DprE1-trapping moiety conjugate as described in the present disclosure, and measuring an optical signal generated from contacting the sample with the probe (e.g., by detecting an optical signal derived from the detectable label by measuring absorbance, luminescence, chemiluminescence, fluorescence emission intensity, and the like). In these methods, the measured optical signal is indicative of the presence of β-lactamase positive DprE1-containing mycobacteria population in the sample.

It is noted that the esterase-reacting group may also be combined into a probe comprising a β-lactamase substrate group:detectable label:DprE1-trapping moiety conjugate. Such a probe will first interact with β-lactamase to release the conjugate containing the ester group:detectable label:DprE1-trapping moiety, which possess good cell permeability to enter cells. Esterases will then cleavage the ester to produce the fluorescent emission and the reaction with DprE1 will retain the detectable label inside mycobacteria.

The methods of the disclosure are suitable for the detecting, i.e. for the diagnosing of tuberculosis or a latent, and hence asymptomatic, mycobacteria infection in a human or animal patient.

In embodiments of the methods of use of the probes of the disclosure, suitable samples include sputum, pleural fluid, spinal fluid, blood, urine, saliva, stool, tissue biopsies, tissue homogenates, directly in live animals or human patients, or a sample obtained by swabbing an area of interest on a subject. The sample contacted with the probe compositions of the disclosure preferably may be liquid, or at least moist, thereby allowing the mycobacteria to actively transport the probe into the cells.

Measuring fluorescence emission intensity can usefully be achieved by exciting the sample with light having a wavelength in the range from about 300 nm to about 900 nm. In some embodiments of the methods of the disclosure, measuring fluorescence emission intensity comprises exciting the sample with light having a wavelength in the range from about 540 nm to about 730 nm.

Measuring fluorescence emission intensity can be by measuring emission at a wavelength in the range from about 300 nm to about 900 nm. The wavelength may be selected depending upon the known properties of the detectable label incorporated into the probe. In other embodiments, measuring fluorescence emission intensity comprises measuring emission at a wavelength in the range from about 650 nm to about 800 nm.

The methods of the disclosure can be advantageously used to generate images of mycobacteria infections in such as small animals, and therefore not only useful for detecting an infection in an animal patient but also useful for monitoring the increase or decrease of the extent of an infection in an animal when subjected to an antibiotic. In addition, it is contemplated that by labeling mycobacteria in a human or animal patient such infections may be visualized by such means as an endoscope device that can excite a fluorescent label of the targeted mycobacteria and then visualized within the lungs and the like by inserting a camera.

The fluorescent and dye labeled probes of the disclosure also allow for the quantifiable detection of the probe once bound to the DprE1 protein of a target mycobacteria and allow the direct visualization, not just of a population of such cells but also of a single *mycobacterium*.

One aspect of the disclosure, therefore, encompasses embodiments of a probe specific for a *mycobacterium*, wherein said probe can consist of a detectable label covalently attached to a *mycobacterium*-specific decaprenylphosphoryl-β-D-ribose 2'-epimerase (DprE1)-trapping moiety, or an ester or salt thereof.

In some embodiments of this aspect of the disclosure, the probe can further comprise a β-lactamase substrate group covalently attached to the detectable label, wherein said probe specifically detects a *mycobacterium* having a β-lactamase activity.

In some embodiments of this aspect of the disclosure, the *mycobacterium*-specific DprE1-trapping moiety can be covalently attached to the detectable label by a first linker.

In some embodiments of this aspect of the disclosure, the probe can have the formula I or II:

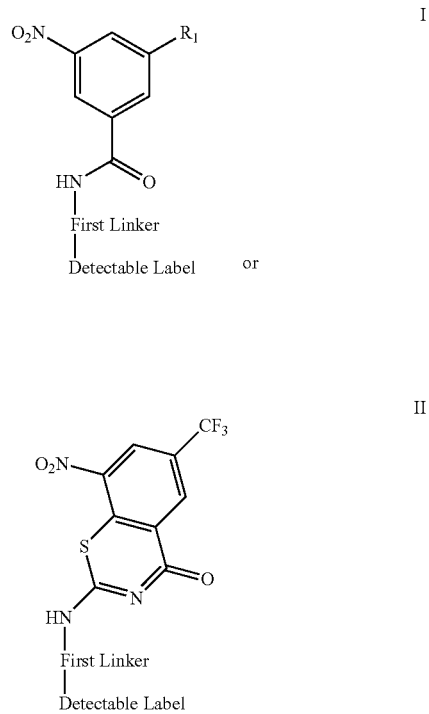

and
wherein $R_1$ is H, —$NO_2$, or $CF_3$.

In some embodiments of this aspect of the disclosure, the first linker can be selected from the group consisting of: ethoxyphenyl, —$CH_2$—$CH_2$—, -1-ethyl 3-methyl 1,2,3-triazole, and —$CH_2$—$CH_2$—$NR_2$—CS—$NH_2$—, wherein $R_2$ is H or —$CH_3$.

In some embodiments of this aspect of the disclosure, the β-lactamase substrate group can be covalently attached to the detectable label by a second linker, said second linker having a formula selected from the group consisting of:

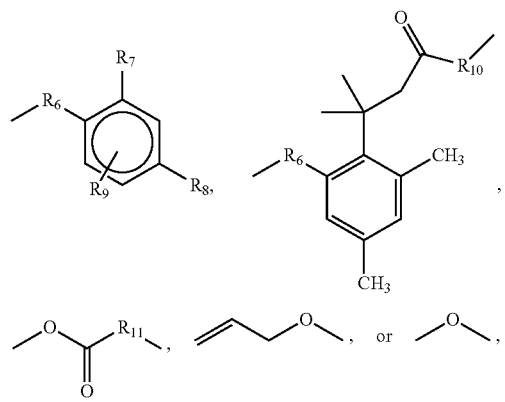

wherein: $R_6$ is O or S; if $R_7$ is —$CH_2$—O—, or —$CH_2$—CO—NH—, or —$CH_2$—CO—O— then $R_3$ is H and if $R_3$ is —$CH_2$—O— then $R_2$ is H; if $R_8$ is —$CH_2$—CO—O—, then $R_2$ and $R_4$ are H; $R_9$ is a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, an hydroxyl, a substituted alkenyl, a substituted cycloaliphatic, a substituted aliphatic, a thiol, a thioalkoxy, a thioalkyl, a thioaryl, a thiol, a a thiophene, or a substituted thiophene; and $R_{10}$ and $R_{11}$ are each independently O or NH.

In some embodiments of this aspect of the disclosure, the β-lactamase substrate group is covalently attached to the detectable label by a second linker, said second linker having a formula selected from the group consisting of:

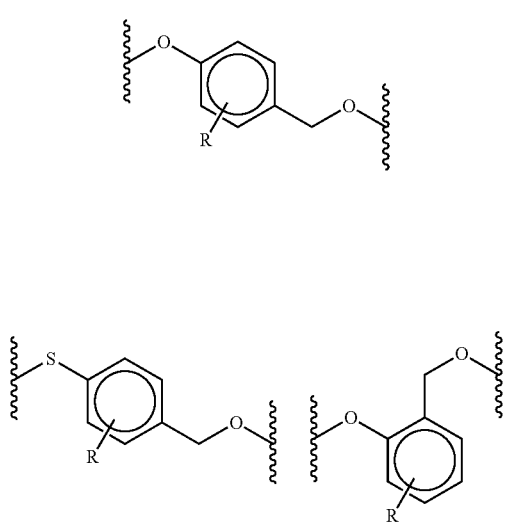

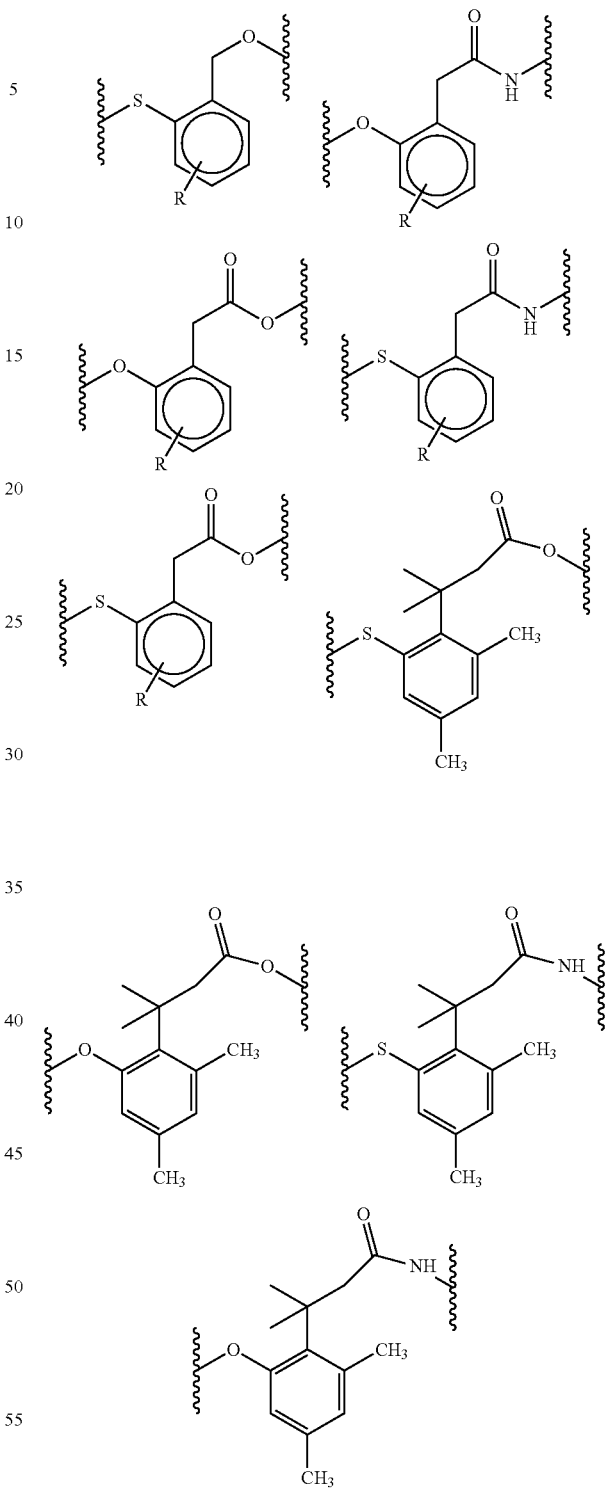

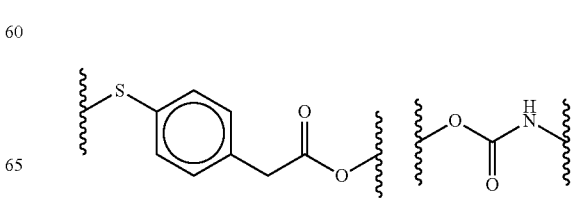

-continued

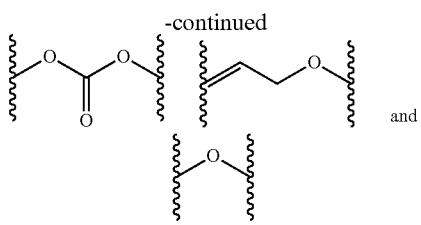
and

In embodiments of this aspect of the disclosure, the detectable label can be a fluorophore or a dye.

In embodiments of this aspect of the disclosure, the detectable label is a fluorophore or a dye having a caging group covalently attached thereto by an esterase-cleavable ester bond.

In embodiments of this aspect of the disclosure, the detectable label is a fluorophore or a dye having a caging group covalently attached thereto by an esterase-cleavable ester bond, wherein said caging group is an acetoxymethyl group.

In embodiments of this aspect of the disclosure, the detectable label can be a fluorescein, an acridine, an alizarene, an azo dye, an anthraquinine dye, a bodipy dye, a coumarin dye, a cyanine dye, a lanthanide complex, an oxazine dye, a phenazathionium dye, a phenazoxonium dye, a porphyorin, a pyrene, a pyrilium, a perylene, a phenoxazine, a phenezine, a rhodol, a rhodamine, or a xanthene dye.

In some embodiments of this aspect of the disclosure, the detectable label can have the formula III or IV:

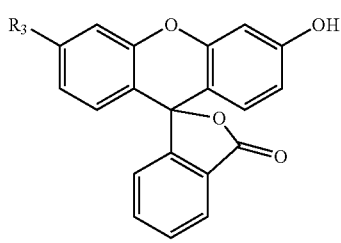

III or

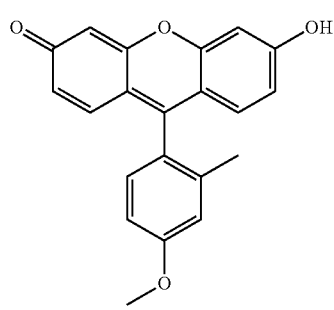

IV wherein $R_3$ can be O, N, or —NCH$_3$—CO—NH—.

In some embodiments of this aspect of the disclosure, the detectable label can be selected from the group consisting of: Cascade Blue, Cascade Yellow, 7-amino-4-methylcoumarin, aminocoumarin, hydroxycoumarin, Cy3, Cy5, fluorescein isothiocyanate, Quantum Dye®, Marina Blue, rhodamine red, tetramethylrhodamine, rhodamine 6G, Texas Red, thiazole orange-ethidium heterodimer, TOTAB, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, BODIPY-TR, Cy5,6-FAM, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, TET, 3-Hydroxypyrene 5,8,10-Tri Sulfonic acid, 5-Hydroxy Tryptamine, 5-Hydroxy Tryptamine (5-HT), Acid Fuchsine, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, an aryl-substituted polyolefin, a heteroaryl-substituted polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulfate, Bisbenzamnide, BOBO 1, Biancophor FFG Solution, Blancophor SV, Bodipy Fl, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diainino Naphtyl Sulphonic Acid), Dansyl NH—CH$_3$, DAPI, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Ethidium Bromide, Euchrysin, Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Maxilon Brilliant Flavin 10 GFF, Maxilon Brilliant Flavin 8 GFF, MPS (Methyl Green Pyronine Stilbene), Mithrarnycin, NBD Amine, Nile Red, Nitrobenzoxadidole, Noradrenaline, Nuclear Fast Red, Nuclear Yellow, Nylosan Brilliant Flavin E8G, Oxazine, Oxazole, Oxadiazole, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, and YO PRO 1.

In some embodiments of this aspect of the disclosure, the fluorophore can be selected from the group consisting of: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5,6-FAM, Fluorescein, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5', 7'-Tetrabromosulfonefluorescein, TET, and Tokyo Green.

In some embodiments of this aspect of the disclosure, the detectable label is a rhodol analog having the formula V:

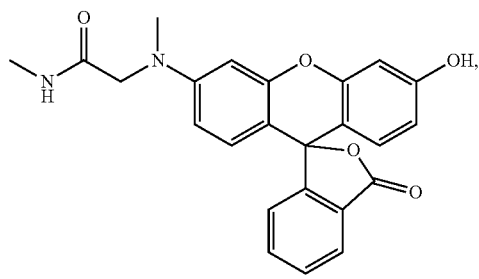

V fluorescein, fluorescein isothiocyanate (FITC), fluorescein isothiocyanate acetoxymethyl ester (FITC-AM), Oregon Green, Tokyo Green, or Tokyo Green-acetoxymethyl ester.

In some embodiments of this aspect of the disclosure, the β-lactamase substrate group can have the formula VI:

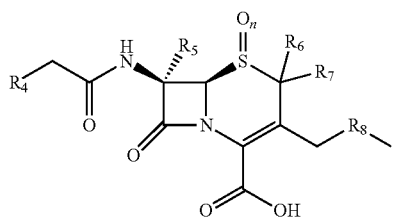

VI wherein: n=0 or 1; $R_4$ can be selected from the group consisting of: a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, a substituted alkenyl, a substituted cycloaliphatic, a substituted aliphatic, a thiol, a thioalkoxy, a thioalkyl, a thioaryl, a thiophene, or a substituted thiophene; $R_5$ is H, OMe, Me, —$CH_2CH_3$, —$CF_3$, —$CH_2CF_3$, —$CF_2CH_3$, —$CHF_2$, —$CH_2F$, —$OCH_2F$, or —$OCHF_2$; $R_6$ and $R_7$ are each H or

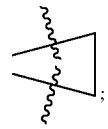 [SMILES: *CC*]

and $R_8$ is O or S.

In some embodiments of this aspect of the disclosure, the probe can be as shown in FIG. 12,

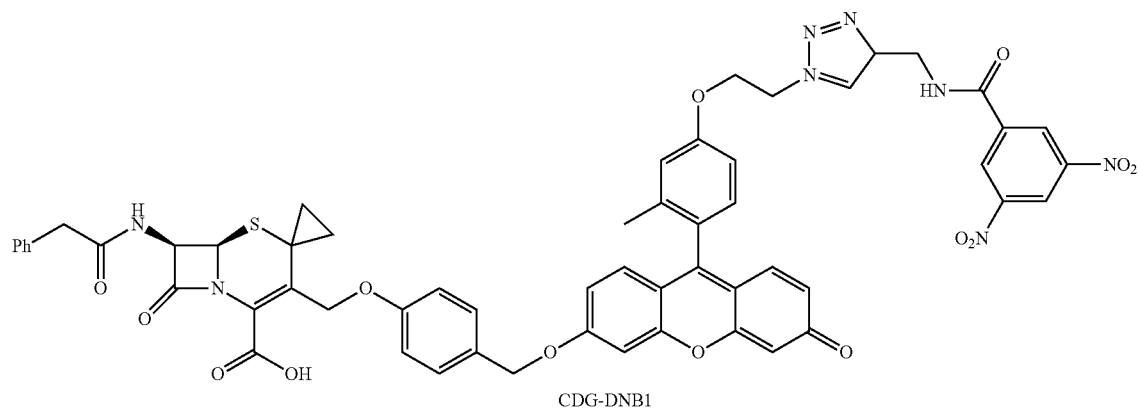

CDG-DNB1

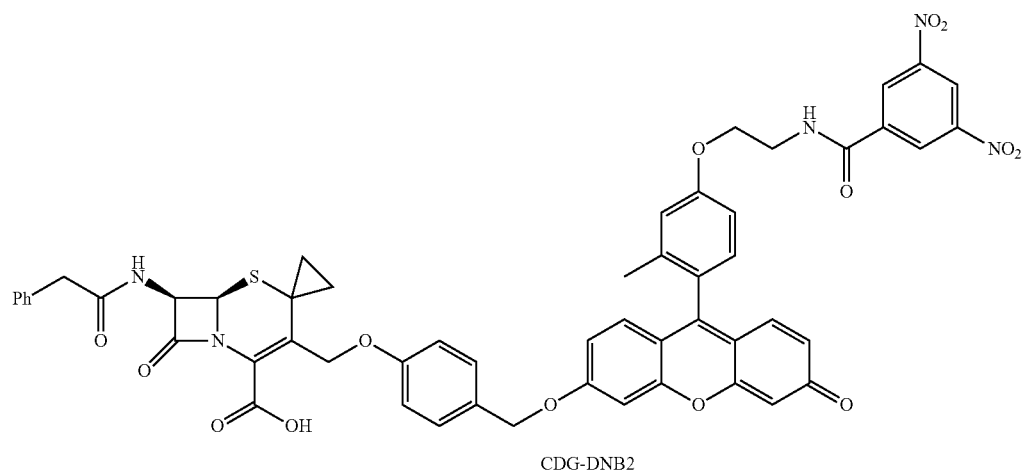
CDG-DNB2
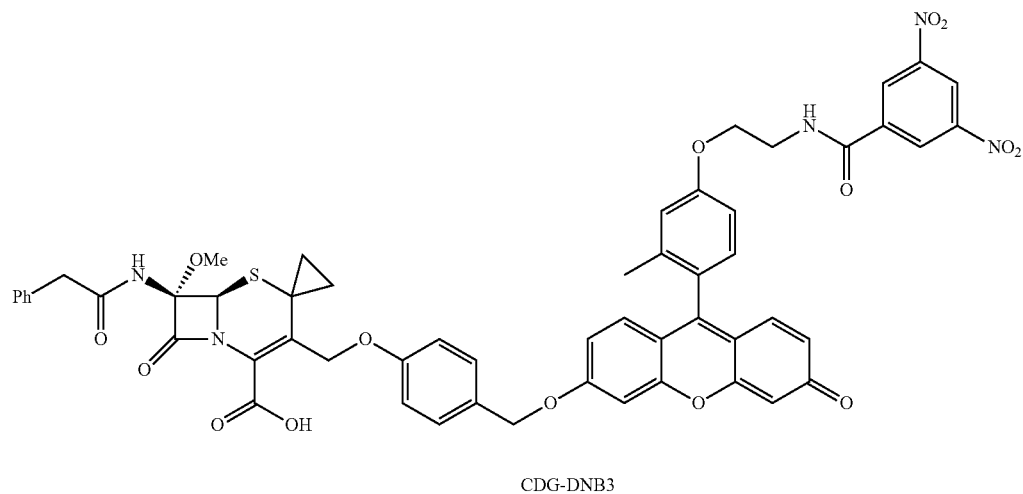
CDG-DNB3
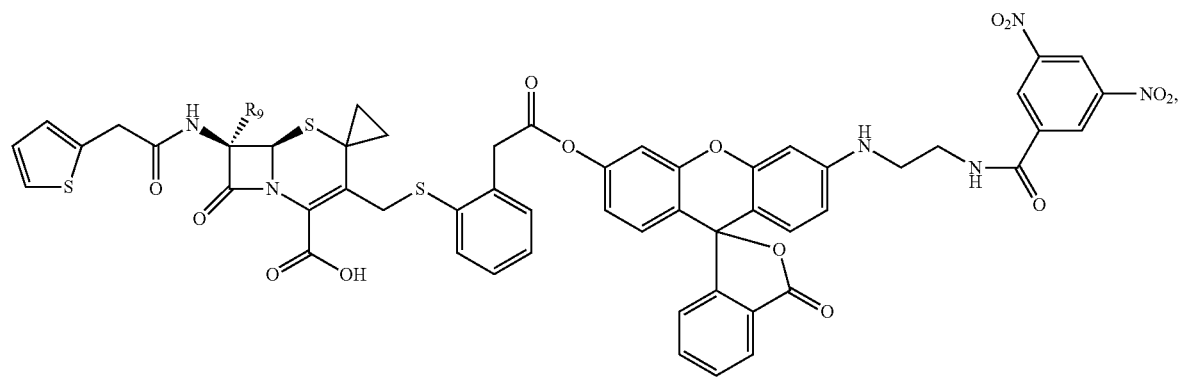

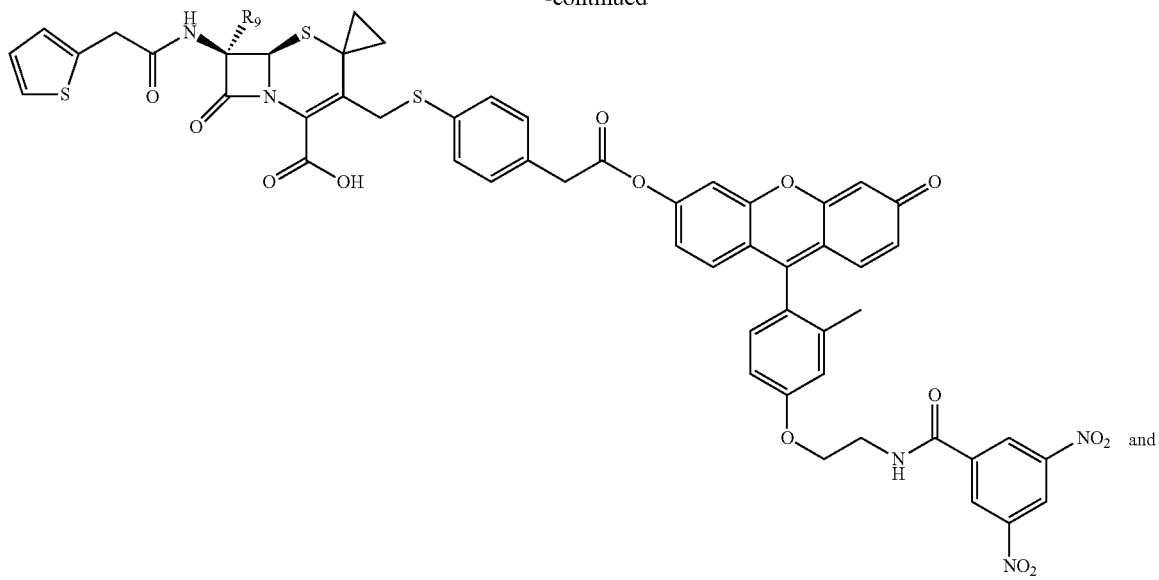

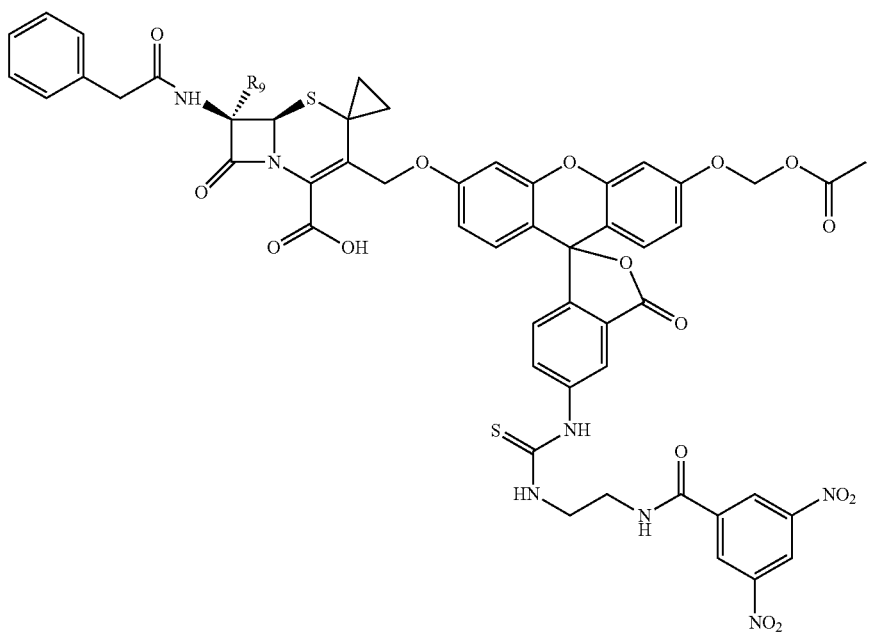

wherein $R_9$ in each formula is selected from the group consisting of: H, OMe, Me, —$CH_2CH_3$, —$CF_3$, —$CH_2CF_3$, —$CF_2CH_3$, —$CHF_2$, —$CH_2F$, —$OCH_2F$, or —$OCHF_2$.

In embodiments of this aspect of the disclosure, the probe can be admixed with a carrier or vehicle.

Another aspect of the disclosure encompasses embodiments of a probe specific for a *mycobacterium*, said probe comprising a β-lactamase substrate group covalently attached to the detectable label group, wherein the β-lactamase substrate group has the formula VI:

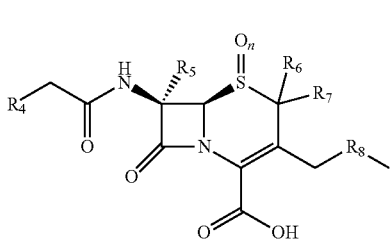

wherein: n=0 or 1; $R_4$ is selected from the group consisting of: a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, a substituted alkenyl, a substituted cycloaliphatic, a substituted aliphatic, a thiol, a thioalkoxy, a thioalkyl, a thioaryl, a thiophene, or a substituted thiophene; $R_5$ is H, OMe, Me, —$CH_2CH_3$, —$CF_3$, —$CH_2CF_3$, —$CF_2CH_3$, —$CHF_2$, —$CH_2F$, —$OCH_2F$, or —$OCHF_2$; $R_6$ and $R_7$ are each H or

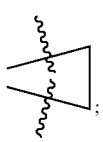 [SMILES: *CC*]

and $R_8$ is O or S.

In embodiments of this aspect of the disclosure, the probe can further comprise a linker between the β-lactamase substrate group and the detectable label, wherein said linker has a formula selected from the group consisting of:

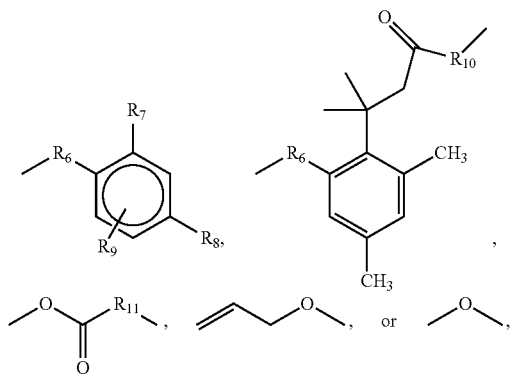

wherein: $R_6$ is O or S; if $R_7$ is —$CH_2$—O—, or —$CH_2$—CO—NH—, or —$CH_2$—CO—O— then $R_8$ is H and if $R_8$ is —$CH_2$—O— then $R_7$ is H; if $R_8$ is —$CH_2$—CO—O—, then $R_7$ and $R_9$ are H; $R_9$ is a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, an hydroxyl, a substituted alkenyl, a substituted cycloaliphatic, a substituted aliphatic, a thiol, a thioalkoxy, a thioalkyl, a thioaryl, a thiol, a a thiophene, or a substituted thiophene; and $R_{10}$ and $R_{11}$ are each independently O or NH.

In some embodiments of this aspect of the disclosure, the detectable label is a fluorescein, an acridine, an alizarene, an azo dye, an anthraquinine dye, a bodipy dye, a coumarin dye, a cyanine dye, a lanthanide complex, an oxazine dye, a phenazathionium dye, a phenazoxonium dye, a porphyorin, a pyrene, a pyrilium, a perylene, a phenoxazine, a phenezine, a rhodol, a rhodamine, or a xanthene dye.

In some embodiments of this aspect of the disclosure, the detectable label has a caging group covalently attached thereto by an esterase-cleavable ester bond.

In embodiments of this aspect of the disclosure, the detectable label is a fluorophore or a dye having a caging group covalently attached thereto by an esterase-cleavable ester bond, wherein said caging group is an acetoxymethyl group.

In embodiments of this aspect of the disclosure, the probe further comprises a mycobacterium-specific decaprenyl-phosphoryl-β-D-ribose 2'-epimerase (DprE1)-trapping moiety, or an ester or salt thereof, said DprE1-trapping moiety covalently attached to the detectable label.

In embodiments of this aspect of the disclosure, the mycobacterium-specific DprE1-trapping moiety is covalently attached to the detectable label by a first linker.

In embodiments of this aspect of the disclosure, the mycobacterium-specific DprE1-trapping moiety has the formula:

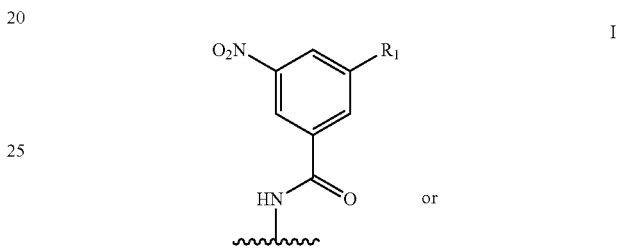

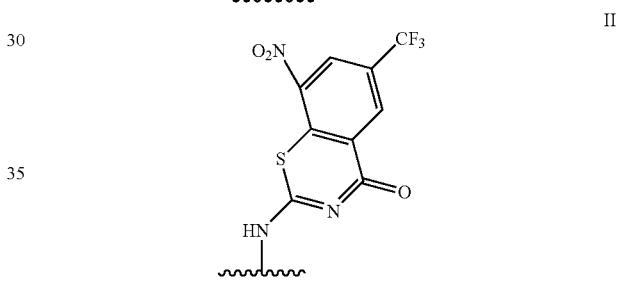

and wherein $R_1$ is H, —$NO_2$, or $CF_3$.

In embodiments of this aspect of the disclosure, the first linker is selected from the group consisting of: ethoxyphenyl, —$CH_2$—$CH_2$—, -1-ethyl 3-methyl 1,2,3-triazole, and —$CH_2$—$CH_2$—$NR_2$—CS—$NH_2$—, wherein $R_2$ is H or —$CH_3$.

Another aspect of the disclosure encompasses embodiments of a method of selectively detecting a mycobacterium, said method comprising the steps of: contacting a sample suspected of having a mycobacterium with a composition comprising a probe, said probe consisting of a detectable label covalently attached to a mycobacterium-specific decaprenylphosphoryl-β-D-ribose 2'-epimerase (DprE1)-trapping moiety; and detecting a signal emitted by the probe covalently attached to a DprE1 protein of a mycobacterium.

In some embodiments of this aspect of the disclosure, the probe can further comprise a β-lactamase substrate group covalently attached to the detectable label, wherein said probe specifically detects a mycobacterium having a β-lactamase activity.

In some embodiments of this aspect of the disclosure, the mycobacterium-specific DprE1-trapping moiety can be covalently attached to the detectable label by a first linker.

In some embodiments of this aspect of the disclosure, the probe can have the formula I or II:

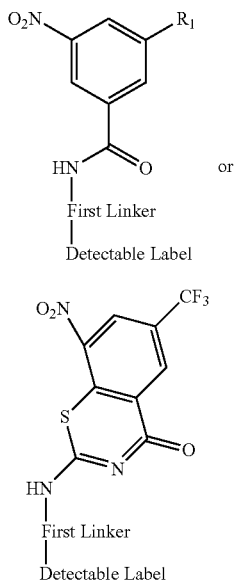

and
wherein $R_1$ is H, —$NO_2$, or $CF_3$.

In some embodiments of this aspect of the disclosure, the first linker can be selected from the group consisting of: ethoxyphenyl, —$CH_2$—$CH_2$—, -1-ethyl 3-methyl 1,2,3-triazole, and —$CH_2$—$CH_2$—$NR_2$—CS—$NH_2$—, wherein $R_2$ is H or —$CH_3$.

In some embodiments of this aspect of the disclosure, the β-lactamase substrate group can be covalently attached to the detectable label by a second linker, said second linker having a formula selected from the group consisting of:

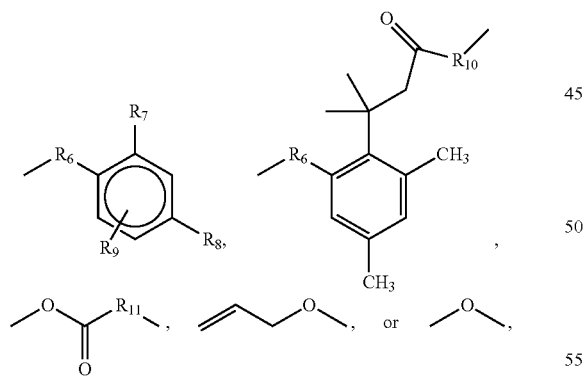

wherein: $R_6$ is O or S; if $R_7$ is —$CH_2$—O—, or —$CH_2$—CO—NH—, or —$CH_2$—CO—O— then $R_8$ is H and if $R_8$ is —$CH_2$—O— then $R_7$ is H; if $R_8$ is —$CH_2$—CO—O—, then $R_7$ and $R_9$ are H; $R_9$ is a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxy, an aroyl, an aroylamino, an aryl, a substituted aryl group, a carbamoyl, a carbonyl, a carboxamide, a carboxyl, a heteroaryl, a heterocyclic, a hydroxyalkyl, an hydroxyl, a substituted alkenyl, a substituted cycloaliphatic, a substituted aliphatic, a thiol, a thioalkoxy, a thioalkyl, a thioaryl, a thiol, a a thiophene, or a substituted thiophene; and $R_{10}$ and $R_{11}$ are each independently O or NH.

In embodiments of this aspect of the disclosure, the detectable label can be a fluorophore or a non-fluorescent dye.

In some embodiments of this aspect of the disclosure, the detectable label is a fluorophore or a dye can have a caging group covalently attached thereto by an esterase-cleavable ester bond.

In some embodiments of this aspect of the disclosure, the detectable label can be a fluorophore or a dye having a caging group covalently attached thereto by an esterase-cleavable ester bond, wherein said caging group is an acetoxymethyl group.

In some embodiments of this aspect of the disclosure, the detectable label can be a fluorescein, an acridine, an alizarene, an azo dye, an anthraquinine dye, a bodipy dye, a coumarin dye, a cyanine dye, a lanthanide complex, an oxazine dye, a phenazathionium dye, a phenazoxonium dye, a porphyorin, a pyrene, a pyrilium, a perylene, a phenoxazine, a phenezine, a rhodol, a rhodamine, or a xanthene dye.

In some embodiments of this aspect of the disclosure, the detectable label can have the formula III or IV:

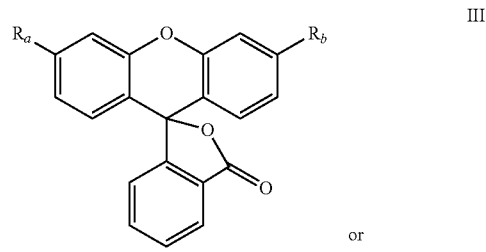

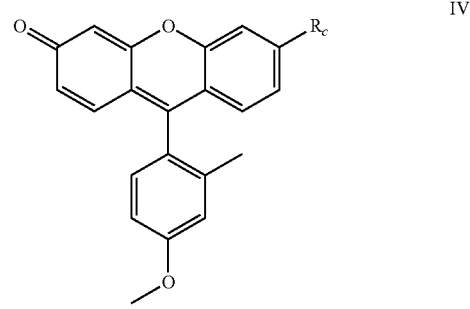

wherein $R_a$, $R_b$, and $R_c$ can be each independently O, N, or —$NCH_3$—CO—NH—, or an esterified caging group.

In embodiments of this aspect of the disclosure, the detectable label is selected from the group consisting of: Cascade Blue, Cascade Yellow, 7-amino-4-methylcoumarin, aminocoumarin, hydroxycoumarin, Cy3, Cy5, fluorescein isothiocyanate, Quantum Dye®, Marina Blue, rhodamine red, tetramethylrhodamine, rhodamine 6G, Texas Red, thiazole orange-ethidium heterodimer, TOTAB, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, BODIPY-TR, Cy5,6-FAM, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, TET, 3-Hydroxypyrene 5,8,10-Tri Sulfonic acid, 5-Hydroxy Tryptamine, 5-Hydroxy Tryptamine (5-HT), Acid Fuchsine, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, an aryl-substituted polyolefin, a heteroaryl-substituted polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulfate, Bisbenzamnide, BOBO 1, Biancophor FFG Solution, Blancopor SV, Bodipy F1, BOPRO 1, Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diainino Naphtyl Sulphonic Acid), Dansyl NH—$CH_3$, DAPI, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Ethidium Bromide, Euchrysin, Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Hoechst 33258, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oxazine, Oxazole, Oxadiazole, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene lsothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, Tokyo Green, TOTO 1, TOTO 3, True Blue, Ultralite, Uranine B, Uvitex SFC, Xylene Orange, XRITC, and YO PRO 1.

In some embodiments of this aspect of the disclosure, the detectable label can be the rhodol analog having the formula V:

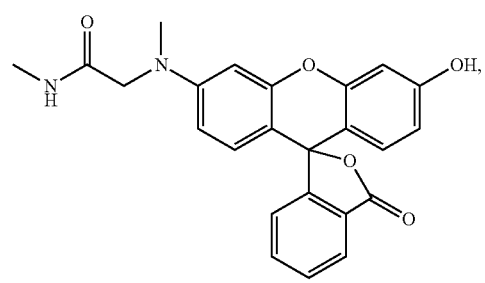

fluorescein, fluorescein isothiocyanate (FITC), fluorescein isothiocyanate acetoxymethyl ester (FITC-AM), Oregon Green, Tokyo Green, or Tokyo Green-acetoxymethyl ester.

In some embodiments of this aspect of the disclosure, the β-lactamase substrate group can have the formula VI:

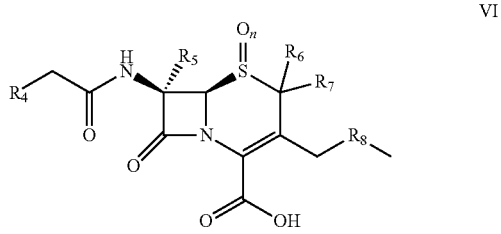

wherein: n=0 or 1; R₄ is selected from the group consisting of: a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, a substituted alkenyl, a substituted cycloaliphatic, a substituted aliphatic, a thiol, a thioalkoxy, a thioalkyl, a thioaryl, a thiophene, or a substituted thiophene; $R_5$ is H, OMe, Me, —CH₂CH₃, —CF₃, —CH₂CF₃, —CF₂CH₃, —CHF₂, —CH₂F, —OCH₂F, or —OCHF₂; $R_6$ and $R_7$ are each H or

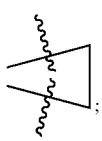 [SMILES: *CC*]

and $R_8$ is O or S.

In some embodiments of this aspect of the disclosure, the probe can be selected from the group consisting of:

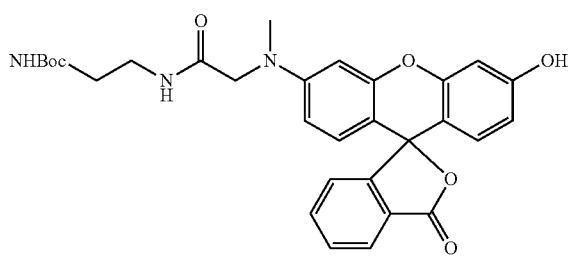

Rd-Boc

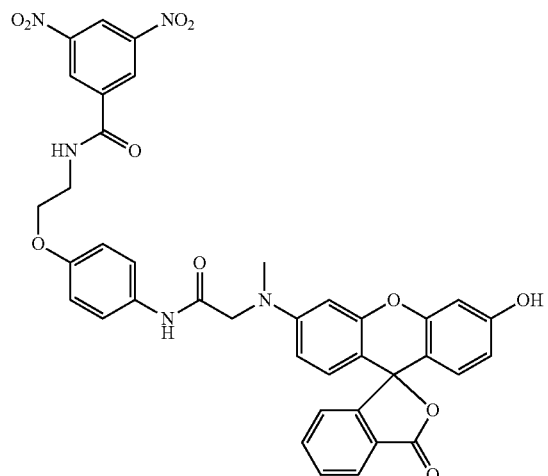

Rd-DNB1

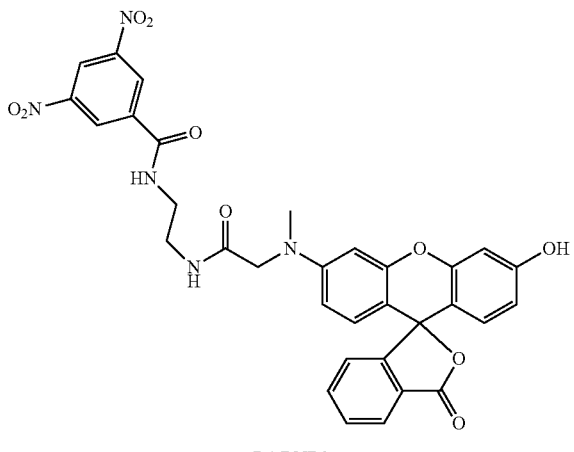

Rd-DNB2

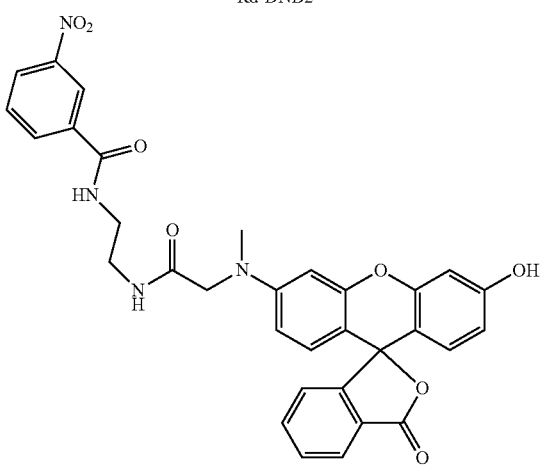

Rd-DNB3

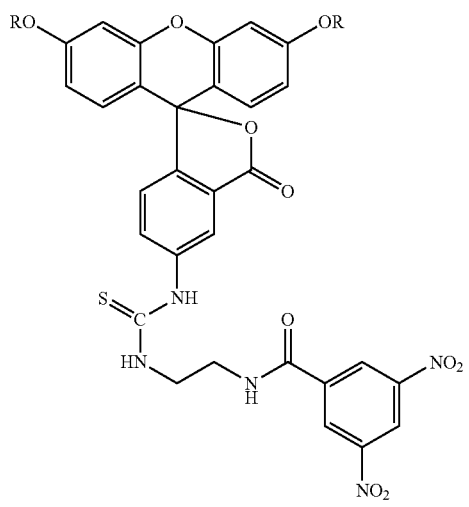

FITC-DNB1 (R = H)
AM-FITC-DNB1 (R = acetoxymethyl)

-continued
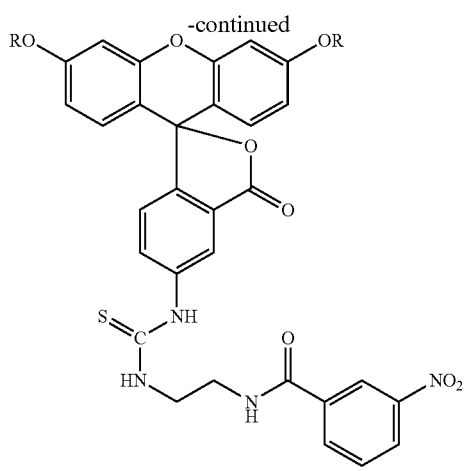
FITC-DNB2 (R = H)
AM-FITC-DNB2 (R = acetoxymethyl)
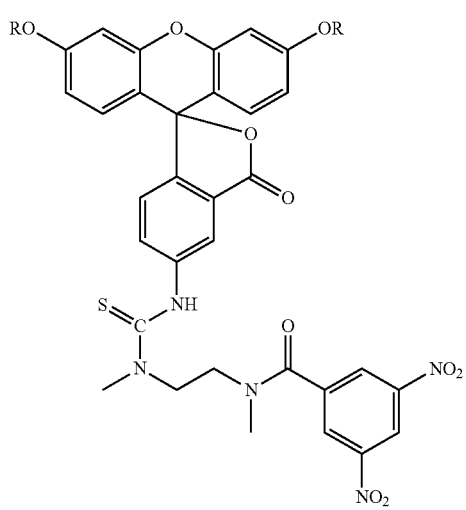
FITC-DNB3 (R = H)
AM-FITC-DNB3 (R = AM)
-continued
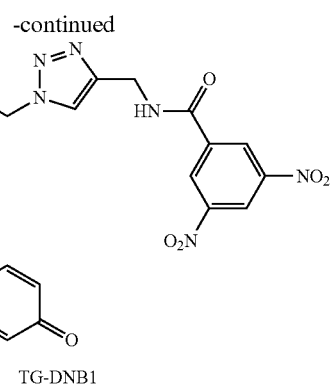
TG-DNB1
TG-DNB2 (R = H)
AM-TG-DNB2 (R = acetoxymethyl)
In some embodiments of this aspect of the disclosure, the probe can be selected from the group consisting of:
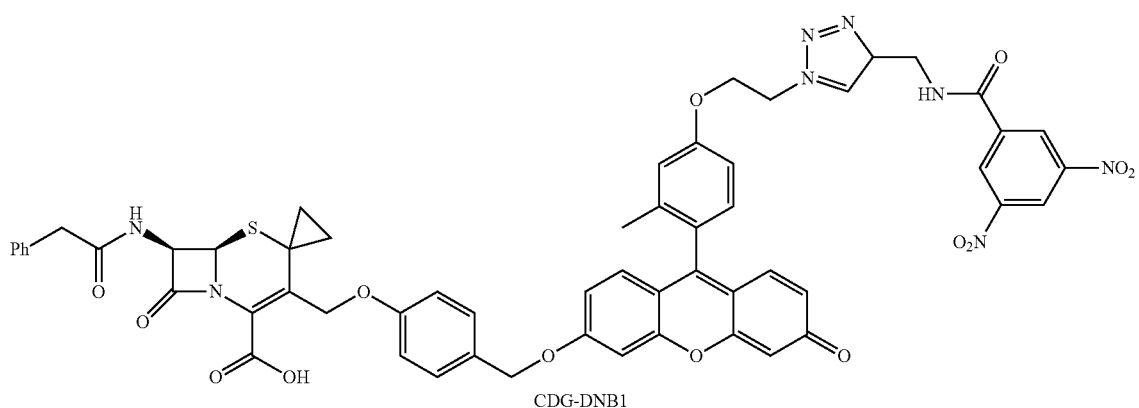
CDG-DNB1

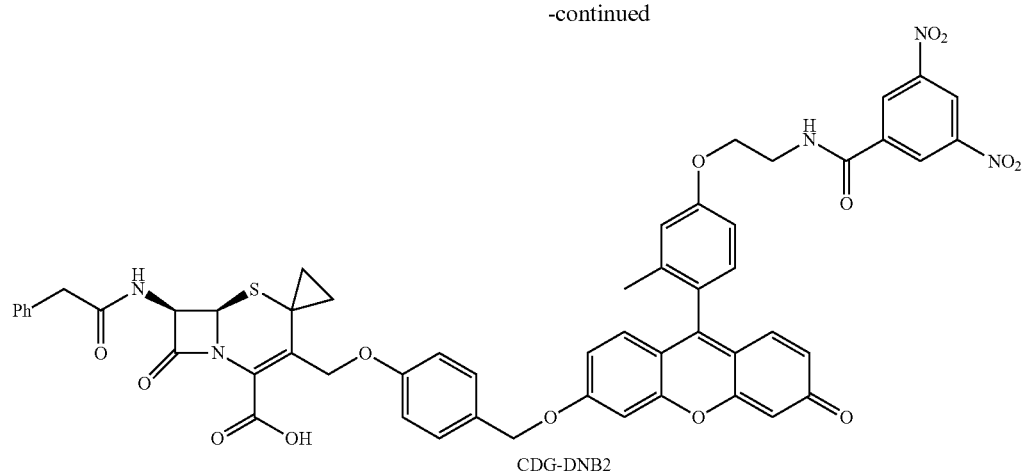
CDG-DNB2
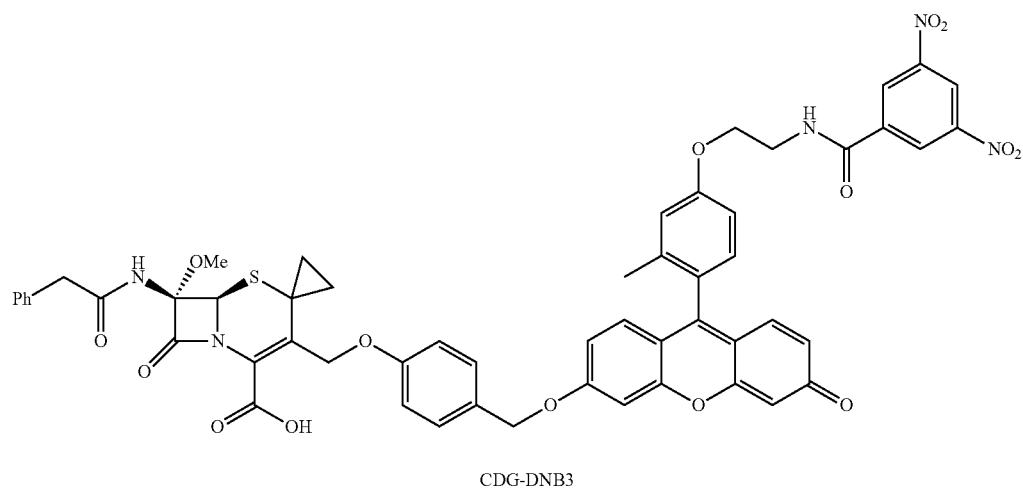
CDG-DNB3
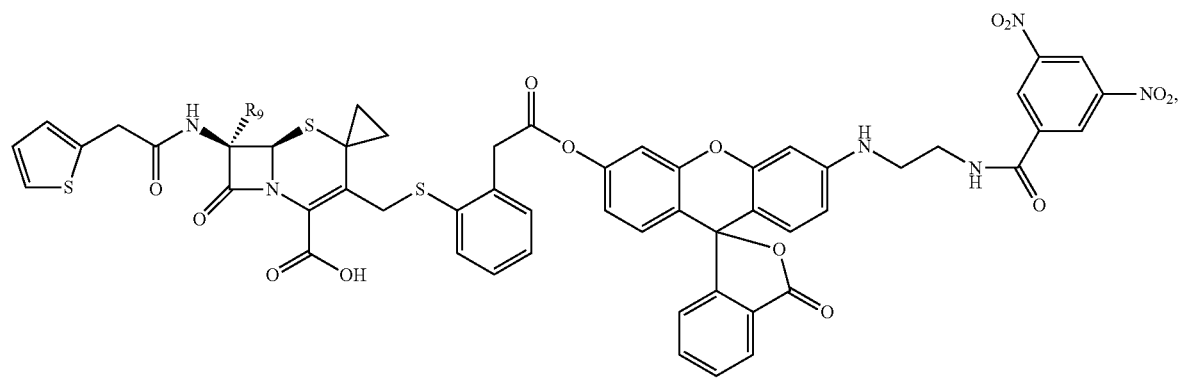

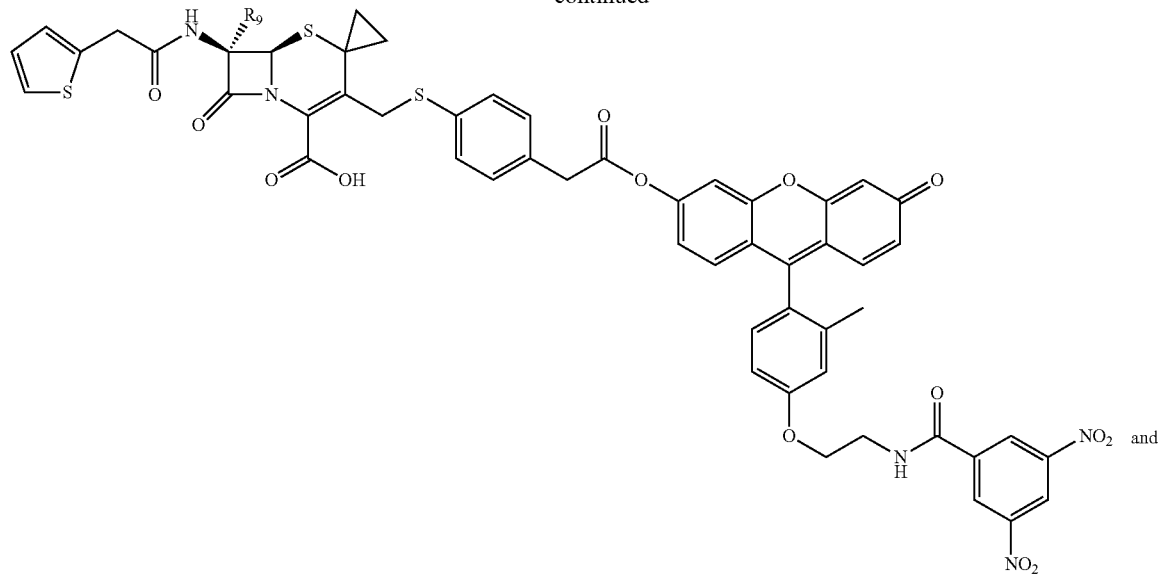

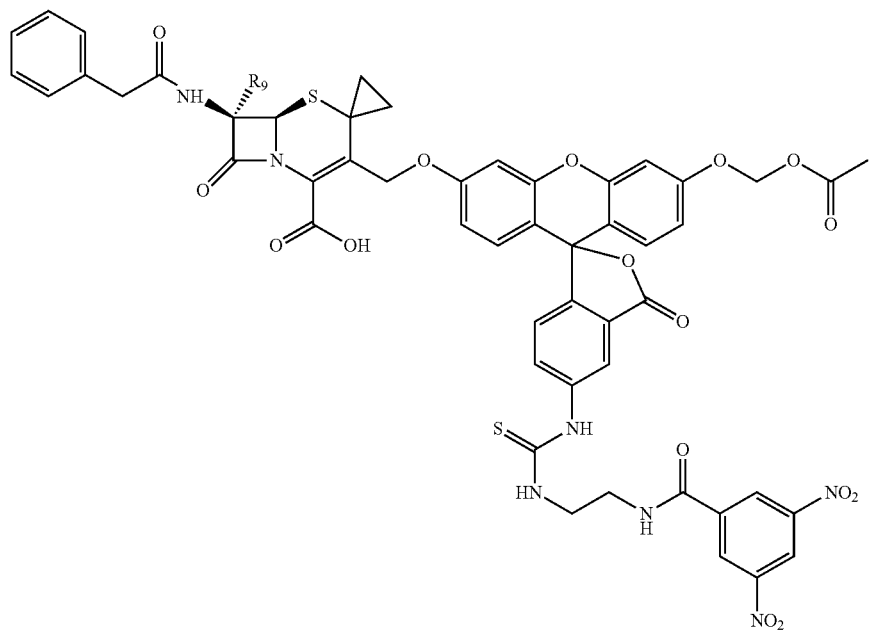

wherein $R_9$ is each independently H, OMe, Me, —$CH_2CH_3$, —$CF_3$, —$CH_2CF_3$, —$CF_2CH_3$, —$CHF_2$, —$CH_2F$, —$OCH_2F$, or —$OCHF_2$ In some embodiments of this aspect of the disclosure, the method can further comprise, before the step of detecting the detectable label, washing the sample to remove probe not in contact with mycobacteria therein.

Another aspect of the disclosure encompasses embodiments of a method of selectively detecting a *mycobacterium*, said method comprising the steps of: contacting a sample suspected of having a *mycobacterium* with a composition comprising a probe comprising a β-lactamase substrate group covalently attached to the detectable label group, wherein the β-lactamase substrate group has the formula VI:

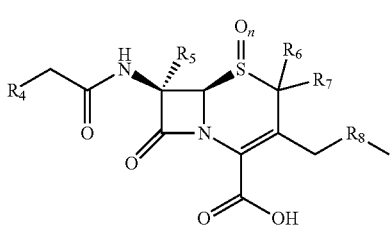

VI wherein: n=0 or 1; $R_4$ is selected from the group consisting of: a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, a substituted alkenyl, a substituted cycloaliphatic, a substituted aliphatic, a thiol, a thioalkoxy, a thioalkyl, a thioaryl, a thiophene, or a substituted thiophene; $R_5$ is H, OMe, Me, —$CH_2CH_3$, —$CF_3$, —$CH_2CF_3$, —$CF_2CH_3$, —$CHF_2$, —$CH_2F$, —$OCH_2F$, or —$OCHF_2$; $R_6$ and $R_7$ are each H or

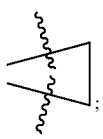

and $R_8$ is O or S; and detecting a signal emitted by the probe covalently attached to a DprE1 protein of a *mycobacterium*.

In some embodiments of this aspect of the disclosure, the method can further comprise a linker between the β-lactamase substrate group and the detectable label, wherein said linker can have a formula selected from the group consisting of:

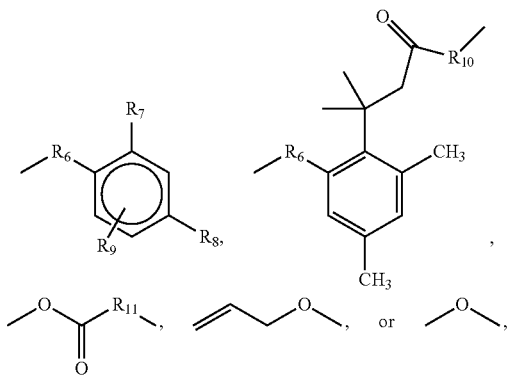

wherein: $R_6$ is O or S; if $R_7$ is —$CH_2$—O—, or —$CH_2$—CO—NH—, or —$CH_2$—CO—O— then $R_8$ is H and if $R_8$ is —$CH_2$—O— then $R_7$ is H; if $R_8$ is —$CH_2$—CO—O—, then $R_7$ and $R_9$ are H; $R_9$ is a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, an hydroxyl, a substituted alkenyl, a substituted cycloaliphatic, a substituted aliphatic, a thiol, a thioalkoxy, a thioalkyl, a thioaryl, a thiol, a a thiophene, or a substituted thiophene; and $R_{10}$ and $R_{11}$ are each independently O or NH.

In some embodiments of this aspect of the disclosure, the detectable label can be a fluorescein, an acridine, an alizarene, an azo dye, an anthraquinine dye, a bodipy dye, a coumarin dye, a cyanine dye, a lanthanide complex, an oxazine dye, a phenazathionium dye, a phenazoxonium dye, a porphyorin, a pyrene, a pyrilium, a perylene, a phenoxazine, a phenezine, a rhodol, a rhodamine, or a xanthene dye.

In some embodiments of this aspect of the disclosure, the detectable label can have a caging group covalently attached thereto by an esterase-cleavable ester bond.

In some embodiments of this aspect of the disclosure, the detectable label can be a fluorophore or a dye having a caging group covalently attached thereto by an esterase-cleavable ester bond, wherein said caging group is an acetoxymethyl group.

In some embodiments of this aspect of the disclosure, the probe can further comprise a *mycobacterium*-specific decaprenylphosphoryl-β-D-ribose 2'-epimerase (DprE1)-trapping moiety, or an ester or salt thereof, said DprE1-trapping moiety being covalently attached to the detectable label.

In some embodiments of this aspect of the disclosure, the *mycobacterium*-specific DprE1-trapping moiety can be covalently attached to the detectable label by a first linker.

In some embodiments of this aspect of the disclosure, the *mycobacterium*-specific DprE1-trapping moiety can have the formula:

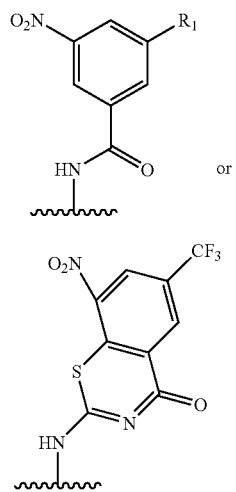

and
wherein $R_1$ is H, —$NO_2$, or $CF_3$.

In some embodiments of this aspect of the disclosure, the first linker can be selected from the group consisting of: ethoxyphenyl, —$CH_2$—$CH_2$—, -1-ethyl 3-methyl 1,2,3-triazole, and —$CH_2$—$CH_2$—$NR_2$—CS—$NH_2$—, wherein $R_2$ is H or —$CH_3$.

In some embodiments of this aspect of the disclosure, the method can further comprise, before the step of detecting the detectable label, washing the sample to remove probe not in contact with mycobacteria therein.

In some embodiments of this aspect of the disclosure, the step of detecting the detectable signal comprises measuring fluorescence emission intensity.

In some embodiments of this aspect of the disclosure, the step of detecting the detectable signal comprises measuring absorbance intensity.

In some embodiments of this aspect of the disclosure, the step of detecting the detectable signal comprises measuring luminescence emission intensity.

In some embodiments of this aspect of the disclosure, the step of detecting the detectable signal comprises measuring observing a color change.

In some embodiments of this aspect of the disclosure, the step of detecting the detectable signal further comprises generating an image of the detected *mycobacterium*. In these embodiments of this aspect of the generated image is of detected *mycobacterium* in a small-animal body.

In some embodiments of this aspect of the method can further comprise the step of determining a count of the population of the detected *mycobacterium* in the sample.

In some embodiments of this aspect of the method can further comprise detecting the detectable signal using a portable detector.

In some embodiments of this aspect of the sample is a veterinary sample.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

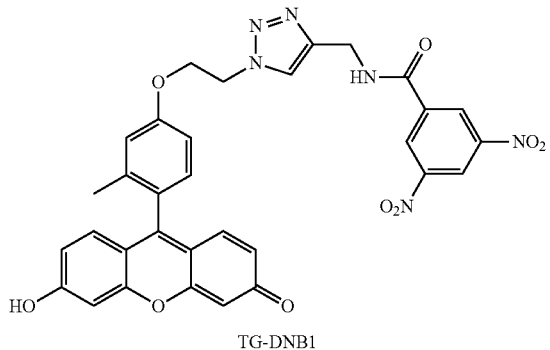 [SMILES: Cc1cc(OCCn2cc(CNC(=O)c3cc([N+](=O)[O-])cc([N+](=O)[O-])c3)nn2)ccc1-c1c2ccc(=O)cc-2oc2cc(O)ccc12]

TG-DNB1

Example 2

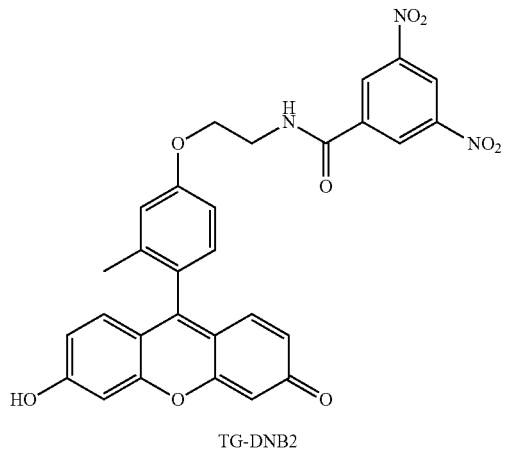 [SMILES: Cc1cc(OCCNC(=O)c2cc([N+](=O)[O-])cc([N+](=O)[O-])c2)ccc1-c1c2ccc(=O)cc-2oc2cc(O)ccc12]

TG-DNB2

Example 3

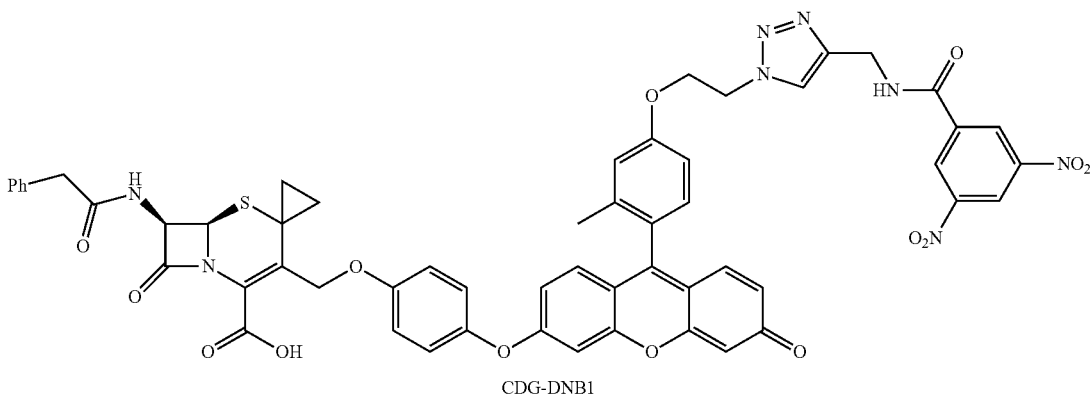 [SMILES: Cc1cc(OCCn2cc(CNC(=O)c3cc([N+](=O)[O-])cc([N+](=O)[O-])c3)nn2)ccc1-c1c2ccc(=O)cc-2oc2cc(Oc3ccc(OCC4=C(C(=O)O)N5C(=O)[C@@H](NC(=O)Cc6ccccc6)[C@H]5SC45CC5)cc3)ccc12]

CDG-DNB1

Example 4
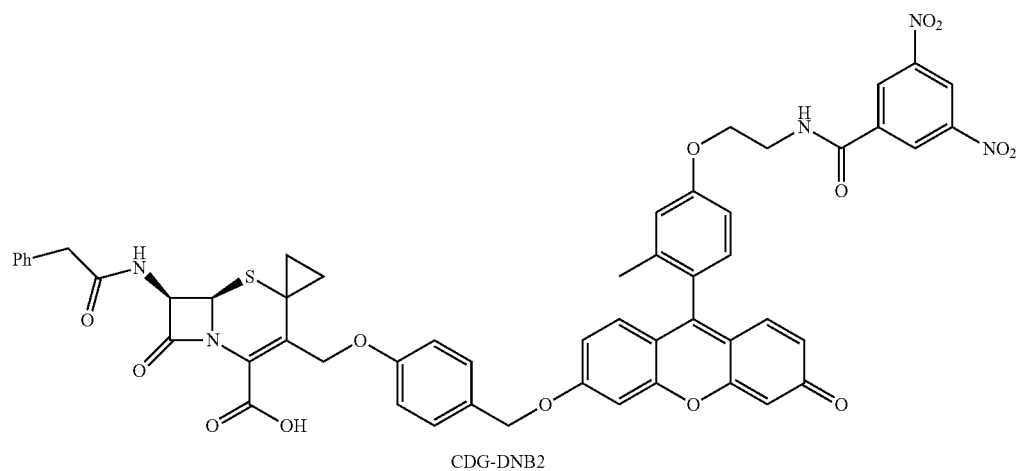 [SMILES: Cc1cc(OCCNC(=O)c2cc([N+](=O)[O-])cc([N+](=O)[O-])c2)ccc1-c1c2ccc(=O)cc-2oc2cc(OCc3ccc(OCC4=C(C(=O)O)N5C(=O)[C@@H](NC(=O)Cc6ccccc6)[C@H]5SC45CC5)cc3)ccc12]
CDG-DNB2
Example 5
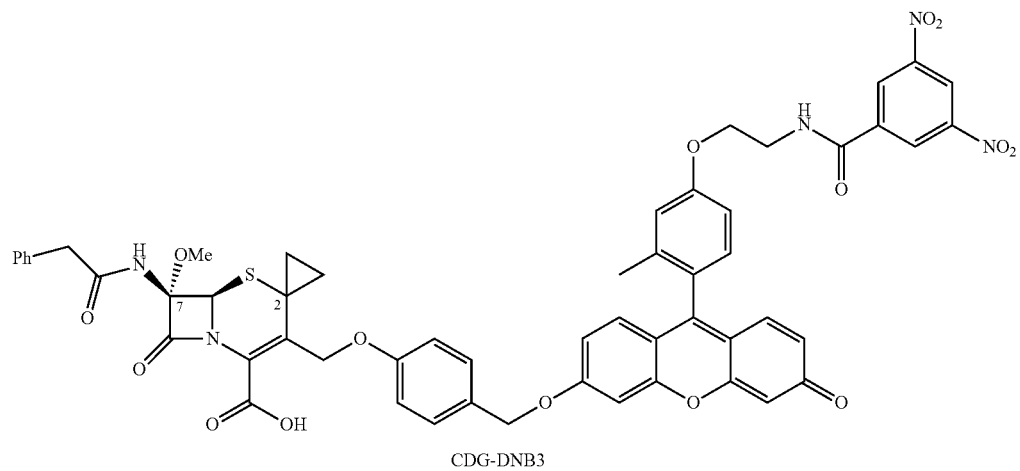 [SMILES: CO[C@@]1(NC(=O)Cc2ccccc2)C(=O)N2C(C(=O)O)=C(COc3ccc(COc4ccc5c(-c6ccc(OCCNC(=O)c7cc([N+](=O)[O-])cc([N+](=O)[O-])c7)cc6C)c6ccc(=O)cc-6oc5c4)cc3)C3(CC3)S[C@@H]21]
CDG-DNB3
Example 6
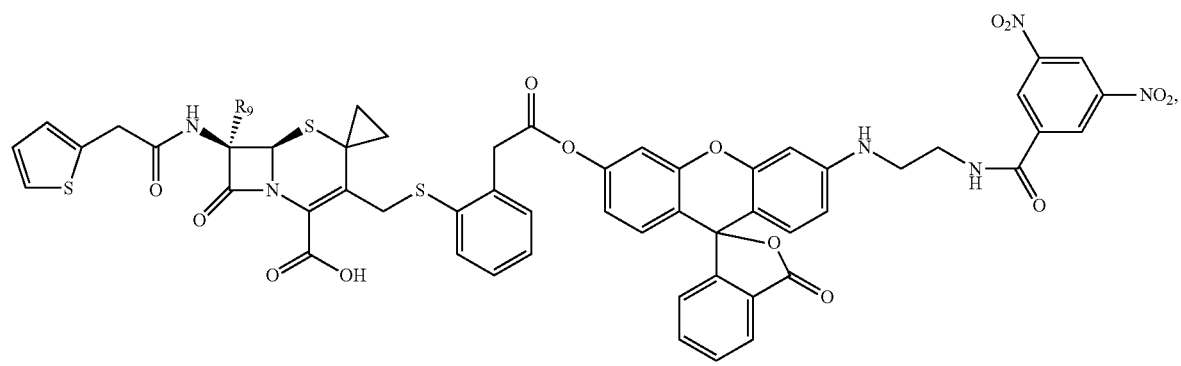

R₉ can be, but is not limited to, H, OMe, Me, —CH₂CH₃, —CF₃, —CH₂CF₃, —CF₂CH₃, —CHF₂, —CH₂F, —OCH₂F, or —OCHF₂
Example 7
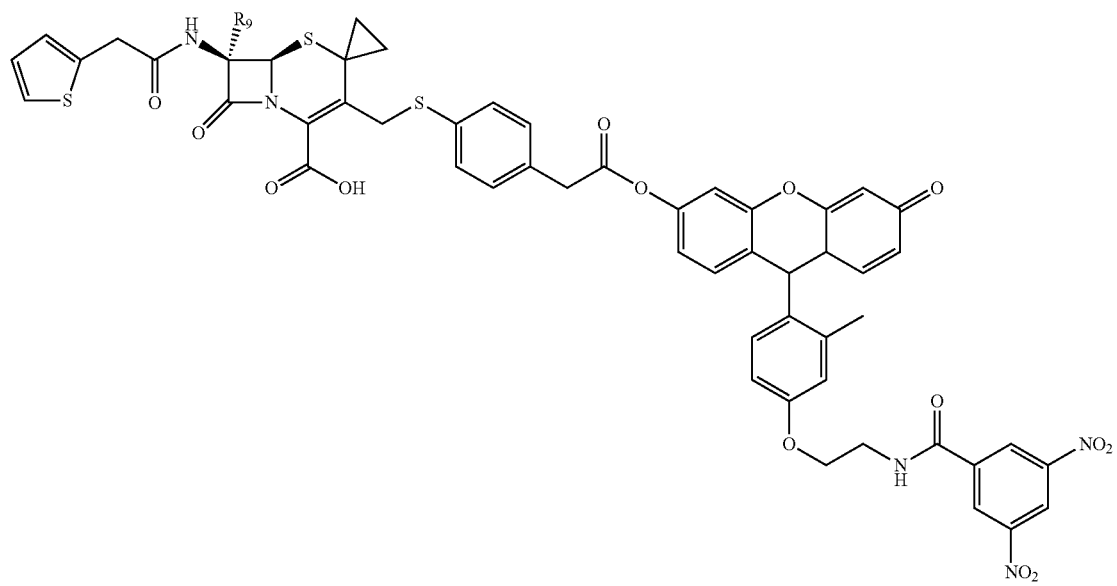
R₉ can be, but is not limited to, H, OMe, Me, —CH₂CH₃, —CF₃, —CH₂CF₃, —CF₂CH₃, —CHF₂, —CH₂F, —OCH₂F, or —OCHF₂
Example 8
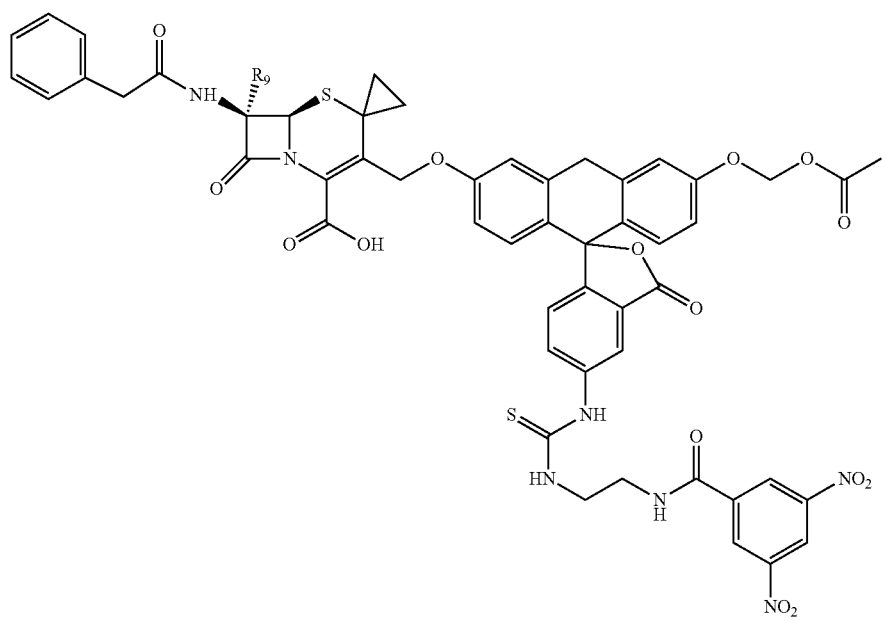

R$_9$ can be, but is not limited to, H, OMe, Me, —CH$_2$CH$_3$, —CF$_3$, —CH$_2$CF$_3$, —CF$_2$CH$_3$, —CHF$_2$, —CH$_2$F, —OCH$_2$F, or —OCHF$_2$

Example 9

Figure 18:
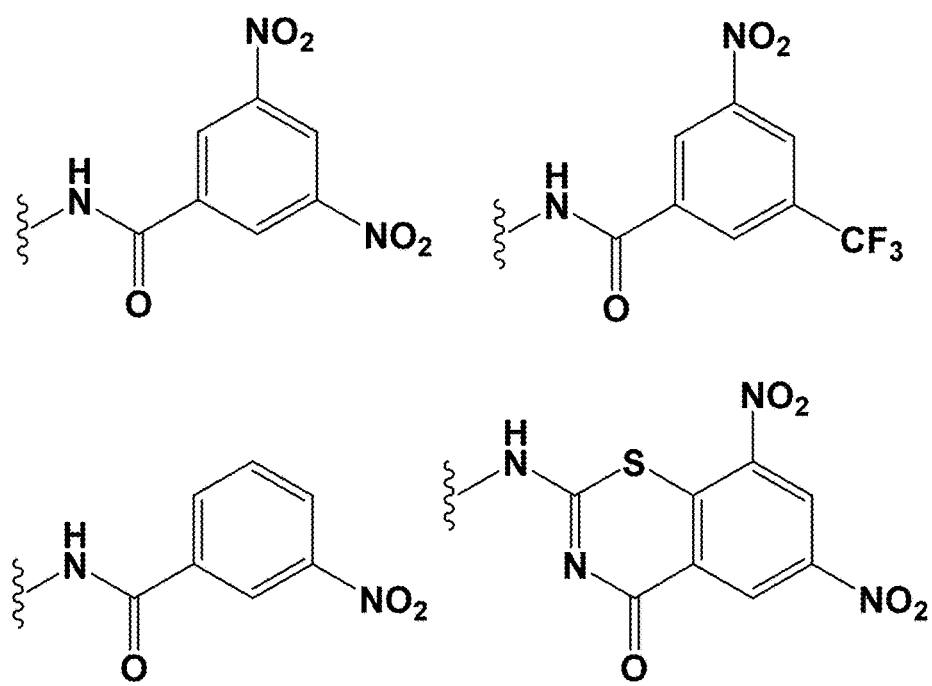
FIG. 18 illustrates examples of DprE1-trapping moieties suitable for incorporation into embodiments of the probes of the disclosure.

Examples, but not intended to be limiting, of DprE1-trapping moieties suitable for incorporation into embodiments of the probes of the disclosure are illustrated in FIG. 18.

Example 10

Figure 13:
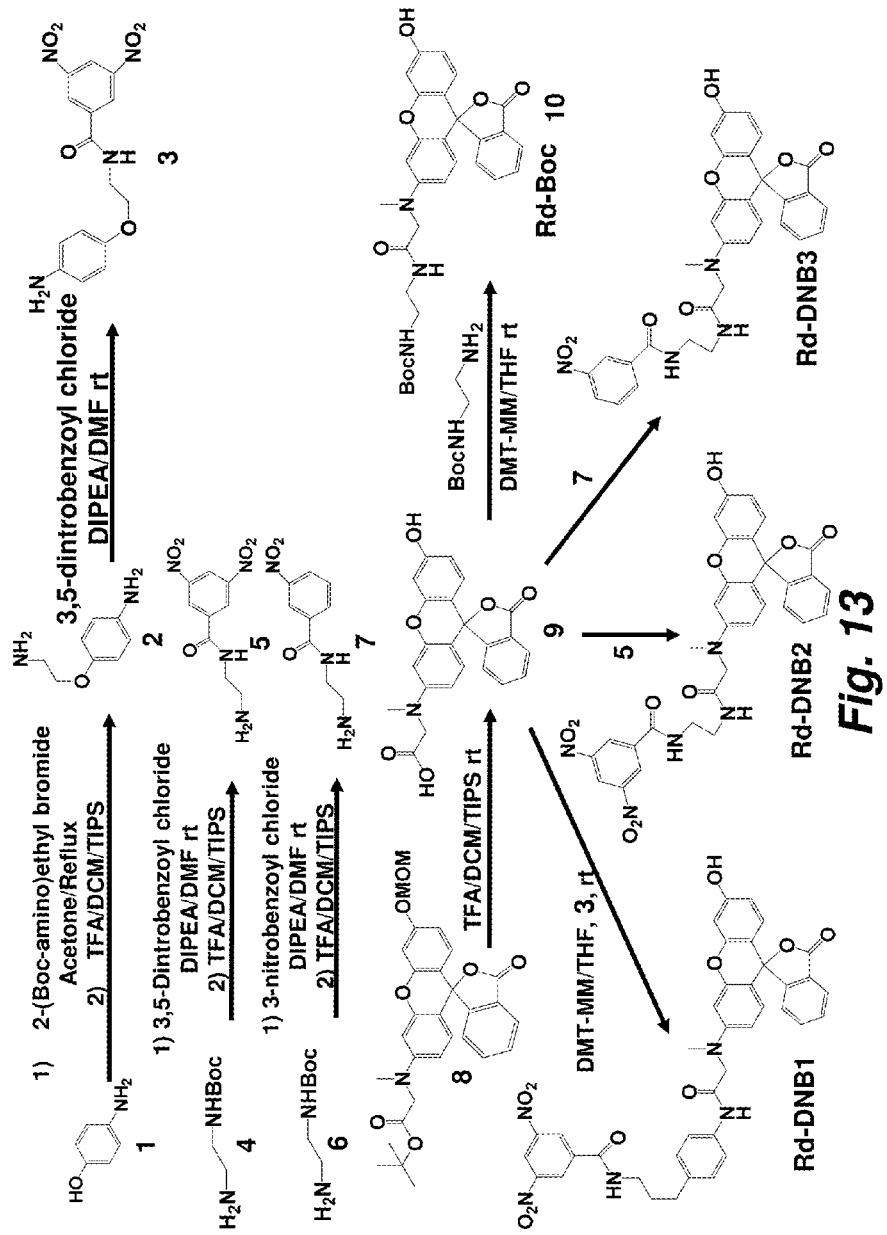
FIG. 13 schematically illustrates the synthesis of Rd-DNB analogues.

FIG. 13 schematically illustrates the synthesis of Rhodol-dinitrobenzamide (Rd-DNB) analogues of the disclosure. The key Rd analogue intermediate 9 was obtained through deprotection of 8. Selective amidation with the corresponding amine analogue in the presence of DMT-MM afforded the Rd-DNB analogues.

Example 11

Figure 14:
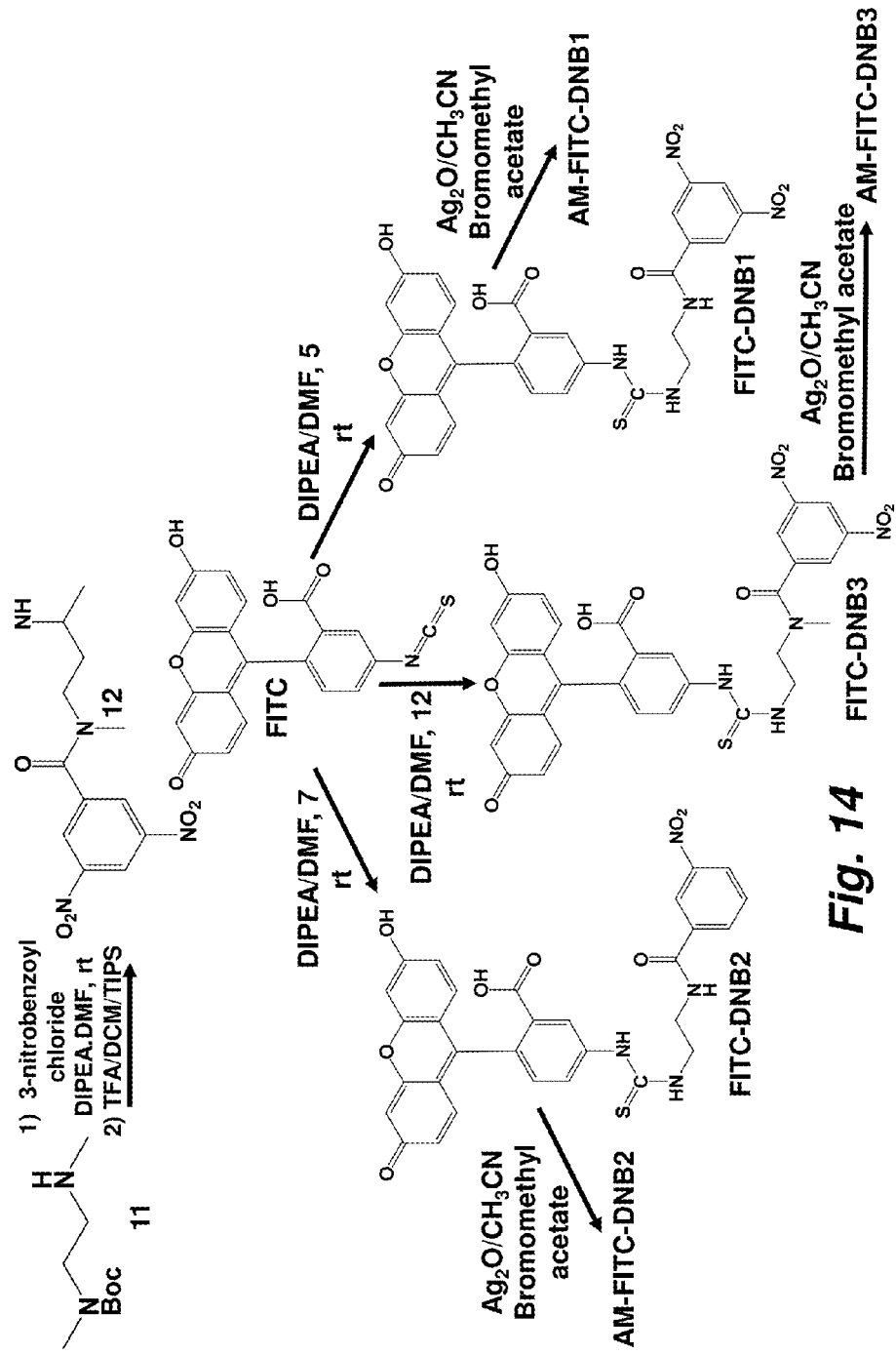
FIG. 14 schematically illustrates the synthesis of FITC-DNB analogues and their caging with acetoxymethyl esterification.

FIG. 14 schematically illustrates the synthesis of FITC-DNB analogues obtained through a conjugation of FITC with corresponding DNB derivatives, and further derivatization to the AM esters of FITC-DNBs.

Example 12

TG-DNB1 synthesis is shown in FIG. 3, which started with a substitution reaction of 4-hydroxy-2-methylbenzaldehyde 13 to obtain azido-derivative 14. Condensation with resorcinol afforded 15, followed by ring-closure reaction in the presence of DDQ to obtain key intermediate 16. A copper-catalyzed click reaction of 16 with dinitro-benzoyl alkyne 19, which was obtained from dinitrobenzoyl chloride 18, afforded TG-DNB1.

Example 14

Synthesis of TG-DNB2, as shown in FIGS. 4A and 4B, started with a substitution reaction of 4-bromo-3-methylphenol 20 to obtain 14. Boc deprotection and allyl protection provided key intermediate 22. Substitution with 23 in presence of n-BuLi obtained key intermediate 24, which further reacted with dinitrobenzoyl chloride after allyl deprotection afforded final compound TG-NDB2.

REFERENCES

1. Dye C, et al. (2008) Measuring tuberculosis burden, trends, and the impact of control programs. *Lancet Infect. Dis.* 8(4):233-243.
2. Zumla A, Raviglione M, Hafner R, & von Reyn C F (2013) Tuberculosis. *N. Engl. J. Med.* 368(8):745-755.
3. Anonymous (2013) Global Tuberculosis Report 2013, World Health Organization.
4. Urdea M, et al. (2006) Requirements for high impact diagnostics in the developing world. *Nature* 444 Suppl 1:73-79.
5. Keeler E, et al. (2006) Reducing the global burden of tuberculosis: the contribution of improved diagnostics. *Nature* (444):49-57.
6. McNerney R & Daley P (2011) Towards a point-of-care test for active tuberculosis: obstacles and opportunities. *Nat. Rev. Microbiol.* 9(3):204-213.
7. Dheda K, Ruhwald M, Theron G, Peter J, & Yam W C (2013) Point-of-care diagnosis of tuberculosis: past, present and future. *Respirology* 18(2):217-232.
8. Bush K & Jacoby G A (2010) Updated Functional Classification of beta-Lactamases. *Antimicrob. Agents Chemother.* 54(3):969-976.
9. Zlokarnik G, et al. (1998) Quantitation of transcription and clonal selection of single living cells with beta-lactamase as reporter. *Science* 279(5347):84-88.
10. Gao W Z, Xing B G, Tsien R Y, & Rao J H (2003) Novel fluorogenic substrates for imaging 6-lactamase gene expression. *J. Am. Chem. Soc.* 125(37):11146-11147.
11. Xing B, Khanamiryan A, & Rao J H (2005) Cell-permeable near-infrared fluorogenic substrates for imaging beta-lactamase activity. *J. Am. Chem. Soc.* 127(12):4158-4159.
12. Yao H, So M K, & Rao J (2007) A bioluminogenic substrate for in vivo imaging of beta-lactamase activity. *Angew. Chem.-Int. Edit.* 46(37):7031-7034.
13. Kong Y, et al. (2010) Imaging tuberculosis with endogenous beta-lactamase reporter enzyme fluorescence in live mice. *Proc. Natl. Acad. Sci. U.S.A* 107(27):12239-12244.
14. Rukavishnikov A, Gee K R, Johnson I, & Corry S (2011) Fluorogenic cephalosporin substrates for beta-lactamase TEM-1. *Anal. Biochem.* 419(1):9-16.
15. Zhang J X, Shen Y, May S L, Nelson D C, & Li S W (2012) Ratiometric fluorescence detection of pathogenic bacteria resistant to broad-spectrum ss-lactam antibiotics. *Angew. Chem.-Int. Edit.* 51(8):1865-1868.
16. Shi H B, et al. (2014) Engineering the Stereochemistry of Cephalosporin for Specific Detection of Pathogenic Carbapenemase-Expressing Bacteria. *Angew. Chem.-Int Edit.* 53(31):8113-8116.
17. Cheng Y F, et al. (2014) Fluorogenic Probes with Substitutions at the 2 and 7 Positions of Cephalosporin are Highly BlaC-Specific for Rapid *Mycobacterium tuberculosis* Detection. *Angew. Chem.-Int. Edit.* 53(35):9360-9364.
18. Xie H X, et al. (2012) Rapid point-of-care detection of the tuberculosis pathogen using a BlaC-specific fluorogenic probe. *Nat. Chem.* 4(10):802-809.
19. Makarov V, et al. (2009) Benzothiazinones Kill *Mycobacterium tuberculosis* by Blocking Arabinan Synthesis. *Science* 324(5928):801-804.
20. Ribeiro A, et al. (2011) Analogous Mechanisms of Resistance to Benzothiazinones and Dinitrobenzamides in *Mycobacterium smegamatis. PLoS One* 6(11):7.
21. Trefzer C, et al. (2010) Benzothiazinones: Prodrugs That Covalently Modify the Decaprenylphosphoryl-beta-D-ribose 2'-epimerase DprE1 of *Mycobacterium tuberculosis*. *J. Am. Chem. Soc.* 132(39):13663-13665.
22. van der Poll T & Opal S M (2009) Pathogenesis, treatment, and prevention of pneumococcal pneumonia. *Lancet* 374(9700):1543-1556.
23. Cole A M, et al. (2001) Determinants of *Staphylococcus aureus* nasal carriage. *Clin. Diagn. Lab. Immunol.* 8(6):1064-1069.
24. Watkins D A, Chahine A, Creger R J, Jacobs M R, & Lazarus H M (1993) *CORYNEBACTERIUM-STRIATUM*—A DIPHTHEROID WITH PATHOGENIC POTENTIAL. *Clin. Infect. Dis.* 17(1):21-25.
25. Paik S, et al. (2005) Identification of virulence determinants for endocarditis in *Streptococcus sanguinis* by signature-tagged mutagenesis. *Infect. Immun.* 73(9):6064-6074.

The invention claimed is:

1. A probe specific for a *mycobacterium*, said probe comprising a β-lactamase substrate group covalently attached to a detectable label group, wherein the β-lactamase substrate group has the formula VI:

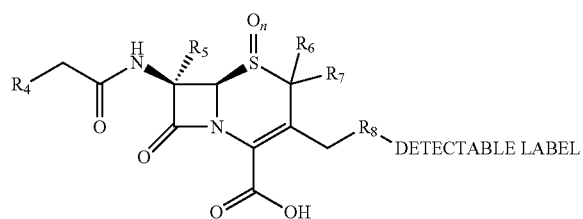

VI wherein, in the β-lactamase substrate group:
n=0 or 1;
$R_4$ is selected from the group consisting of: a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, a substituted alkenyl, a substituted cycloaliphatic, a substituted aliphatic, a thiol, a thioalkoxy, a thioalkyl, a thioaryl, a thiophene, or a substituted thiophene;
$R_5$ is Me, —$CH_2CH_3$, —$CF_3$, —$CH_2CF_3$, —$CF_2CH_3$, —$CHF_2$, —$CH_2F$, —$OCH_2F$, or $OCHF_2$;
$R_6$ and $R_7$ are each H or

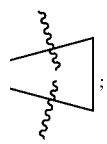 [SMILES: *CC*];

and
$R_8$ is O or S,
and wherein the detectable label has a caging group covalently attached thereto by an esterase-cleavable ester bond, wherein the detectable label is a fluorophore or a dye having the caging group covalently attached thereto by an esterase-cleavable ester bond, wherein said caging group is an acetoxymethyl group.

2. A probe specific for a *mycobacterium*, said probe comprising a β-lactamase substrate group covalently attached to a detectable label group, wherein the β-lactamase substrate group has the formula VI:

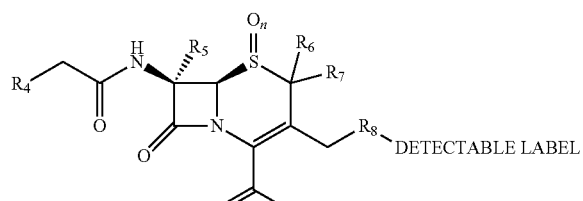

VI wherein, in the β-lactamase substrate group:
n=0 or 1;
$R_4$ is selected from the group consisting of: a hydrogen, an alkyl, a substituted alkyl, an alkoxy, an alkoxycarbonyl, an alkoxyl, an alkoxyalkyl, an alkylene, an aralkoxycarbonyl, an aralkyl, an aralkyloxyl, an aroyl, an aroylamino, an aryl, a substituted aryl group, a carbamoyl, a carbonyl, a carboxamide, a carboxyl, a heteroaryl, a heterocyclic, a hydroxyalkyl, a substituted alkenyl, a substituted cycloaliphatic, a substituted aliphatic, a thiol, a thioalkoxy, a thioalkyl, a thioaryl, a thiophene, or a substituted thiophene;
$R_5$ is Me, —$CH_2CH_3$, —$CF_3$, —$CH_2CF_3$, —$CF_2CH_3$, —$CHF_2$, —$CH_2F$, —$OCH_2F$, or —$OCHF_2$;
$R_6$ and $R_7$ are each H or

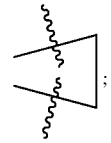 [SMILES: *CC*];

and
$R_8$ is O or S,
and wherein the detectable label has a caging group covalently attached thereto by an esterase-cleavable ester bond, said probe further comprising a *mycobacterium*-specific decaprenylphosphoryl-β-D-ribose 2'-epimerase (DprE1)-trapping moiety, or an ester or salt thereof, said DprE1-trapping moiety covalently attached to the detectable label.

3. The probe of claim 2, wherein said *mycobacterium*-specific DprE1-trapping moiety is covalently attached to the detectable label by a first linker.

4. The probe of claim 2, wherein said *mycobacterium*-specific DprE1-trapping moiety has the formula:

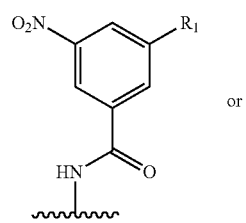

I or

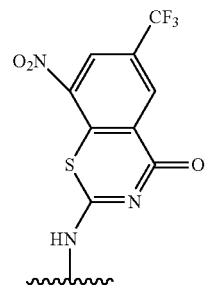

II and
wherein $R_1$ is H, —$NO_2$, or $CF_3$.

5. The probe of claim 2, wherein the first linker is selected from the group consisting of: ethoxyphenyl, —$CH_2$—$CH_2$—, -1-ethyl 3-methyl 1,2,3-triazole, and —$CH_2$—$CH_2$—$NR_2$—CS—$NH_2$—, wherein $R_2$ is H or —$CH_3$.

6. A probe specific for a *mycobacterium,* wherein the probe is selected from the group consisting of:
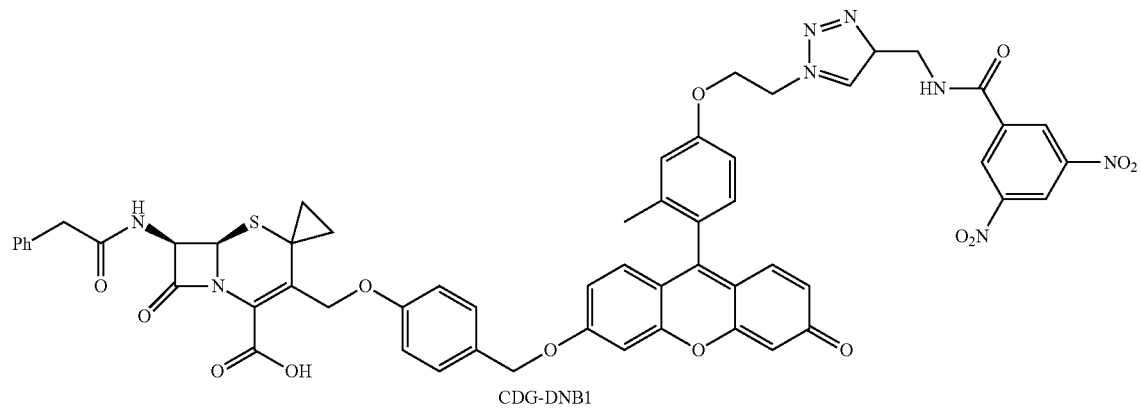
CDG-DNB1
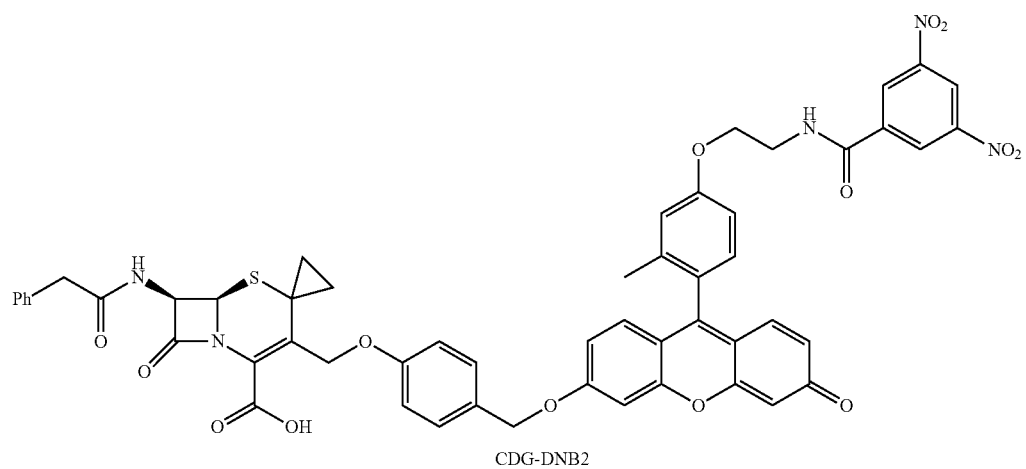
CDG-DNB2
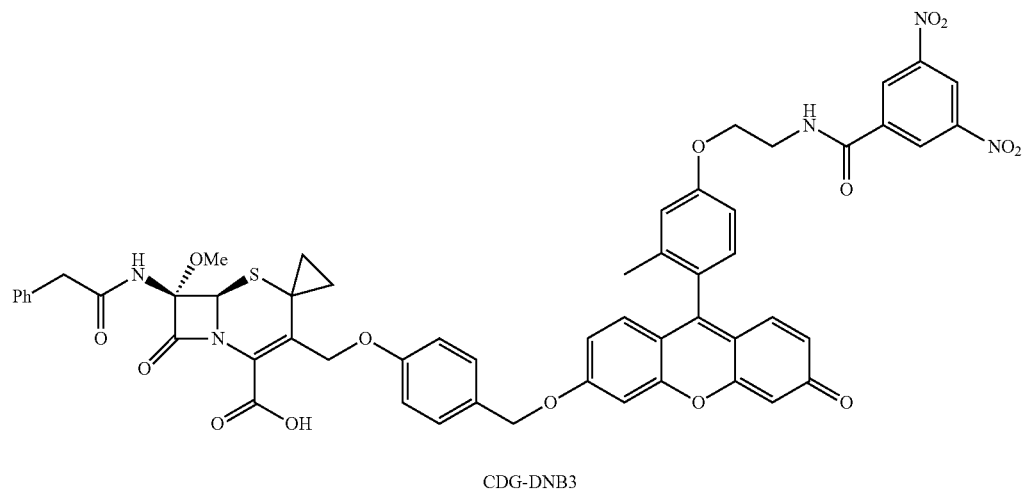
CDG-DNB3

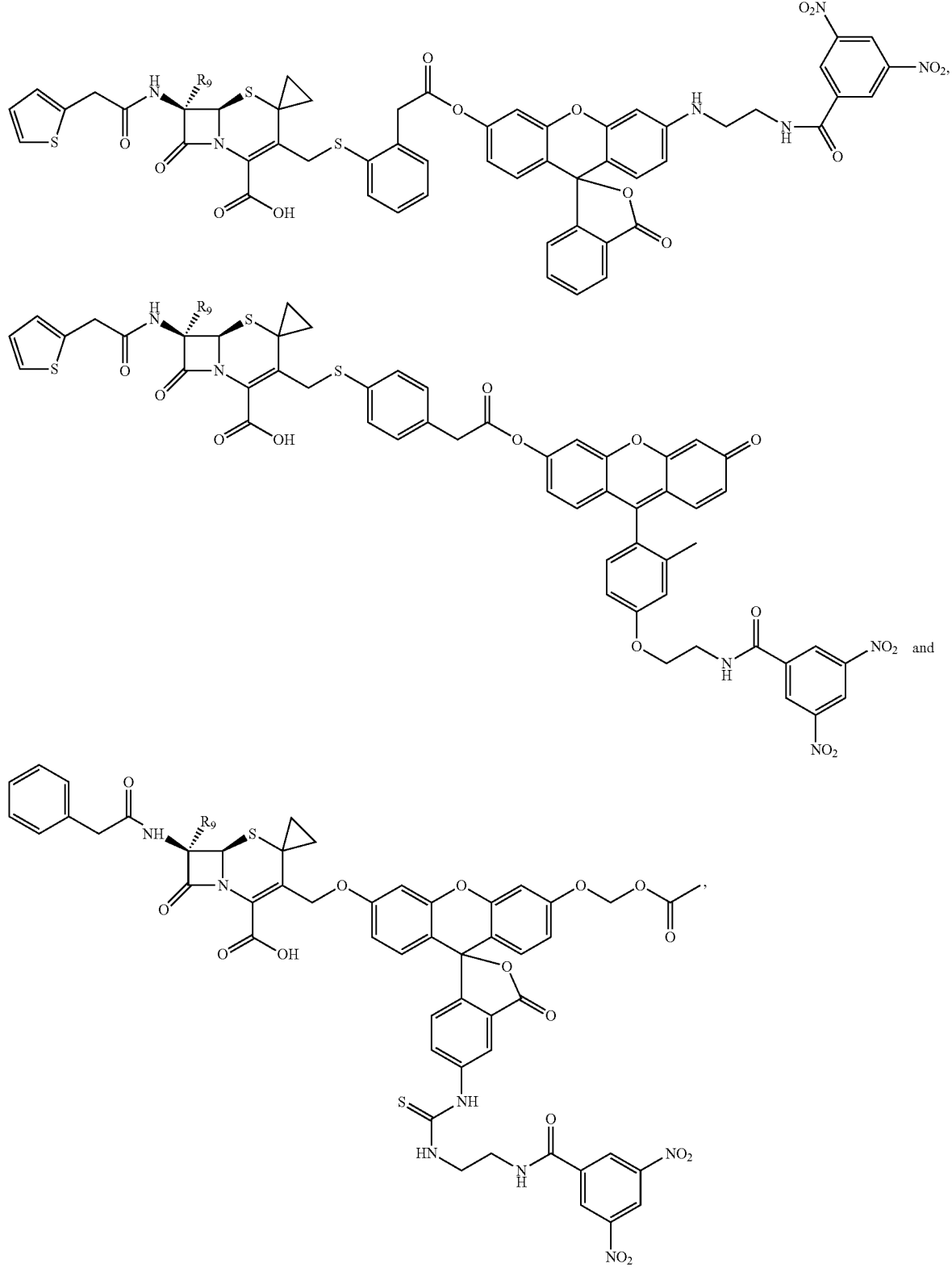
wherein $R_9$ is each independently Me, —$CH_2CH_3$, —$CF_3$, —$CH_2CF_3$, —$CF_2CH_3$, —$CHF_2$, —$CH_2F$, —$OCH_2F$, or —$OCHF_2$.
* * * * *

UNITED STATES PATENT AND TRADEMARK OFFICE
CERTIFICATE OF CORRECTION

PATENT NO. : 10,370,538 B2
APPLICATION NO. : 15/001591
DATED : August 6, 2019
INVENTOR(S) : Jianghong Rao et al.

Page 1 of 1

It is certified that error appears in the above-identified patent and that said Letters Patent is hereby corrected as shown below:

In the Specification

Add the following Statement Regarding Federally Sponsored Research or Support:
Column 1, Line 20, "This invention was made with Government Support under Grant No. AI125286 awarded by the National Institutes of Health. The government has certain rights in the invention."

Signed and Sealed this
Eleventh Day of November, 2025

John A. Squires
*Director of the United States Patent and Trademark Office*